(12) United States Patent
Palovich et al.

(10) Patent No.: US 6,680,317 B2
(45) Date of Patent: Jan. 20, 2004

(54) IL-8 RECEPTOR ANTAGONISTS

(75) Inventors: Michael R. Palovich, Lansdale, PA (US); Katherine L. Widdowson, King of Prussia, PA (US); Hong Nie, Conshohocken, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/221,908

(22) PCT Filed: Mar. 23, 2001

(86) PCT No.: PCT/US01/09216

§ 371 (c)(1),
(2), (4) Date: Sep. 17, 2002

(87) PCT Pub. No.: WO01/72960

PCT Pub. Date: Oct. 4, 2001

(65) Prior Publication Data

US 2003/0216375 A1 Nov. 20, 2003

(51) Int. Cl.[7] ............... A61K 31/18; A61K 31/277; A61K 31/40; A61K 31/42; A61K 31/495

(52) U.S. Cl. ............... 514/252.12; 514/227.5; 514/238.5; 514/255.01; 514/378; 514/380; 514/426; 514/603; 544/58.2; 544/59; 544/163; 544/382; 544/383; 548/240; 548/245; 548/246; 548/557; 548/558; 564/86

(58) Field of Search ............... 544/383, 58.2, 544/59, 163, 382; 514/252.12, 227.5, 238.5, 255.01, 378, 380, 426, 603; 548/240, 245, 246, 557, 558; 564/86

(56) References Cited

U.S. PATENT DOCUMENTS 6,214,880 B1    4/2001   Houze ............... 514/595

FOREIGN PATENT DOCUMENTS

| WO | WO 97 29743 | 8/1997 |
| WO | WO 98 06397 | 2/1998 |

*Primary Examiner*—Peter O'Sullivan
(74) *Attorney, Agent, or Firm*—Soma G. Simon; Mary E. McCarthy; Charles M. Kinzig

(57) ABSTRACT

This invention relates to novel compounds of Formula (I), and compositions thereof, useful in the treatment of disease states mediated by the chemokine, Interleukin-8 (IL-8).

14 Claims, No Drawings

IL-8 RECEPTOR ANTAGONISTS

This application is a 371 of PCT/US01/09216 filed Mar. 23, 2001.

FIELD OF THE INVENTION

This invention relates to novel sulfonamide substituted diphenyl thiourea compounds, pharmaceutical compositions, processes for their preparation, and use thereof in treating IL-8, GROα, GROβ, GROγ, NAP-2, and ENA-78 mediated diseases.

BACKGROUND OF THE INVENTION

Many different names have been applied to Interleukin-8 (IL8), such as neutrophil attractant/activation protein-1 (NAP-1), monocyte derived neutrophil chemotactic factor (MDNCF), neutrophil activating factor (NAF), and T-cell lymphocyte chemotactic factor. Interleukin-8 is a chemoattractant for neutrophils, basophils, and a subset of T-cells. It is produced by a majority of nucleated cells including macrophages, fibroblasts, endothelial and epithelial cells exposed to TNF, IL-1α, IL-1β or LPS, and by neutrophils themselves when exposed to LPS or chemotactic factors such as FMLP. M. Baggiolini et al., *J. Clin. Invest.* 84, 1045 (1989); J. Schroder et al, *J. Immunol.* 139, 3474 (1987) and *J. Immunol.* 144, 2223 (1990); Strieter, et al., *Science* 243, 1467 (1989) and *J. Biol. Chem.* 264, 10621 (1989); Cassatella et al., *J. Immunol.* 148, 3216 (1992).

GROα, GROβ, GROγ and NAP-2 also belong to the chemokine family. Like IL-8 these chemokines have also been referred to by different names. For instance GROα, β, γ have been referred to as MGSAα, β and γ respectively (Melanoma Growth Stimulating Activity), see Richmond et al., *J. Cell Physiology* 129, 375 (1986) and Chang et al., *J. Immunol* 148, 451 (1992). All of the chemokines of the α-family which possess the ELR motif directly preceding the CXC motif bind to the IL-8 B receptor (CXCR2).

IL-8, GROα, GROβ, GROγ, NAP-2, and ENA-78 stimulate a number of a functions in vitro. They have all been shown to have chemoattractant properties for neutrophils, while IL-8 and GROα have demonstrated T-lymphocytes, and basophilic chemotactic activity. In addition IL-8 can induce histamine release from basophils from both normal and atopic individuals. GRO-α and IL-8 can in addition, induce lysozomal enzyme release and respiratory burst from neutrophils. IL-8 has also been shown to increase the surface expression of Mac-1 (CD11b/CD18) on neutrophils without de novo protein synthesis. This may contribute to increased adhesion of the neutrophils to vascular endothelial cells. Many known diseases are characterized by massive neutrophil infiltration. As IL-8, GROα, GROβ, GROγ and NAP-2 promote the accumulation and activation of neutrophils, these chemokines have been implicated in a wide range of acute and chronic inflammatory disorders including psoriasis and rheumatoid arthritis, Baggiolini et al., *FEBS Lett.* 307, 97 (1992); Miller et al., *Crit. Rev. Immunol.* 12, 17 (1992); Oppenheim et al., *Annu. Rev. Immunol.* 9, 617 (1991); Seitz et al., *J. Clin. Invest.* 87, 463 (1991); Miller et al., *Am. Rev. Respir. Dis.* 146, 427 (1992); Donnely et al., *Lancet* 341, 643 (1993). In addition the ELR chemokines (those containing the amino acids ELR motif just prior to the CXC motif) have also been implicated in angiostasis, Strieter et al., *Science* 258, 1798 (1992).

In vitro, IL-8, GROα, GROβ, GROγ and NAP-2 induce neutrophil shape change, chemotaxis, granule release, and respiratory burst, by binding to and activating receptors of the seven-transmembrane, G-protein-linked family, in particular by binding to IL-8 receptors, most notably the IL 8β receptor (CXCR2). Thomas et al., *J. Biol. Chem.* 266, 14839 (1991); and Holmes et al., *Science* 253, 1278 (1991). The development of non-peptide small molecule antagonists for members of this receptor family has precedent. For a review see R. Freidinger in: *Progress in Drug Research*, Vol. 40, pp. 33–98, Birkhauser Verlag, Basel 1993. Hence, the IL-8 receptor represents a promising target for the development of novel anti-inflammatory agents.

Two high affinity human IL-8 receptors (77% homology) have been characterized: IL-8Rα, which binds only IL8 with high affinity, and IL-8Rβ, which has high affinity for IL-8 as well as for GROα, GROβ, GROγ and NAP-2. See Holmes et al., supra; Murphy et al., *Science* 253, 1280 (1991); Lee et al., *J. Biol. Chem.* 267, 16283 (1992); LaRosa et al., *J. Biol. Chem.* 267, 25402 (1992); and Gayle et al., *J. Biol. Chem.* 268, 7283 (1993).

There remains a need for treatment, in this field, for compounds, which are capable of binding to the IL-8 α or β receptor. Therefore, conditions associated with an increase in IL-8 production (which is responsible for chemotaxis of neutrophil and T-cells subsets into the inflammatory site) would benefit by compounds, which are inhibitors of IL-8 receptor binding.

SUMMARY OF THE INVENTION

This invention provides for a method of treating a chemokine mediated disease, wherein the chemokine is one which binds to an IL-8 a or b receptor and which method comprises administering an effective amount of a compound of Formula (I) or a pharmaceutically acceptable salt thereof. In particular the chemokine is IL-8.

This invention also relates to a method of inhibiting the binding of IL-8 to its receptors in a mammal in need thereof which comprises administering to said mammal an effective amount of a compound of Formula (I).

The present invention also provides for the novel compounds of Formula (I), and pharmaceutical compositions comprising a compound of Formula (I), and a pharmaceutical carrier or diluent.

Compounds of Formula (I) useful in the present invention are represented by the structure:

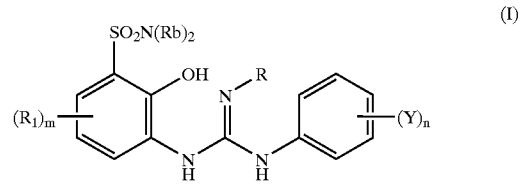

wherein:

R is selected from the group consisting of cyano, $OR_{11}$, $C(O)NR_{15}R_{16}$, $R_{18}$, $C(O)OR_{11}$, $C(O)R_{11}$, and $S(O)_2R_{17}$;

$R_b$ is independently selected from the group consisting of hydrogen, $NR_6R_7$, OH, $OR_a$, $C_{1-5}$alkyl, aryl, aryl$C_{1-4}$alkyl, aryl $C_{2-4}$alkenyl; cycloalkyl, cycloalkyl $C_{1-5}$ alkyl, heteroaryl, heteroaryl$C_{1-4}$alkyl, heteroaryl$C_{2-4}$ alkenyl, heterocyclic, heterocyclic $C_{1-4}$alkyl, and a heterocyclic $C_{2-4}$alkenyl moiety, all of which moieties are optionally substituted one to three times independently by a substituent selected from the group consisting of halogen, nitro, halosubstituted $C_{1-4}$ alkyl, $C_{1-4}$ alkyl, amino, mono and di-$C_{1-4}$ alkyl substituted amine, $OR_a$, $C(O)R_a$, $NR_aC(O)OR_a$, $OC(O)NR_6R_7$, hydroxy, $NR_9C(O)R_a$, $S(O)_tR_a$, $C(O)NR_6R_7$, $C(O)OH$, $C(O)OR_a$, $S(O)_tNR_6R_7$, and $NHS(O)_tR_a$; or the two $R_b$ substituents join to form a 3–10 membered ring, and containing, in addition to optionally substituted $C_{1-9}$ alkyl, independently, 0 to 3 substituents selected from the group consisting of $NR_a$, $C(O)$, O, S, SO, and $SO_2$ moieties which are unsaturated or saturated.

$R_a$ is selected from the group consisting if alkyl, aryl, aryl$C_{1-4}$alkyl, heteroaryl, heteroaryl $C_{1-4}$alkyl, heterocyclic, $COOR_a$, and a heterocyclic $C_{1-4}$alkyl moiety, all of which moieties are optionally substituted;

m is an integer having a value of 1 to 3;

m' is 0, or an integer having a value of 1 or 2;

n is an integer having a value of 1 to 3;

q is 0, or an integer having a value of 1 to 10;

t is 0, or an integer having a value of 1 or 2;

s is an integer having a value of 1 to 3;

$R_1$ is independently selected from the group consisting of hydrogen, halogen, nitro, cyano, $C_{1-10}$ alkyl, halosubstituted $C_{1-10}$ alkyl, $C_{2-10}$ alkenyl, $C_{1-10}$ alkoxy, halosubstituted $C_{1-10}$alkoxy, azide,$S(O)_tR_4$, $(CR_8R_8)_qS(O)_tR_4$, hydroxy, hydroxy substituted $C_{1-4}$alkyl,aryl, aryl $C_{1-4}$ alkyl, aryl $C_{2-10}$ alkenyl, aryloxy, aryl $C_{1-4}$ alkyloxy, heteroaryl, heteroarylalkyl, heteroaryl $C_{2-10}$ alkenyl, heteroaryl $C_{1-4}$ alkyloxy, heterocyclic, heterocyclic $C_{1-4}$alkyl, heterocyclic$C_{1-4}$alkyloxy, heterocyclic$C_{2-10}$ alkenyl, $(CR_8R_8)_qNR_4R_5$, $(CR_8R_8)_qC(O)NR_4R_5$, $C_{2-10}$ alkenyl $C(O)NR_4R_5$, $(CR_8R_8)_qC(O)NR_4R_{10}$, $S(O)_3R_8$, $(CR_8R_8)_qC(O)R_{11}$, $C_{2-10}$ alkenyl $C(O)R_{11}$, $C_{2-10}$ alkenyl $C(O)OR_{11}$, $(CR_8R_8)_qC(O)OR_{11}$, $(CR_8R_8)_qOC(O)R_{11}$, $(CR_8R_8)_qNR_4C(O)R_{11}$, $(CR_8R_8)_qC(NR_4)NR_4R_5$, $(CR_8R_8)_qNR_4C(NR_5)R_{11}$, $(CR_8R_8)_qNHS(O)_2R_{13}$, and $(CR_8R_8)_qS(O)_2NR_4R_5$, or two $R_1$ moieties together form O—$(CH_2)_s$O or a 5 to 6 membered saturated or unsaturated ring, wherein the alkyl, aryl, arylalkyl, heteroaryl, or heterocyclic moieties are optionally substituted;

$R_4$ and $R_5$ are independently selected from the group consisting of hydrogen, optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, and heterocyclic$C_{1-4}$alkyl; or $R_4$ and $R_5$ together with the nitrogen to which they are attached form a 5 to 7 member ring which optionally comprises an additional heteroatom selected from the group consisting of O, N and S;

$R_6$ and $R_7$ are independently selected from the group consisting of hydrogen, $C_{1-4}$ alkyl, heteroaryl, aryl, alkyl aryl, and alkyl $C_{1-4}$ heteroalkyl; or $R_6$ and $R_7$ together with the nitrogen to which they are attached form a 5 to 7 member ring which ring optionally contains an additional heteroatom selected from the group consisting of oxygen, nitrogen and sulfur, which ring is optionally substituted;

Y is selected from the group consisting of hydrogen, halogen, nitro, cyano, halosubstituted $C_{1-10}$ alkyl, $C_{1-10}$ alkyl, $C_{2-10}$ alkenyl, $C_{1-10}$ alkoxy, halosubstituted $C_{1-10}$alkoxy, azide, $(CR_8R_8)_qS(O)_tR_a$, $(CR_8R_8)_qOR_a$, hydroxy, hydroxy substituted $C_{1-4}$alkyl, aryl, aryl $C_{1-4}$ alkyl, aryloxy, aryl$C_{1-4}$ alkyloxy, aryl $C_{2-10}$ alkenyl, heteroaryl, heteroarylalkyl, heteroaryl $C_{1-4}$ alkyloxy, heteroaryl $C_{2-10}$ alkenyl, heterocyclic, heterocyclic $C_{1-4}$alkyl, heterocyclic$C_{2-10}$ alkenyl, $(CR_8R_8)_qNR_4R_5$, $C_{2-10}$ alkenyl $C(O)NR_4R_5$, $(CR_8R_8)_qC(O)NR_4R_5$, $(CR_8R_8)_qC(O)NR_4R_{10}$, $S(O)_3R_8$, $(CR_8R_8)_qC(O)R_{11}$, $C_{2-10}$ alkenyl$C(O)R_{11}$, $(CR_8R_8)_qC(O)OR_{11}$, $C_{2-10}$alkenyl$C(O)OR_{11}$, $(CR_8R_8)_qOC(O)R_{11}$, $(CR_8R_8)_qNR_4C(O)R_{11}$, $(CR_8R_8)_qNHS(O)_tR_{13}$, $(CR_8R_8)_qS(O)_tNR_4R_5$, $(CR_8R_8)_qC(NR_4)NR_4R_5$, and $(CR_8R_8)_qNR_4C(NR_5)R_{11}$; or two Y moieties together form O—$(CH_2)_s$—O or a 5 to 6 membered saturated or unsaturated ring; wherein the alkyl, aryl, arylalkyl, heteroaryl, heteroaryl alkyl, heterocyclic, heterocyclicalkyl groups are optionally substituted;

$R_8$ is hydrogen or $C_{1-4}$ alkyl;

$R_9$ is hydrogen or a $C_{1-4}$ alkyl;

$R_{10}$ is $C_{1-10}$ alkyl $C(O)_2R_8$;

$R_{11}$ is selected from the group consisting of hydrogen, optionally substituted $C_{1-4}$ alkyl, optionally substituted aryl, optionally substituted aryl $C_{1-4}$alkyl, optionally substituted heteroaryl, optionally substituted heteroaryl$C_{1-4}$alkyl, optionally substituted heterocyclic, and optionally substituted heterocyclic$C_{1-4}$alkyl; and $R_{13}$ is selected from the group consisting of $C_{1-4}$ alkyl, aryl, aryl $C_{1-4}$alkyl, heteroaryl, heteroaryl$C_{1-4}$alkyl, heterocyclic, and heterocyclic$C_{1-4}$alkyl;

or a pharmaceutically acceptable salt thereof.

DETAILED DESCRIPTION OF THE INVENTION

The compounds of Formula (I), may also be used in association with the veterinary treatment of mammals, other than humans, in need of inhibition of IL-8 or other chemokines which bind to the IL-8 α and β receptors. Chemokine mediated diseases for treatment, therapeutically or prophylactically, in animals include disease states such as those noted herein in the Methods of Treatment section.

Suitably, $R_b$ is independently hydrogen, $NR_6R_7$, OH, $OR_a$, $C_{1-4}$alkyl, aryl, aryl$C_{1-4}$alkyl, aryl $C_{2-4}$alkenyl, heteroaryl, heteroaryl$C_{1-4}$alkyl, heteroaryl$C_{2-4}$ alkenyl, heterocyclic, heterocyclic $C_{1-4}$alkyl, or a heterocyclic $C_{2-4}$alkenyl moiety, all of which moieties may be optionally substituted one to three times independently by halogen; nitro; halosubstituted $C_{1-4}$alkyl; $C_{1-4}$ alkyl; amino, mono or di-$C_{1-4}$ alkyl substituted amine; cycloalkyl, cycloalkyl $C_{1-5}$ alkyl, $OR_a$; $C(O)R_a$; $NR_aC(O)OR_a$; $OC(O)NR_6R_7$; aryloxy; aryl $C_{1-4}$ oxy; hydroxy; $C_{1-4}$ alkoxy; $NR_9C(O)R_a$; $S(O)_mR_a$; $C(O)NR_6R_7$; $C(O)OH$; $C(O)OR_a$; $S(O)_tNR_6R_7$; $NHS(O)_tR_a$; Alternatively, the two $R_b$ substituents can join to form a 3–10 membered ring, optionally substituted and containing, in addition to carbon, independently, 1 to 3 $NR_9$, O, S, SO, or $SO_2$ moieties which can be optionally substituted.

Suitably, $R_a$ is an alkyl, aryl, aryl$C_{1-4}$alkyl, heteroaryl, heteroaryl $C_{1-4}$alkyl, heterocyclic, or a heterocyclic $C_{1-4}$alkyl moiety, all of which moieties may be optionally substituted.

Suitably $R_1$ is independently selected from hydrogen; halogen; nitro; cyano; halosubstituted $C_{1-10}$ alkyl, such as $CF_3$; $C_{1-10}$ alkyl, such as methyl, ethyl, isopropyl, or n-propyl; $C_{2-10}$ alkenyl; $C_{1-10}$ alkoxy, such as methoxy, or ethoxy; halosubstituted $C_{1-10}$ alkoxy, such as trifluoromethoxy; azide; $(CR_8R_8)_qS(O)_tR_4$, wherein t is 0, 1 or 2; hydroxy; hydroxy $C_{1-4}$alkyl, such as methanol or ethanol; aryl, such as phenyl or naphthyl; aryl $C_{1-4}$ alkyl, such as benzyl; aryloxy, such as phenoxy; aryl $C_{1-4}$ alkyloxy, such as benzyloxy; heteroaryl; heteroarylalkyl; heteroaryl $C_{1-4}$ alkyloxy; aryl $C_{2-10}$ alkenyl; heteroaryl $C_{2-10}$ alkenyl; heterocyclic $C_{2-10}$ alkenyl; $(CR_8R_8)_qNR_4R_5$; $C_{2-10}$ alkenyl $C(O)NR_4R_5$; $(CR_8R_8)_qC(O)NR_4R_5$; $(CR_8R_8)_qC(O)NR_4R_{10}$; $S(O)_3H$; $S(O)_3R_8$; $(CR_8R_8)_qC(O)R_{11}$; $C_{2-10}$ alkenyl $C(O)R_{11}$; $C_{2-10}$ alkenyl $C(O)OR_{11}$; $(CR_8R_8)_qC(O)R_{11}$; $(CR_8R_8)_qC(O)OR_{11}$; $(CR_8R_8)_qOC(O)R_{11}$; $(CR_8R_8)_qNR_4C(O)R_{11}$; $(CR_8R_8)_qC(NR_4)NR_4R_5$; $(CR_8R_8)_qNR_4C(NR_5)R_{11}$; $(CR_8R_8)_qNHS(O)_tR_{13}$; $(CR_8R_8)_qS(O)_tNR_4R_5$. All of the aryl, heteroaryl, and heterocyclic containing moieties may be optionally substituted as defined herein below.

For use herein the term "the aryl, heteroaryl, and heterocyclic containing moieties" refers to both the ring and the alkyl, or if included, the alkenyl rings, such as aryl, arylalkyl, and aryl alkenyl rings. The term "moieties" and "rings" may be interchangeably used throughout.

Suitably, $R_4$ and $R_5$ are independently hydrogen, optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, heterocyclic$C_{1-4}$ alkyl, or $R_4$ and $R_5$ together with the nitrogen to which they are attached form a 5 to 7 member ring which may optionally comprise an additional heteroatom selected from O/N/S.

Suitably, $R_8$ is independently hydrogen or $C_{1-4}$ alkyl.

Suitably, $R_9$ is hydrogen or a $C_{1-4}$ alkyl;

Suitably, q is 0 or an integer having a value of 1 to 10.

Suitably, $R_{10}$ is $C_{1-10}$ alkyl $C(O)_2R_8$, such as $CH_2C(O)_2H$ or $CH_2C(O)_2CH_3$.

Suitably, $R_{11}$ is hydrogen, $C_{1-4}$ alkyl, aryl, aryl $C_{1-4}$ alkyl, heteroaryl, heteroaryl $C_{1-4}$alkyl, heterocyclic, or heterocyclic $C_{1-4}$alkyl.

Suitably, $R_{12}$ is hydrogen, $C_{1-10}$ alkyl, optionally substituted aryl or optionally substituted arylalkyl.

Suitably, $R_{13}$ is $C_{1-4}$alkyl, aryl, arylalkyl, heteroaryl, heteroaryl$C_{1-4}$alkyl, heterocyclic, or heterocyclic$C_{1-4}$alkyl, wherein all of the aryl, heteroaryl and heterocyclic containing moieties may all be optionally substituted.

Suitably, Y is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $(CR_8R_8)_qS(O)_tR_a$; hydroxy; hydroxy$C_{1-4}$alkyl; aryl; aryl $C_{1-4}$ alkyl; aryloxy; aryl$C_{1-4}$ alkyloxy; heteroaryl; heteroarylalkyl; heteroaryl $C_{1-4}$ alkyloxy; heterocyclic, heterocyclic $C_{1-4}$alkyl; aryl $C_{2-10}$ alkenyl; heteroaryl $C_{2-10}$ alkenyl; heterocyclic $C_{2-10}$ alkenyl; $(CR_8R_8)_qNR_4R_5$; $C_{2-10}$ alkenyl $C(O)NR_4R_5$; $(CR_8R_8)_qC(O)NR_4R_5$; $(CR_8R_8)_qC(O)NR_4R_{10}$; $S(O)_3H$; $S(O)_3R_8$; $(CR_8R_8)_qC(O)R_{11}$; $C_{2-10}$ alkenyl $C(O)R_{11}$; $C_{2-10}$ alkenyl $C(O)OR_{11}$; $(CR_8R_8)_qC(O)OR_{12}$; $(CR_8R_8)_qOC(O)R_{11}$; $(CR_8R_8)_qC(NR_4)NR_4R_5$; $(CR_8R_8)_qNR_4C(NR_5)R_{11}$; $(CR_8R_8)_qNR_4C(O)R_{11}$; $(CR_8R_8)_qNHS(O)_tR_{13}$; or $(CR_8R_8)_qS(O)_tNR_4R_5$; or two Y moieties together may form O—$(CH_2)_s$—O or a 5 to 6 membered saturated or unsaturated ring. The aryl, heteroaryl and heterocyclic containing moieties noted above may all be optionally substituted as defined herein.

Suitably s is an integer having a value of 1 to 3.

When Y forms a dioxybridge, s is preferably 1. When Y forms an additional unsaturated ring, it is preferably 6 membered resulting in a naphthylene ring system. These ring systems may be substituted 1 to 3 times by other Y moieties as defined above.

Suitably, $R_a$ is an alkyl, aryl $C_{1-4}$ alkyl, heteroaryl, heteroaryl-$C_{1-4}$alkyl, heterocyclic, or a heterocyclic$C_{1-4}$ alkyl, wherein all of these moieties may all be optionally substituted.

Y is preferably a halogen, $C_{1-4}$ alkoxy, optionally substituted aryl, optionally substituted aryloxy or arylalkoxy, methylene dioxy, $NR_4R_5$, thio $C_{1-4}$alkyl, thioaryl, halosubstituted alkoxy, optionally substituted $C_{1-4}$ alkyl, or hydroxy alkyl. Y is more preferably mono-substituted halogen, disubstituted halogen, mono-substituted alkoxy, disubstituted alkoxy, methylenedioxy, aryl, or alkyl, more preferably these groups are mono or di-substituted in the 2'-position or 2'-, 3'-position.

While Y may be substituted in any of the ring positions, n is preferably one. While both $R_1$ and Y can both be hydrogen, it is preferred that at least one of the rings is substituted, preferably both rings are substituted.

As used herein, "optionally substituted" unless specifically defined shall mean such groups as halogen, such as fluorine; chlorine, bromine or iodine; hydroxy; hydroxy substituted $C_{1-10}$alkyl; $(C_8R_8)_qOR_4$; $C_{1-10}$alkoxy, such as methoxy or ethoxy; two substituents together may form O—$(CH_2)_s$—O; $S(O)_{m'}C_{1-10}$ alkyl, wherein m' is 0, 1 or 2, such as methyl thio, methyl sulfinyl or methyl sulfonyl; amino, mono & di-substituted amino, such as in the $NR_4R_5$ group; $NHC(O)R_4$; $C(O)NR_4R_5$; $C(O)OR_4$; $S(O)_tNR_4R_5$; $NHS(O)_tR_{20}$, $C_{1-10}$ alkyl, such as methyl, ethyl, propyl, isopropyl, or t-butyl; halosubstituted $C_{1-10}$ alkyl, such $CF_3$; an optionally substituted aryl, such as phenyl, or an optionally substituted arylalkyl, such as benzyl or phenethyl, optionally substituted heterocylic, optionally substituted heterocyclicalkyl, optionally substituted heteroaryl, optionally substituted heteroaryl alkyl, wherein these aryl , heteroaryl, or heterocyclic moieties may be substituted one to two times by halogen; hydroxy; hydroxy substituted alkyl; $C_{1-10}$ alkoxy; $S(O)_{m'}C_{1-10}$ alkyl; amino, mono & di-substituted alkyl amino, such as in the $NR_4R_5$ group; $C_{1-10}$ alkyl, or halosubstituted $C_{1-10}$ alkyl, such as $CF_3$.

$R_{20}$ is suitably $C_{1-4}$ alkyl, aryl, aryl $C_{1-4}$alkyl, heteroaryl, heteroaryl$C_{1-4}$alkyl, heterocyclic, or heterocyclic$C_{1-4}$alkyl.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation. Suitable pharmaceutically acceptable cations are well known to those skilled in the art and include alkaline, alkaline earth, ammonium and quaternary ammonium cations.

The following terms, as used herein, refer to:

"halo"—all halogens, that is chloro, fluoro, bromo and iodo.

"$C_{1-10}$alkyl" or "alkyl"—both straight and branched chain moieties of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

"cycloalkyl" is used herein to mean cyclic moiety, preferably of 3 to 8 carbons, including but not limited to cyclopropyl, cyclopentyl, cyclohexyl, and the like.

"alkenyl" is used herein at all occurrences to mean straight or branched chain moiety of 2–10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl;

"heteroaryl" (on its own or in any combination, such as "heteroaryloxy", or "heteroaryl alkyl")—a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, tetrazole, thiazole, thiadiazole, triazole, imidazole, or benzimidazole.

"heterocyclic" (on its own or in any combination, such as "heterocyclicalkyl")—a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydropyran, thiomorpholine, or imidazolidine. Furthermore, sulfur may be optionally oxidized to the sulfone or the sulfoxide.

"arylalkyl" or "heteroarylalkyl" or "heterocyclicalkyl" is used herein to mean $C_{1-10}$ alkyl, as defined above, attached to an aryl, heteroaryl or heterocyclic moiety, as also defined herein, unless otherwise indicated.

"sulfinyl"—the oxide S(O) of the corresponding sulfide, the term "thio" refers to the sulfide, and the term "sulfonyl" refers to the fully oxidized $S(O)_2$ moiety.

"wherein two $R_1$ moieties (or two Y moieties) may together form a 5 or 6 membered saturated or unsaturated ring" is used herein to mean the formation of an aromatic ring system, such as naphthalene, or is a phenyl moiety having attached a 6 membered partially saturated or unsaturated ring such as a $C_6$ cycloalkenyl, i.e. hexene, or a $C_5$ cycloalkenyl moiety, such as cyclopentene.

Illustrative compounds of Formula (I) include:

N-(2-bromophenyl)-N'-[4-chloro-2-hydroxy-3-(N",N"dimethylaminosulfonyl)phenyl]cyanoguanidine;

N-[4chloro-2-hydroxy-3-(N",N"-dimethylaminosulfonyl)phenyl]-N'-(2,3-dichlorophenyl)cyanoguanidine;

N-(2-bromophenyl)-N'-[4-chloro2-hydroxy-3-[S-(+)-(2-methoxymethyl)pyrrolidin-1-yl]aminosulfonylphenyl]cyanoguanidine;

N-(2,3-dichlorophenyl)-N'-[4-chloro-2-hydroxy-3-[S-(+)-(2-methoxymethyl)pyrrolidin-1-yl]aminosulfonylphenyl]cyanoguanidine;

N-phenyl-N'-[4-chloro-2-hydroxy-3-[S-(+)-(2-methoxymethyl)pyrrolidin-1-yl[aminosulfonylphenyl]cyanoguanidine;

N-(2-bromophenyl)-N'-[4chloro-2-hydroxy-3-[R-(2-methoxymethyl)pyrrolidin-1-yl]aminosulfonylphenyl]cyanoguanidine;

N-(2,3-dichlorophenyl)-N'-[4chloro-2-hydroxy-3-[R-(2-methoxymethyl)pyrrolidin-1-yl]aminosulfonylphenyl]cyanoguanidine;

N-(2-bromophenyl)-N'-[4-chloro-2-hydroxy-3-(N"-isoxazolidinylaminosulfonylphenyl]cyanoguanidine;

N-(2,3-dichlorophenyl)-N'-[4-chloro-2-hydroxy-3-(N"-isoxazolidinylaminosulfonylphenyl]cyanoguanidine;

N-(2-bromophenyl)-N'-[4-chloro-2-hydroxy-3-(N"-tetrahydroisoxazylaminosulfonyl)phenyl]cyanoguanidine;

N-(2,3-dichlorophenyl)-N'-[4-chloro-2-hydroxy-3-(N"-tetrahydroisoxazylaminosulfonyl)phenyl]cyanoguanidine;

N-(2,3-dichlorophenyl)-N'-[4-chloro-2-hydroxy-3-(4-thiomorpholinylaminosulfonyl)phenyl]cyanoguanidine;

N-[4-chloro-2-hydroxy-3-[N",N"-dimethylaminosulfonyl]phenyl]-N'-(2-bromophenyl)propylguanidine;

N-(2-bromophenyl)-N'-[4-chloro-2-hydroxy-3-(4-oxidothiomorpholino)amino sulfonylphenyl]cyanoguanidine;

N-(2,3-chlorophenyl)-N'-[4-chloro-2-hydroxy-3-(4-oxidothiomorpholino)amino sulfonylphenyl]cyanoguanidine;

N-(2-bromophenyl)-N'-[4-chloro-2-hydroxy-3-(N"-methylpiperazino)amino sulfonylphenyl]cyanoguanidine;

N-(2,3-dichlorophenyl)-N'-[4-chloro-2-hydroxy-3(N"-methylpiperazino)amino sulfonylphenyl]cyanoguanidine;

N-(2-bromophenyl)-N'-[4-chloro-2-hydroxy-3-(N"-ethylmorpholino)amino sulfonylphenyl]cyanoguanidine;

N-(2,3-dichlorophenyl)-N'-[4-chloro-2-hydroxy-3-(N"-ethylmorpholino)amino sulfonylphenyl]cyanoguanidine;

N-(2-bromophenyl)-N'-{4-chloro-2-hydroxy-3-[N"-ethyl-2-(2-ethylpyrrolidino)]amino sulfonylpheny}cyanoguanidine;

N-(2,3dichlorophenyl)-N'-{4-chloro-2-hydroxy-3-[N"-ethyl-2-(2-ethylpyrrolidino)]amino sulfonylpheny)cyanoguanidine;

N-(2-bromophenyl)-N'-{4-chloro-2-hydroxy-3-[S-(+)-(2-carboxy)pyrrolidin-1-yl]amino sulfonylpheny}cyanoguanidine;

N-(2,3-dichlorophenyl)-N'-(4-chloro-2-hydroxy-3-[S-(+)-(2-carboxy)pyrrolidin-1-yl]amino sulfonylpheny}cyanoguanidine;

N-(2-bromo-3-fluorophenyl)-N'-[4-chloro-2-hydroxy-3-[S-(+)-(2-methoxymethyl)pyrrolidin-1-yl]sulfonylphenyl]cyanoguanidine;

N-(2-phenoxyphenyl)-N'-[4-chloro-2-hydroxy-3-[S-(+)-(2-methoxymethyl)pyrrolidin-1-yl]sulfonylphenyl]cyanoguanidine; and N-(2-benzoxyphenyl)-N'-[4-chloro-2-hydroxy-3-[S-(+)-(2-methoxymethyl)pyrrolidin-1-yl]sulfonylphenyl]cyanoguanidine;

or a pharmaceutically acceptable salt thereof.

METHODS OF PREPARATION

The compounds of Formulas (I) may be obtained by applying synthetic procedures, some of which are illustrated in the Schemes below.

Scheme 1

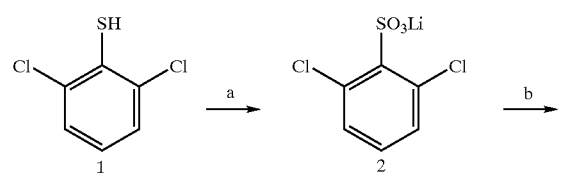

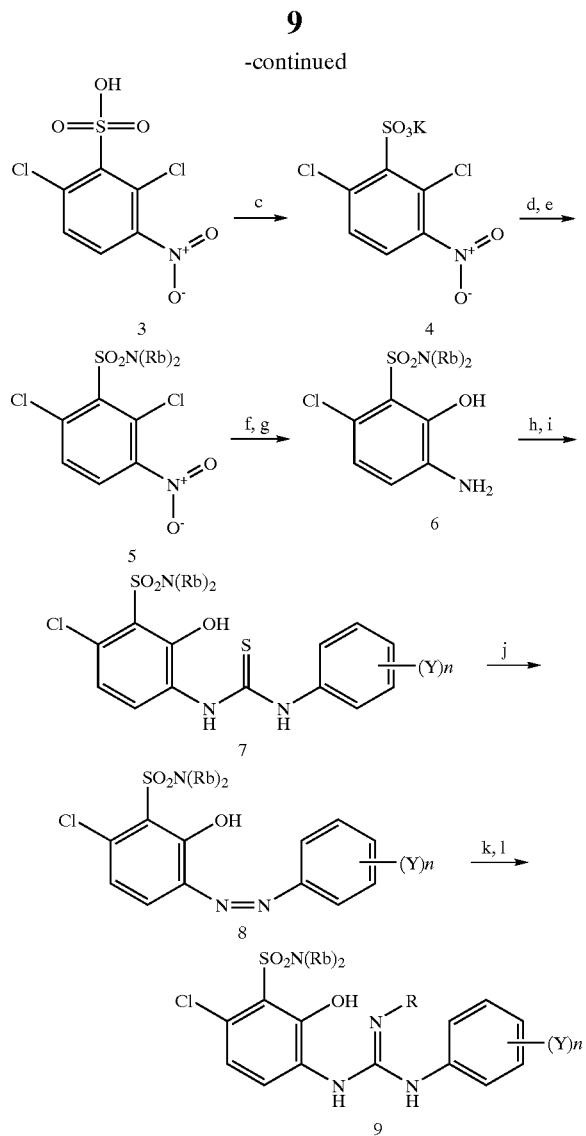

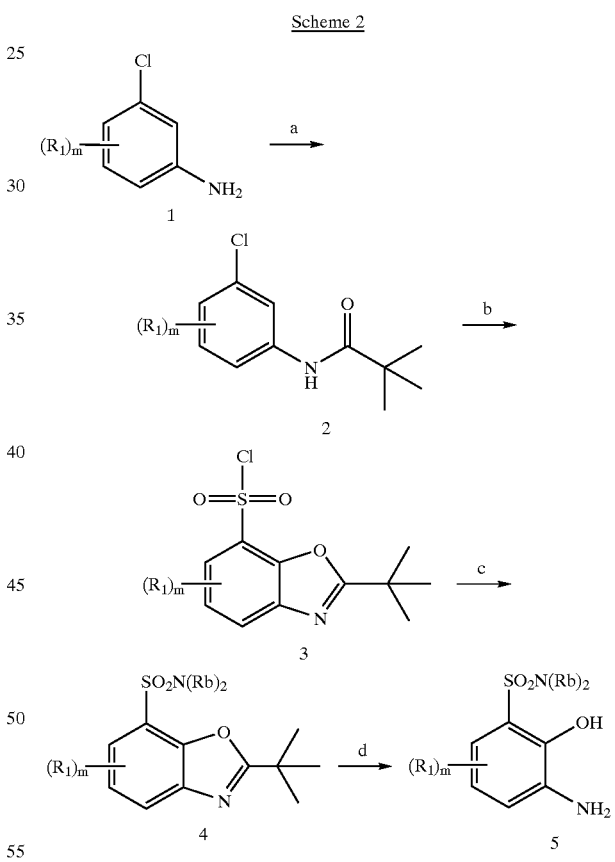

converted to the sulfonyl chloride using PCl$_5$ with POCl$_3$ as a solvent. The sulfonyl chloride can then be converted to the corresponding sulfonamide using the desired amine HNR'R" in triethyl amine at temperatures ranging from −78° C. to 25° C. to form the corresponding sulfonamide 5-scheme 1.

The chlorine ortho to the nitro group can be selectively hydrolyzed using sodium hydride/water in THF at room temperature to form the phenol. The nitro can be reduced by conditions well known in the art such as hydrogen and palladium on carbon to form the corresponding aniline 6scheme 1. The aniline can then be coupled with a commercially available thioisocyanate to form the desired thiourea.

The phenol in thiourea can be protected with TBSCl to form the corresponding compounds 7-scheme 1. The protected thiourea can be converted to the corresponding carbodiimide 8-scheme 1 using methanesulfonyl chloride and triethyl amine at 0° C. The carbodiimde can then be converted to the corresponding protected cyanoguanidine using cyanamide and Hunig's base, followed by desilylation with CsF or TBAF to form the desired the cyanoguanidine 9-scheme1.

Scheme 2 a) PivCl, TEA; b) i. BuLi, THF, -40° C.; ii. SO$_2$; iii. SO$_2$Cl$_2$; c) HN(R$_b$)$_2$, TEA; d) H$_2$SO$_4$, H$_2$O.

Scheme 1
a) i) NCS, AcOH, H$_2$O, ii) LiOH, MeOH b) H$_2$SO$_4$, HNO$_3$ c) KOH, MeOH d) PCl$_5$,POCl$_3$ e) NR'R"H, Et$_3$N f) NaH, H$_2$O g) Pd/C, H$_2$ h)RCNO, DMF i) TBSCl, Imidazole j) MsCl, Et$_3$N k) NH$_2$CN, Hunig's base 1) CsF/TBAF, MeOH/ THF The desired 4-chloro-N-(3-sulfonamido-2-hydroxyphenyl)-N"-phenyl cyanoguanidine can be synthesized from the commercially available 2,6-dichloro thiophenol using procedure elaborated in scheme 1. The thiol can be oxidized to the sulfonyl halide using a halogenating agent such as NCS, NBS, chlorine or bromine in the presence of a protic solvent such as alcohol, acetic acid or water. The sulfonyl halide can be hydrolyzed by using a metal hydroxide such as lithium or potassium hydroxide to form the corresponding sulfonic acid salt.

The sulfonic acid salt can then be nitrated under nitration conditions such as nitric acid in a solvent of strong acid such as sulfuric acid to form the nitro phenyl sulfonic acid 3-scheme 1. The sulfonic acid 3-scheme 1 can be converted to the sulfonamide 5-scheme 1 using a three step procedure involving the formation of the metal salt using a base such as potassium hydroxide, sodium hydride or sodium carbonate to form 4-scheme 1. The sulfonic acid salt is then If the desired hydroxyaniline 6-Scheme 1 is not commercially available, it can be prepared as outlined in Scheme 2: Commercially available substituted 3-chloroanilines 1-scheme-2 can be converted to the amide 2-scheme-2 using standard conditions well known in the art such as pivavolyl chloride and triethylamine in a suitable organic solvent such as methylene chloride. The amide 2-scheme-2 can be converted to the benzoxazole 3-scheme-2 using an excess amount of a strong base such as butyllithium in a suitable organic solvent such as THF under reduced reaction temperatures (-20 to -40° C.) followed by quenching the reaction with sulfur dioxide gas and converting resulting sulfinic acid salt to the sulfonyl chloride 3-scheme-2 using standard conditions well known in the art such as sulfuryl chloride in a suitable organic solvent such as methylene chloride. The sulfonyl chloride 3-scheme-2 can be transformed to the sulfonamide 4-scheme-2 using standard conditions well known in the art by reacting it with the amine $HN(R_b)_2$ in the presence of a suitable amine base such as triethylamine in a suitable organic solvent such as methylene chloride. The desired phenolaniline 5 can be obtained from the benzoxazole 4scheme-2 using standard hydrolysis conditions well known in the art such as suilfric acid in water and heating at 85° C.

SYNTHETIC EXAMPLES

The invention will now be described by reference to the following examples, which are merely illustrative and are not to be construed as a limitation of the scope of the present invention. All temperatures are given in degrees centigrade, all solvents are highest available purity and all reactions run under anhydrous conditions in an argon atmosphere unless otherwise indicated.

In the Examples, all temperatures are in degrees Centigrade (°C.). Mass spectra were performed upon a VG Zab mass spectrometer using fast atom bombardment, unless otherwise indicated. $^1$H-NMR (hereinafter "NMR") spectra were recorded at 250 MHz using a Bruker AM 250 or Am 400 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant.

Examples 1 & 2

Preparation of N-[4-Chloro-2-hydroxy-3-(N",N"-dimethylaminosulfonyl)phenyl]-N'-(2,3-dichlorophenyl)cyanoguanidine and N-(2-Bromophenyl)-N'-[4-chloro-2-hydroxy-3-(N",N"-dimethylaminosulfonyl)phenyl]cyanoguanidine 2,6-Dichloro-3-nitrobenzenesulfonic Acid Lithium hydroxide hydrate (8.96 g, 0.214 mol) was added to a solution of 2,6-dichlorobenzenesulfonyl chloride (35 g, 0.146 mol) in MeOH (300 mL) and the reaction was allowed to stir at room temperature for 16 hr. The reaction mixture was filtered to remove suspended solids and then concentrated. The resulting solid was dried in vacuo overnight to remove any residual MeOH. The solid was then dissolved in $H_2SO_4$ (300 mL) and chilled in an ice bath. A solution of $H_2SO_4$ (35 mL) and $HNO_3$ (70%, 10.7 mL) was slowly added to the above reaction over 90 min. The reaction was allowed to warm up to room temperature overnight and then slowly poured into ice water (1200 mL) and extracted with EtOAc. The combined organic layers were dried ($MgSO_4$) and concentrated to yield 2,6-dichloro-3-nitrobenzenesulfonic acid (37.38 g, 96%) as the dihydrate. EI-MS (m/z) 270 (M$^-$).

2,6-Dichloro-3-nitrobenzenesulfonyl Chloride

Potassium hydroxide (11.54 g, 0.206 mol) was added to a solution of 2,6-dichloro-3-nitrobenzenesulfonic acid dihydrate (37.38 g, 0.137 mol) in MeOH (500 mL) and the reaction was allowed to stir at room temperature for 14 hr. The reaction mixture was concentrated and the resulting solid was dried in vacuo overnight. To this was added $PCl_5$ (29.60 g, 0.142 mol) followed by $POCl_3$ (400 mL) and the mixture was refluxed overnight. The reaction was then cooled to room temperature and concentrated. The resulting mixture was taken up in EtOAc and chilled in an ice bath. Ice chunks were slowly added to the reaction mixture to quench any leftover $PCl_5$. When bubbling ceased, water was added and the reaction mix was extracted with EtOAc. The organic layer was dried ($MgSO_4$) and concentrated to yield 2,6-Dichloro-3-nitrobenzenesulfonyl chloride (31.4 g, 79%).

$^1$H NMR (DMSO-d$_6$) δ 7.88 (d, 1H), 7.75 (d, 1H).

The following is the general procedure for sulfonamide formation:

N,N-Dimethyl-2,6-dichloro-3-nitrobenzenesulfonamide

Into a solution of 2,6-dichloro-3-nitrobenzenesulfonyl chloride (200 mg, 0.69 mmol) in 15 mL of dichloromethane at -78° C. was added dropwise a solution of dimethylamine (2.0 M in MeOH, 0.345 mL, 0.69 mmol) and triethylamine (0.14 mL, 1.04 mmol) in 10 mL of dichloromethane. The mixture was warmed to room temperature and stirred for 16 hours. The mixture was acidified to pH>1 with 1N aq. HCl, then extracted with ethyl acetate. The combined organic layer was then concentrated to give the crude material. Column chromatography on silica gel, eluting with ethyl acetate/hexane (30/70, v/v/), gave the desired (240 mg, 70%). EI-MS (m/z) 298 (M$^-$).

The following is the general procedure for the hydrolysis of dichlorosulfonamide to phenol:

N,N-Dimethyl-6chloro-2-hydroxy-3-nitrobenzenesulfonamide

A mixture of N,N-dimethyl-2,6-dichloro-3-nitrobenzenesulfonamide (2.64 g, 8.83 mmol), 60% sodium hydride (1.06 g, 26.5 mmol) and water (191 mg, 10.6 mmol) was heated to 35° C. while kept under argon atmosphere for 16 hours. The solvent was evaporated. when The reaction was almost complete as indicated by $^1$H NMR. The residue was diluted with ethyl acetate and washed with 1N aq. HCl. The solvent was concentrated to give the crude material. Column chromatography on silica gel, eluting with ethyl acetate/hexane/acetic acid (40/58/2, v/v/v), gave the desired product (2.3 g, 93%). EI-MS (m/z)279.5 (M$^-$).

The following is the general procedure for the hydrogenation of nitro compound to aniline:

N,N-Dimethyl-3-amino-6-chloro-2-hydroxybenzenesulfonamide

To a solution of N,N-dimethyl-6-chloro-2-hydroxy-3-nitrobenzenesulfonamide (2.3 g, 8.2 mmol) in ethyl acetate, was added 10% Pd/C (2.0 g). The mixture was flushed with argon, and then stirred under a hydrogen atmosphere at balloon pressure for 3 hours at room temperature. The mixture was filtered through celite and the celite was washed with methanol. The solvent was evaporated to give the desired product (2.0 g, 97%). EI-MS (m/z) 249.5 (M$^-$).

Preparation of N-(3,4-Dichlorophenyl)2,2-dimethyl-propionamide 3,4-dichloroaniline (150 g) in TBME (1 L) was cooled to 10–15° C. 30% aq NaOH (141 g, 1.14 equiv) was added, and the solution stirred vigorously via overhead mechanical stirrer. Trimethylacetyl chloride ("PivCl", 126 mL) was added at such a rate as to keep the internal temperature below 30° C. During this addition, the solution mixture becomes thick with white solid product. When the addition was complete (10–15 min), the mixture was heated to 30–35° C. for 1 hr, and then allowed to cool. The reaction mixture was held at -5° C. (overnight), and then filtered, rinsing first with 90:10 water/MeOH (600 mL) and then water (900 mL). Drying under vacuum yielded 195 g (86%) product, as off-white crystals. LCMS m/z 246(M−H)+.

Preparation of 2-tert-Butyl-6-chloro-benzooxazole-7-sulfonyl Chloride

The solution of N-(3,4dichloro-phenyl)2,2-dimethyl-propionamide (10 g, 41 mmol) in dry THF (100 mL) was cooled to −72° C. under argon. n-Butyl lithium (1.6M in hexane, 64 mL, 102 mmol) was added dropwise. The solution warmed to ca −50° C. over 45 minutes, and then was kept in the −25—−10° C. range for 2 hrs. The solution was then recooled to −78° C., and sulfur dioxide was bubbled through the solution for 30 min. The solution was then allowed to warm to room temperature for 2 h, and a Ar stream was bubbled through the solution, with a gas outlet provided so that any excess sulfur dioxide could escape during the warming. The THF solution was cooled in an ice bath, and sulfuryl chloride (3.58 mL, 44.9 mmol) was added dropwise. After a few minutes, the solution was warmed to room temperature for overnight. The mixture was concentrated, diluted with ethyl acetate and washed with water. Decolorizing carbon was added and the mixture was filtered. The resulting solution was dried (sodium sulfate), filtered and concentrated to afford the title compound (12.4 g, 98%). $^1$H NMR (CDCl$_3$) • 7.92 (d, 1H, J=8.5 Hz), 7.57 (d, 1H, J=8.4 Hz), 1.57 (s, 9H).

General Procedure for the Synthesis of 7-Sulfoamidebenzoxazoles 2-tert-Butyl-6-chloro-7-(4-methyl-piperazine-1-sulfonyl)-benzooxazole To a solution of 2-tert-butyl-6-chloro-benzooxazole-7-sulfonyl chloride (2.69 g, 8.73 mmol) and triethylamine (2.44 mL, 17.5 mmol) in THF (60 mL) at 0° C. was added 1-methylpiperazine (0.98 mL, 8.83 mmol). The reaction was warmed to room temperature and allowed to stir overnight. The solution was concentrated and then diluted with water and extacted with ethyl acetate (3 times). The combined organic layers were dried with MgSO$_4$, filtered, and concentrated. Flash chromatography (80% ethyl acetate/20% Ethanol) on silica gel gave the title compound (2.45 g, 76%). EI-MS m/z 372(M+H)+.

General Procedure for the Hydrolysis of the Benzooxazole to the Desired Aniline

6-Amino-3-chloro-2-(4-methyl-piperazine-1-sulfonyl)-phenol

To a solution of 2-tert-Butyl-6-chloro-7-(4-methyl-piperazine-1-sulfonyl)-benzooxazole (2.44 g, 6.56 mmol) in 1,4-dioxane (20 mL) was treated with water (4 mL) and conc. H$_2$SO$_4$ (4 mL). The mixture was heated to 85° C. for 14 h. The reaction was cooled to room temperature, and then basified to pH=14 with 25% aq NaOH. washed. The mixture was extracted with ethyl acetate (3 times), dried with MgSO$_4$, filtered, and concentrated to afford the title compound (1.35 g, 68%). EI-MS m/z 306(M+H)+.

The following is the general procedure for thiourea formation:

N-[4-Chloro-2-hydroxy-3[N",N"-dimethylaminosulfonyl] phenyl]-N'-(2,3-dichlorophenyl)thiourea A solution of N,N-dimethyl-3-amino-6-chloro-2-hydroxybenzenesulfonamide (356 mg, 1.42 mmol) and 2,3-dichlorophenylisothiocyanate (318 mg, 1.57 mmol) in 1.0 mL of N,N-dimethylformamide was stirred at room temperature for 3 hours. Purification by column chromatography on silica gel, eluting with ethyl acetate/hexane (30/70, v/v) to give the desired product (440 mg, 68%). EI-MS (m/z) 455.5 (M+).

N-[4-Chloro-2-hydroxy-3-[N",N"-dimethylaminosulfonyl] phenyl]-N'-(2-bromophenyl)thiourea A solution of N,N-dimethyl-3-amino-6-chloro-2-hydroxybenzenesulfonamide (50 mg, 0.2 mmol) and 2-bromophenylisothiocyanate (43 mg, 0.2 mmol) in 0.5 mL of N,N-dimethylformamide was stirred at room temperature for 3 hours. Purification by column chromatography on silica gel, eluting with ethyl acetate/hexane (30/70, v/v) to give the desired product (66 mg, 74%). EI-MS (m/z) 465.5 (M+).

The following is the general procedure for protected phenyl thiourea formation:

N-[4-Chloro-2-tert-butyldimethylsilyloxy-3-(N",N"-dimethylaminosulfonyl)phenyl]-N'-(2-bromophenyl) thiourea To a solution of N-[4-chloro-2-hydroxy-3-(N",N"-dimethylaminosulfonyl)phenyl]-N'-(2-bromophenyl) thiourea (500 mg, 1.07 mmol) in THF (20 mL), tert-butyldimethylsilyl chloride (810 mg, 5.35 mmol) and imidazole (144 mg, 2.14 mmol) were added. The reaction mixture was stirred at room temperature for 16 hours. Then it was partitioned between ethyl acetate and water. The combined organic phase was dried and concentrated. Chromatography of the residue on silica gel (30% Ethyl acetate/Hexane) gave desired product (240 mg, 40%) and recovered starting material (280 mg). EI-MS m/z 580 (M+).

N-[4-Chloro2-tert-butyldimethylsilyloxy-3-(N",N"-dimethylaminosulfonyl)phenyl]-N'-(2,3-dichlorophenyl) thiourea To a solution of N-[4-chloro-2-hydroxy-3-(N",N"-dimethylaminosulfonyl)phenyl]-N'-(2,3dichlorophenyl) thiourea (440 mg, 1.07 mmol) in THF (20 mL), tert-butyldimethylsilyl chloride (730 mg, 4.85 mmol) and imidazole (132 mg, 1.94 mmol) were added. The reaction mixture was stirred at room temperature for 16 hours. Then it was partitioned between ethyl acetate and water. The combined organic phase was dried and concentrated. Chromatography of the residue on silica gel (30% Ethyl acetate/Hexane) gave desired product (270 mg, 50%). EI-MS m/z 570 (M+).

The following is the general procedure for carbodiimide formation:

N-[4-Chloro-2-tert-butyldimethylsilyloxy-3-(N",N"-dimethylaninosulfonyl)phenyl]-N'-(2-bromophenyl) carbodiimide To a solution of N-[4-chloro-2-tert-butyldimethylsilyloxy-3-(N",N"-dimethylaminosulfonyl) phenyl]-N'-(2-bromophenyl)thiourea (240 mg, 0.42 mmol) in dichloromethane (10 mL) at 0° C., methanesulfonyl chloride (0.065 mL, 0.84 mmol) and triethylamine (0.12 mL, 0.84 mmol) were added. 4-Dimethylaminopyridine was added as a catalyst. The reaction mixture was stirred at 0° C. for 1 hour, then it was partitioned between dichloromethane and water. The combined organic phase was dried and concentrated to give the desired product (266.2 mg, crude). $^1$H NMR (CDCl$_3$) δ 0.4 (s, 6H), 1.09 (s, 9H), 2.86 (s, 6H), 7.06 (d, 2H), 7.1–7.37 (m, 4H).

N-[4-Chloro-2-tert-butyldimethylsilyloxy-3-(N",N"-dimethylaminosulfonyl)phenyl]-N'-(2,3-dichlorophenyl) carbodiimide To a solution of N-[4-chloro-2-tert-butyldimethylsilyloxy-3-(N",N"-dimethylaminosulfonyl) phenyl]-N'-(2,3-dichlorophenyl)thiourea (270 mg, 0.45 mmol) in dichloromethane (10 mL) at 0° C., methanesulfonyl chloride (0.07 mL, 0.9 mmol) and triethylamine (0.13 mL, 0.9 mmol) were added. 4-Dimethylaminopyridine was added as a catalyst. The reaction mixture was stirred at 0° C.

for 1 hour, then it was partitioned between dichloromethane and water. The combined organic phase was dried and concentrated to give the desired product (270 mg, crude). $^1$H NMR (CDCl$_3$) δ 0.47 (s, 6H), 1.05 (s, 9H), 2.9 (s, 6H), 7.08 (d, 1H), 7.12 (d, 1H), 7.2 (t, 1H), 7.31 (m, 2H).

The following is the general procedure for cyanoguanidine formation:

N-[4-Chloro-2-hydroxy-3-(N'',N''-dimethylaminosulfonyl) phenyl]-N'-(2-bromophenyl)cyanoguanidine To a solution of N-[4-chloro-2-tert-butyldimethylsilyloxy-3-(N'',N''-dimethylaminosulfonyl) phenyl]-N'-(2-bromophenyl)carbodiimide (266 mg, 0.49 mmol) in acetonitrile (5 mL) at room temperature, cyanamide (83 mg, 1.96 mmol) and N,N-diisopropylethylamine (76 mg, 0.59 mmol) was added. The reaction mixture was stirred at room temperature for 1 hour. The reaction mixture was concentrated under reduced pressure. The residue was diluted with a mixture of THF (3 mL) and methanol (1 mL). Cesium fluoride (90 mg, 0.59 mmol) was added at 0° C. The reaction mixture was stirred at 0° C. for 3 hours. The reaction mixture was concentrated under reduced pressure. The residue was purified by Gilson HPLC to give the desired product (70 mg, 30%). EI-MS m/z 473.75(M$^+$).

N-[4-Chloro-2-hydroxy-3-[N'',N''-dimethylaminosulfonyl] phenyl]-N'-(2,3-dichlorophenyl)cyanoguanidine To a solution of N-[4-chloro-2-tert-butyldimethylsilyloxy-3-(N'',N''-dimethylaminosulfonyl) phenyl]-N'-(2,3dichlorophenyl)carbodiimide (270 mg, 0.47 mmol) in acetonitrile (5 mL) at room temperature, cyanamide (79 mg, 1.88 mmol) and N,N-diisopropylethylamine (76 mg, 0.56 mmol) was added. The reaction mixture was stirred at room temperature for 1 hour. The reaction mixture was concentrated under reduced pressure. The residue was diluted with a mixture of tetrahydrofuran (3 mL) and methanol (1 mL). Cesium fluoride (86 mg, 0.56 mmol) was added at 0° C. The reaction mixture was stirred at 0° C. for 3 hours. The reaction mixture was concentrated under reduced pressure. The residue was purified by Gilson HPLC to give the desired product (98 mg, 48%). EI-MS m/z 473.75(M$^+$).

Examples 3, 4 & 5

Preparation of N-(2-Bromophenyl)-N'-[4-chloro-2-hydroxy-3-[S-(+)-(2-methoxymethyl)pyrrolidin-1-yl] aminosulfonylphenyl]cyanoguanidine, N-(2,3-Dichlorophenyl)-N'-[4-chloro-2-hydroxy-3-[S-(+)-(2-methoxymethyl)pyrrolidin-1-yl] aminosulfonylphenyl]cyanoguanidine and N-(2-Bromophenyl)-N'-[4-chloro-2-hydroxy-3-[S-(+)-(2-methoxymethyl)pyrrolidin-1-yl] aminosulfonylphenyl]cyanoguanidine S-(+)-N-(2-Methoxymethyl)pyrrolidin-1-yl-2,6-dichloro-3-nitrobenzenesulfonamide Following the general procedure for sulfonamide formation outlined in example 1, 6-dichloro-3-nitrobenzenesulfonyl chloride (1.0 g, 3.44 mmol), (S)-(+)-2(methyoxymethyl)pyrrolidine (0.476 mL, 4.13 mmol) and triethylamine (0.72 mL, 5.16 mmol) were reacted to form the desired product (1.15 g, 91%). EI-MS m/z 368 (M$^-$).

S-(+)-N-(2-Methoxymethyl)pyrrolidin-1-yl-6-chloro-2-hydroxy-3-nitrobenzenesulfonamide Following the general hydrolysis procedure outlined in example 1, S-(+)-N-(2-methoxymethyl)pyrrolidin-1-yl-2,6-dichloro-3-nitrobenzenesulfonamide (1.15 g, 3.12 mmol), 60% sodium hydride (374 mg, 9.36 mmol) and water (73 mg, 4.02 mmol) were reacted to form the desired product (1.0 g, 91%). EI-MS m/z 349.1 (M$^-$).

S-(+)-N-(2-Methoxymethyl)pyrrolidin-1-yl-3-amino-6-chloro-2-hydroxybenzenesulfonamide Following the general hydrogenation procedure outlined in example 1, S-(+)-N-(2-methoxymethyl)pyrrolidin-1-yl-6-chloro-2-hydroxy-3-nitrobenzenesulfonamide (1.0 g, 2.86 mmol) was reduced with hydrogen and Pd/C (600 mg) to form the desired product (0.9 g, 98%). EI-MS m/z 319.1 (M$^-$).

N-(2-Bromophenyl)-N'-4-chloro-2-hydroxy-3-[S-(+)-(2-methoxymethyl)pyrrolidin-1-yl]aminosulfonylphenyl] thiourea Following the general procedure for thiourea formation outlined in example 1, S-(+N-(2-methoxymethyl)pyrrolidin-1-yl-3-amino-6-chloro-2-hydroxybenzenesulfonamide (260 mg, 0.85 mmol) and 2-bromophenylisothiocyanate (182 mg, 0.85 mmol) were coupled to form the desired thiourea (231 mg, 53%). EI-MS m/z 535.1 (M$^+$).

N-(2,3-Dichlorophenyl)-N'-[4-chloro-2-hydroxy-3-[S-(+)-(2-methoxymethyl)pyrrolidin-1-yl]aminosulfonylphenyl] thiourea Following the general procedure for thiourea formation outlined in example 1, S-(+)-N-(2-methoxymethyl) pyrrolidin-1-yl-3-amino-6chloro-2-hydroxybenzene- sulfonamide (407 mg, 1.27 mmol) and 2,3-dichlorophenylisothiocyanate (285 mg, 1.4 mmol) were coupled to form the desired thiourea (370 mg, 54%). EI-MS m/z 525.1 (M$^+$).

N-Phenyl-N'-[4-chloro-2-hydroxy-3-[S-(+)-(2-methoxymethyl)pyrrolidin-1-yl]aminosulfonylphenyl] thiourea Following the general procedure for thiourea formation outlined in example 1, S-(+)-N-(2-methoxymethyl) pyrrolidin-1-yl-3-amino-6-chloro-2-hydroxybenzenesulfonamide (310 mg, 0.97 mmol) and phenylisothiocyanate (144 mg, 1.07 mmol) were coupled to form the desired thiourea (210 mg, 54%). EI-MS m/z 456 (M$^+$).

N-(2-Bromophenyl)-N'-[4-chloro-2-tert-butyldimethylsilyloxy-3-[S-(+)-2-methoxymethyl)pyrrolidin-1-yl] aminosulfonylphenyl]thiourea Following the general procedure for protected phenyl thiourea formation outlined in example 1, N-(2-bromophenyl)-N'-[4-chloro-2-hydroxy-3-[S-(+)-(2-methoxymethyl)pyrrolidin-1-yl]aminosulfonylphenyl] thiourea (230 mg, 0.44 mmol), tert-butyldimethylsilyl chloride (332 mg, 2.2 mmol) and imidazole (60 mg, 0.88 mmol) were reacted to form the desired product (136 mg, 48%). EI-MS m/z 650 (M$^+$).

N-(2,3-Dichlorophenyl)-N'-[4-chloro-2-tert-butyldimethylsilyloxy-3-[S-(+)-(2-methoxymethyl) pyrrolidin-1-yl]aminosulfonylphenyl]thiourea Following the general procedure for protected phenyl thiourea formation outlined in example 1, N-(2,3-dichlorophenyl)-N'-[4-chloro-2-hydroxy-3-[S-(+)-(2-methoxymethyl)pyrrolidin-1-yl]aminosulfonylphenyl] thiourea (370 mg, 0.71 mmol), tert-butyldimethylsilyl chloride (370 mg, 0.71 mmol) and imidazole (97 mg, 1.42 mmol) were reacted to form the desired product (187 mg, 41%). EI-MS m/z 640.2(M$^+$).

N-Phenyl-N'-[4-chloro-2-tert-Butyldimethylsilyloxy-3-[S-(+)-(2-methoxymethyl)pyrrolidin-1-yl]amino-sulfonylphenyl]thiourea Following the general procedure for protected phenyl thiourea formation outlined in example 1, N-phenyl-N'-4-chloro-2-hydroxy-3-[S-(+)-(2-methoxymethyl)pyrrolidin-1-yl]aminosulfonylphenyl]thiourea (210 mg, 0.46 mmol), tert-butyldimethylsilyl chloride (349 mg, 2.3 mmol) and imidazole (63 mg, 0.92 mmol) were reacted to form the desired product (125 mg, 41%). EI-MS m/z 571 (M$^+$).

N-(2-Bromophenyl)-N'-[4-chloro-2-tert-butyldimethyl-silyloxy-3-[S-(+)-(2-methoxymethyl)pyrrolidin-1-yl]aminosulfonylphenyl]carbodiimide Following the general procedure for carbodiimide formation outlined in example 1, N-(2-bromophenyl)-N'-[4-chloro-2-tert-butyldimethylsilyloxy-3-[S-(+)-(2-methoxymethyl)pyrrolidin-1-yl]aminosulfonylphenyl]thiourea (136 mg, 0.21 mmol), methanesulfonyl chloride (0.03 mL, 0.42 mmol) and triethylamine (0.06 mL, 0.42 mmol) were reacted to form the desired product (120 mg, 93%). $^1$H NMR (CDCl$_3$) δ 0.37 (s, 6H), 1.01 (s, 9H), 1.72 (m, 4H), 3.25 (s, 3H), 3.3 (m, 2H), 3.45 (m, 2H), 4.15 (m, 1H), 7.10 (d, 2H), 7.2 (d, 1H), 7.3 (m, 1H), 7.39 (d, 1H), 7.6 (d, 1H).

N-(2,3-Dichlorophenyl)-N'-[4-chloro-2-tert-butyldimethylsilyloxy-3-[S-(+)-(2-methoxymethyl)pyrrolidin-1-yl]aminosulfonylphenyl]carbodiimide Following the general procedure for carbodiimide formation outlined in example 1, N-(2,3-dichlorophenyl)-N'-[4-chloro-2-tert-butyldimethylsilyloxy-3-[S-(+)-(2-methoxymethyl)pyrrolidin-1-yl]aminosulfonylphenyl]thiourea (187 mg, 0.3 mmol), methanesulfonyl chloride (0.05 ml, 0.6 mmol) and triethylamine (0.08 mL, 0.6 mmol) were reacted to form the desired product (160 mg, 90%). $^1$H NMR (CDCl$_3$) δ 0.32 (s, 6H), 1.01 (s, 9H), 1.35 (m, 4H), 3.24 (s, 3H), 3.42 (m, 4H), 4.14 (m, 1H), 7.10 (d, 1H), 7.12 (d, 1H), 7.2 (t, 1H), 7.29 (d, 1H), 7.32(d, 1H).

N-Phenyl-N'-[4-chloro-2-tert-butyldimethylsilyloxy-3-[S-(+)-(2-methoxymethyl)pyrrolidin-1-yl]aminosulfonylphenyl]carbodiimide Following the general procedure for carbodiimide formation outlined in example 1, N-phenyl-N'-[4-chloro-2-tert-butyldimethylsilyloxy-3-[S-(+)-(2-methoxymethyl)pyrrolidin-1-yl]aminosulfonylphenyl]thiourea (125 mg, 0.22 mmol), methanesulfonyl chloride (0.04 mL, 0.44 mmol) and triethylamine (0.06 mL, 0.44 mmol) were reacted to form the desired product (125 mg, crude). $^1$H NMR (CDCl$_3$) δ 0.37 (s, 6H), 1.04 (s, 9H), 1.35 (m, 4H), 3.24 (s, 3H), 3.42 (m, 4H), 4.14 (m, 1H), 7.06 (d, 1H), 7.16 (d, 1H), 7.19 (m, 2H), 7.25 (d, 1H), 7.35 (t, 2H).

N-(2-Bromophenyl)-N'-[4-chloro-2-hydroxy-3-[S-(+)-(2-methoxymethyl)pyrrolidin-1-yl]aminosulfonylphenyl]cyanoguanidine Following the general procedure for cyanoguanidine formation outlined in example 1, N-(2-bromophenyl)-N'-[4-chloro-2-tert-butyldimethylsilyloxy-3-[S-(+)-(2-methoxymethyl)pyrrolidin-1-yl]aminosulfonylphenyl]carbodiimide (152 mg, 0.25 mmol), cyanamide (42 mg, 1.0 mmol) and N,N-diisopropylethylamine (39 mg, 0.3 mmol) were reacted, followed by desilylation with Cesium fluoride (45.6 mg, 0.3 mmol) to form the desired product (33 mg, 25%). EI-MS m/z 543.6 (M$^+$).

N-(2,3-Dichlorophenyl)-N'-[4-chloro-2-hydroxy-3-[S-(+)-(2-methoxymethyl)pyrrolidin-1-yl]aminosulfonylphenyl]cyanoguanidine Following, the general procedure for carbodiimide formation outlined in example 1, N-(2,3dichlorophenyl)-N'-[4-chloro-2-tert-butyldimethylsilyloxy-3-[S-(+)-(2-methoxymethyl)pyrrolidin-1-yl]sulfonylphenyl]carbodiimide (160 mg, 0.26 mmol), cyanamide (44 mg, 1.04 mmol) and N,N-diisopropylethylamine (41 mg, 0.31 mmol) were reacted, followed by desilylation with Cesium fluoride (48 mg, 0.31 mmol) to form the desired product (35 mg, 25%). EI-MS m/z 532 (M$^+$).

N-Phenyl-N'-[4-chloro-2-hydroxy-3-[S-(+)-(2-methoxymethyl)pyrrolidin-1-yl]aminosulfonylphenyl]cyanoguanidine Following the general procedure for carbodiimide formation outlined in example 1, N-phenyl-N'-[4-chloro-2-tert-butyldimethylsilyloxy-3-[S-(+)-(2-methoxymethyl)pyrrolidin-1-yl]sulfonylphenyl]carbodiimide (125 mg, 0.23 mmol), cyanamide (38.6 mg, 0.92 mmol) and N,N-diisopropylethylamine (36.2 mg, 0.28 mmol) were reacted, followed by desilylation with Cesium fluoride (42 mg, 0.28 mmol) to form the desired product (38 mg, 35%). LC-MS m/z 462.2.

Examples 6 & 7

Preparation of N-(2-Bromophenyl)-N'-[4-chloro-2-hydroxy-3-[R-(2-methoxymethyl)pyrrolidin-1-yl]aminosulfonylphenyl]cyanoguanidine and N-(2,3-Dichlorophenyl)-N'-[4-chloro-2-hydroxy-3-[R-(2-methoxymethyl)pyrrolidin-1-yl]aminosulfonylphenyl]cyanoguanidine R-N-(2-Methoxymethyl)pyrrolidin-1-yl-2,6-dichloro-3-nitrobenzenesulfonamide Following the general procedure for sulfonamide formation outlined in example 1, 6-dichloro-3-nitrobenzenesulfonyl chloride (2.0 g, 6.89 mmol), (R)-2-(methyoxymethyl)pyrrolidine (0.783 mL, 8.27 mmol) and triethylamine (1.44 mL, 10.34 mmol) were reacted to form the desired product (1.69 g, 66%). EI-MS m/z 368 (M$^-$).

R-N-(2-Methoxymethyl)pyrrolidin-1-yl-6-chloro-2-hydroxy-3-nitrobenzenesulfonamide Following the general hydrolysis procedure outlined in example (R)-N-(2-methoxymethyl)pyrrolidin-1-yl-2,6-dichloro-3-nitrobenzenesulfonamide (2.16 g, 5.85 mmol), 60% sodium hydride (702 mg, 17.55 mmol) and water (137 mg, 7.6 mmol) were reacted to form the desired product (2.0 g, 97%). EI-MS m/z 349.1 (M$^-$).

(R)-N-(2-Methoxymethyl)pyrrolidin-1-yl-3-amino-6-chloro-2-hydroxybenzenesulfonamide Following the general hydrogenation procedure outlined in example 1, (R)-N-(2-methoxymethyl)pyrrolidin-1-yl-6-chloro-2-hydroxy-3-nitrobenzenesulfonamide (2.0 g, 4.44 mmol) was reduced with hydrogen and Pd/C (1.5 g) to form the desired product (1.75 g, 96%). EI-MS m/z 319.1 (M$^-$).

N-(2-Bromophenyl)-N'-[4-chloro-2-hydroxy-3-[(R)-(2-methoxyl)pyrrolidin-1-yl]aminosulfonylphenyl]thiourea Following the general procedure for thiourea formation outlined in example 1, (R)-N-(2-methoxymethyl)pyrrolidin-1-yl-3-amino-6-chloro-2-hydroxybenzenesulfonamide (390 mg, 1.21 mmol) and 2-bromophenylthioisocyanate (286 mg, 1.33 mmol) were coupled to form the desired thiourea (462 mg, 71%). EI-MS m/z 535.1 (M$^+$).

N-(2,3-Dichlorophenyl)-N'-[4-chloro-2-hydroxy-3-[(R)-2-methoxymethyl)pyrrolidin-1-yl]aminosulfonylphenyl]thiourea Following the general procedure for thiourea formation outlined in example 1, (R)-N-(2-methoxymethyl)pyrrolidin-1-yl-3-amino-6-chloro-2-hydroxybenzenesulfonamide (360 mg, 1.12 mmol) and 2,3-dichlorophenylisothiocyanate (251 mg, 1.23 mmol) were coupled to form the desired thiourea (410 mg, 70%). EI-MS m/z 525.1 (M$^+$).

N-(2-Bromophenyl)-N'-[4-chloro-2-tert-butyldimethyl-silyloxy-3-[(R)-(2-methoxymethyl)pyrrolidin-1-yl]aminosulfonylphenyl]thiourea Following the general procedure for protected phenyl thiourea formation outlined in example 1, N-(2-bromophenyl)-N'-[4-chloro-2-hydroxy-3-[(R)-(2-methoxymethyl)pyrrolidin-1-yl]aminosulfonylphenyl]

thiourea (462 mg, 0.86 mmol), tert-butyldimethylsilyl chloride (651 mg, 4.3 mmol) and imidazole (118 mg, 1.73 mmol) were reacted to form the desired product (216 mg, 39%). EI-MS m/z 650 (M$^+$).

N-(2,3-Dichlorophenyl)-N'-[4-chloro-2-tert-butyldimethylsilyloxy-3-[(R)-(2-methoxymethyl)pyrrolidin-1-yl]aminosulfonylphenyl]thiourea Following the general procedure for protected phenyl thiourea formation outlined in example 1, N-(2,3-dichlorophenyl)-N'-[4-chloro-2-hydroxy-3-[(R)-(2-methoxymethyl)pyrrolidin-1-yl]aminosulfonylphenyl]thiourea (410 mg, 0.78 mmol), tert-butyldimethylsilyl chloride (589 mg, 3.9 mmol) and imidazole (106 mg, 1.56 mmol) were reacted to form the desired product (202 mg, 40%). EI-MS m/z 640.2 (M$^+$).

N-(2-Bromophenyl)-N'-[4-chloro2-tert-butyldimethylsilyloxy-3-[(R)-(2-methoxymethyl)pyrrolidin-1-yl]aminosulfonylphenyl]carbodiimide Following the general procedure for carbodiimide formation outlined in example 1, N-(2-bromophenyl)-N'-[4-chloro-2-tert-butyldimethylsilyloxy-3-[(R)-(2-methoxymethyl)pyrrolidin-1-yl]aminosulfonylphenyl]thiourea (216 mg, 0.33 mmol), methanesulfonyl chloride (0.05 mL, 0.66 mmol) and triethylamine (0.09 mL, 0.66 mmol) were reacted to form the desired product (200 mg, 97%). %). $^1$H NMR (CDCl$_3$) δ 0.37 (s, 6H), 1.02 (s, 9H), 1.9 (m, 4H), 3.23 (m, 4H), 3.42 (m, 3H), 4.13 (m, 1H), 7.08 (d, 2H), 7.20 (d, 1H), 7.3 (t, 1H), 7.38 (d, 1H), 7.6 (d, 1H).

N-(2,3-Dichlorophenyl)-N'-[4-chloro-2-tert-butyldimethylsilyloxy-3-[(R)-(2-methoxymethyl)pyrrolidin-1-yl]aminosulfonylphenyl]carbodiimide Following the general procedure for carbodiimide formation outlined in example 1, N-(2,3-dichlorophenyl)-N'-[4-chloro-2-tert-butyldimethylsilyloxy-3-[(R)-(2-methoxymethyl)pyrrolidin-1-yl]aminosulfonylphenyl]thiourea (202 mg, 0.32 mmol), methanesulfonyl chloride (0.05 mL, 0.64 mmol) and triethylamine (0.09 mL, 0.64 mmol) were reacted to form the desired product (190 mg, 99%). $^1$H NMR (CDCl$_3$) δ 0.34 (s, 6H), 1.04 (s, 9H), 1.4 (m, 2H), 1.8 (m, 2H), 3.15 (s, 3H), 3.25 (m, 2H), 3.43 (m, 2H), 4.13 (m, 1H), 7.09 (d, 2H), 7.12 (d, 1H), 7.19 (t, 1H), 7.3 (d, 1H), 7.34 (d, 1H).

N-(2-Bromophenyl)-N'-[4-chloro-2-hydroxy-3-[(R)-(2-methoxymethyl)pyrrolidin-1-yl]aminosulfonylphenyl]cyanoguanidine Following the general procedure for cyanoguanidine formation outlined in example 1, N-(2-bromophenyl)-N'-[4-chloro-2-tert-butyldimethylsilyloxy-3-[(R)-(2-methoxymethyl)pyrrolidin-1-yl]aminosulfonylphenyl]carbodiimide (240 mg, 0.39 mmol), cyanamide (66 mg, 1.56 mmol) and N,N-diisopropylethylamine (63 mg, 0.47 mmol) were reacted, followed by desilylation with Cesium fluoride (72 mg, 0.47 mmol) to form the desired product (75 mg, 35%). EI-MS m/z 543.6 (M$^+$).

N-(2,3-Dichlorophenyl)-N'-[4-chloro-2-hydroxy-3-[(R)-(2-methoxymethyl)pyrrolidin-1-yl]aminosulfonylphenyl]cyanoguanidine Following the general procedure for cyanoguanidine formation outlined in example 1, N-(2,3-dichlorophenyl)-N'-[4-chloro-2-tert-butyldimethylsilyloxy-3-[(R)-(2-methoxymethyl)pyrrolidin-1-yl]aminosulfonylphenyl]carbodiimide (224 mg, 0.37 mmol), cyanamide (63 mg, 1.48 mmol) and N,N-diisopropylethylamine (60 mg, 0.43 mmol) were reacted, followed by desilylation with Cesium fluoride (67 mg, 0.43 mmol) to form the desired product (70 mg, 36%). EI-MS m/z 533.5 (M$^+$).

Examples 8 & 9

Preparation of N-(2-bromophenyl)-N'-[4-chloro-2-hydroxy-3-(N"-isoxazolidinylaminosulfonylphenyl] cyanoguanidine and N-(2,3-Dichlorophenyl)-N'-[4-chloro-2-hydroxy-3-(N"-isoxazolidinylaminosulfonylphenyl]cyanoguanidine N-(Ethoxycarbonyl)isoxazolidine To a solution of KOH (6.4 g, 0.11 mol) and hydroxyurethane (12 g, 0.11 mol) in ethanol (50 mL) was added 1,3-dibromopropane (5.8 mL, 0.057 mol). The resulting suspension was heated at reflux for 1 hour. After the mixture was cooled to room temperature, an additional portion of KOH (3.2 g, 0.055 mol) and of dibromopropane (2.9 mL, 0.028 mol) was added. The mixture was then refluxed for 1 hour, cooled to room temperature, and solvent was evaporated. The residue was suspended in boiling ether three times and filtered. The combined filtrates were dried over sodium sulfate, filtered, and evaporated. A portion of 3 g of the crude product was purified by flush column chromatography (EtOAC/Hexane, gradient elution), yielding 1.18 g of N-(ethoxycarbonyl)isoxazolidine. $^1$H NMR (CDCl$_3$) δ 1.15 (t, 3H), 2.15 (q, 2H), 3.55 (t, 2H), 3.8 (t, 2H), 4.1 (q, 2H).

Isoxazolidine Hydrochloride

N-(ethoxycarbonyl)isoxazolidine (1.18 g, 9.1 mmol) was dissolved in aqueous HCl (6N, 7 mL) and heated at reflux for 2 hours. After being cooled to room temperature, this solution was washed with ether (3x) and then evaporated affording crude isoxazolidine hydrochloride which was recrystalized from ethanol/ether yielding 0.79 g (80%) of isoxazolidine hydrochloride. $^1$H NMR (CDCl$_3$; CH$_3$OD), δ 2.5 (q, 2H), 3.55 (t, 2H), 4.2 (t, 2H).

(N-Isoxazolidinyl)-2.6-dichloro-3-nitrobenzenesulfonamide

Following the general procedure for sulfonamide formation outlined in example 1, 2,6-dichloro-3-nitrobenzenesulfonyl chloride (1.5 g, 5.2 mmol), isoxazolidine hydrochloride (0.56 g, 5.2 mmol) and triethylamine (2.2 mL, 15.5 mmol) were reacted to form the desired product (1.2 g, 71%). EI-MS m/z 327 (M$^+$).

(N-Isoxazolidinyl)-2-hydroxy-6-dichloro-3-nitrobenzenesulfonamide

Following the general hydrolysis procedure outlined in example 1, (N-isoxazolidinyl)-2,6dichloro-3-nitrobenzenesulfonamide (1.08 g, 3.3 mmol), 80% sodium hydride (0.3 g, 10.0 mmol) and water (72 mg, 4.0 mmol) were reacted to form the desired product (0.79 g, 77%). EI-MS m/z 309 (M$^+$).

(N-Isoxazolidinyl)-2-hydroxy -3-amino-6-dichloro-benzenesulfonamide

Following the general hydrogenation procedure outlined in example 1, (N-isoxazolidinyl)-2-hydroxydichloro-3-nitrobenzenesulfonamide (0.84 g, 2.7 mmol) was reduced with hydrogen and Pd/C (840 mg) to form the desired product (0.75 g crude). EI-MS m/z 279 (M$^+$).

N-(2-Bromophenyl)-N'-[4-chloro-2-hydroxy-3-(N"-isoxazolidinylaminosulfonylphenyl]thiourea Following the general procedure for thiourea formation outlined in example 1, (N-isoxazolidinyl)-2-hydroxy-3-amino-6-dichloro-benzenesulfonamide (624 mg, 2.24 mmol) and 2-bromophenylisothiocyanate (528 mg, 2.46 mmol) were coupled to form the desired thiourea (620 mg, 56%). EI-MS m/z 493 (M$^+$).

N-(2,3-Dichlorophenyl)-N'-[chloro-2-hydroxy-3-(N"-isoxazolidinylaminosulfonylphenyl]thiourea Following the general procedure for thiourea formation outlined in example 1, (N-isoxazolidinyl)-2-hydroxy-3-amino-6-dichloro-benzenesulfonamide (590 mg, 2.11 mmol) and 2,3-dichlorophenylisothiocyanate (474 mg, 2.53 mmol) were coupled to form the desired thiourea (753 mg, 74%). EI-MS m/z 481.75 (M⁻).

N-(2,3-Dichlorophenyl)-N'-[4-chloro-2-tert-butyldimethylsilyloxy-3-(N''-isoxazolidinylaminosulfonylphenyl]thiourea Following the general procedure for protected phenyl thiourea formation outlined in example 1, N-(2,3-dichlorophenyl)-N'-[4-chloro-2-hydroxy-3-(N''-isoxazolidinylaminosulfonylphenyl]thiourea (726 mg, 1.51 mmol), tert-butyldimethylsilyl chloride (1.14 mg, 7.55 mmol) and imidazole (205 mg, 3.02 mmol) were reacted to form the desired product (355 mg, 66%). EI-MS m/z 597.83 (M⁺).

N-(2-Bromophenyl)-N '-[chloro-2-tert-butyldimethylsilyloxy-3-(N''-isoxazolidinylaminosulfonylphenyl] carbodiimide Following the general procedure for carbodiimide formation outlined in example 1, N-(2-bromophenyl)-N'-[4-chloro-2-tert-butyldimethylsilyloxy-3-(N''-isoxazolidinylaminosulfonylphenyl]thiourea (480 mg, 0.79 mmol), methanesulfonyl chloride (0.12 mL, 1.58 mmol) and triethylamine (0.22 mL, 1.58 mmol) were reacted to form the desired product (480 mg, crude). $^1$H NMR (CDCl$_3$) δ 0.39 (s, 6H), 1.1 (s, 9H), 2.4 (m, 2H), 3.76 (t, 2H), 4.22 (t, 2H), 7.09 (m, 2H), 7.21 (d, 1H), 7.29 (m, 1H), 7.45 (d, 1H), 7.6 (d, 1H).

N-(2-,3-Dichlorophenyl)-N'-[4-chloro-2-tert-butyldimethylsilyloxy-3-(N''-isoxazolidinylaminosulfonylphenyl]carbodiimide Following the general procedure for carbodiimide formation outlined in example 1, N-(2,3-dichlorophenyl)-N'-[4-chloro-2-tert-butyldimethylsilyloxy-3-(N''-isoxazolidinylaminosulfonylphenyl]thiourea (355 mg, 0.59 mmol), methanesulfonyl chloride (0.09 mL, 1.18 mmol) and triethylamine (0.16 mL, 1.18 mmol) were reacted to form the desired product (355 mg, crude). $^1$H NMR (CDCl$_3$) δ 0.38 (s, 6H), 1.03 (s, 9H), 2.4 (m, 2H), 3.77 (t, 2H), 4.22 (t, 2H), 7.12 (d, 1H), 7.16 (t, 1H), 7.26 (d, 1H), 7.31 (d, 1H), 7.40 (d, 1H).

N-(2-Bromophenyl)-N'-[4-chloro-2-tert-butyldimethylsilyloxy-3-(N''-isoxazolidinylaminosulfonylphenyl] cyanoguanidine Following the general procedure for cyanoguanidine formation outlined in example 1, N-(2-bromophenyl)-N'-[4-chloro-2-tert-butyldimethylsilyloxy-3-(N''-isoxazolidinylaminosulfonylphenyl]carbodiimide (480 mg, 0.84 mmol), cyanamide (142 mg, 3.36 mmol) and N,N-diisopropylethylamine (130 mg, 1.0 mmol) were reacted, followed by desilylation with Cesium fluoride (153.2 mg, 1.0 mmol) to form the desired product (150 mg, 36%). LC-MS m/z 500.

N-(2-Bromophenyl)-N'-[4-chloro-2-tert-butyldimethylsilyloxy-3-(N''-isoxazolidinylaminosulfonylphenyl] cyanoguanidine Following the general procedure for cyanoguanidine formation outlined in example 1, N-(2-,3-dichlorophenyl)-N'-[4-chloro-2-tert-butyldimethylsilyloxy-3-(N''-isoxazolidinylaminosulfonylphenyl]carbodiimide (355 mg, 0.63 mmol), cyanamide (105 mg, 2.52 mmol) and N,N-diisopropylethylamine (100 mg, 1.26 mmol) were reacted, followed by desilylation with Cesium fluoride (115 mg, 0.76 mmol) to form the desired product (28 mg, 10%). LC-MS m/z 490.

Examples 10 & 11

Preparation of N-(2-Bromophenyl)-N'-[4-chloro-2-hydroxy-3-(N''-tetrahydroisoxazylaminosulfonyl) phenyl]cyanoguanidine and N-(2,3-Dichlorophenyl) N'-[4-chloro-2-hydroxy-3-(N''-tetrahydroisoxazylaminosulfonyl)phenyl] cyanoguanidine N-(Ethoxycarbonyl)tetrahydroisoxazine To a solution of KOH (3.34 g, 59.6 mmol) and hydroxyurethane (6.1 g, 58.5 mmol) in ethanol (25 mL) was added 1,4-dibromobutane (3.5mL, 29.3 mmol). The resulting suspension was heated at reflux for 1 hour. After the mixture was cooled to room temperature, an additional portion of KOH (1.65 g, 29.4 mmol) and of dibromopropane (1.8 mL, 15 mmol) was added. The mixture was then refluxed for 1 hour, cooled to room temperature, and solvent was evaporated. The residue was suspended in boiling ether three times and filtered. The combined filtrates were dried over sodium sulfate, filtered, and evaporated. A portion of 4 g of the crude product was purified by flash column chromatography (EtOAC/Hexane, gradient elution), yielding 1.85 g of N-(ethoxycarbonyl)tetrahydroisoxazine. $^1$H NMR (CDCl$_3$) δ 1.05 (q, 3H), 1.45 (dd, 2H), 1.55 (dd, 2H), 3.4 (t, 2H), 3.7 (t, 2H), 3.95 (q, 2H).

Tetrahydroisoxazine Hydrochloride

N-(ethoxycarbonyl)tetrahydroisoxazine (1.85 g, 11.6 mmol) was dissolved in aqueous HCl (6N, 7.8 mL)and heated at reflux for 7 hours. After being cooled to room temperature, this solution was washed with ether (3×) and then evaporated affording crude tetraisoxazine hydrochloride which was recrystalized from ethanol/ether yielding 0.74 g (52%) of tetrahydroisoxazine hydrochloride. $^1$H NMR (CH$_3$OD) δ 1,85 (dd, 2H), 1.95 (dd, 2H), 3.4 (t, 2H), 4.25 (t, 2H).

c) (N-Tetrahydroisoxazinyl)-2,6-dichloro-3-nitrobenzenesulfonamide

Following the general procedure for sulfonamide formation outlined in example 1, 2,6-dichloro-3-nitrobenzenesulfonyl chloride (1.75 g, 6.0 mmol) Tetrahydroisoxazine hydrochloride hydrochloride (0.63 g, 5.1 mmol) and triethylamine (2.2 mL, 15.5 mmol) were reacted to form the desired product (1.32 g, 75%). EI-MS m/z 341 (M⁺).

(N-Tetrahydroisoxazinyl)-2-hydroxy-6-chloro-3-nitrobenzenesulfonamide

Following the general hydrolysis procedure outlined in example 1, (N-Tetrahydroisoxazinyl)-2,6-dichloro-3-nitrobenzenesulfonamide (0.1 g, 0.29 mmol), 80% sodium hydride (26 mg, 0.88 mmol) and water (6.3 mg, 0.35 mmol) were reacted to form the desired product (50 mg, 53%). EI-MS m/z 323 (M⁺).

(N-Tetrahydroisoxazyl)-2-hydroxy-3-amino-6-chlorobenzenesulfonamide

Following the general hydrogenation procedure outlined in example 1, (N-tetrahydroisoxazinyl)-2-hydroxy-6-chloro-3-nitrobenzenesulfonamide (0.76 g, 2.35 mmol) was reduced with hydrogen and Pd/C (760 mg) to form the desired product (890 mg, crude). EI-MS m/z 293 (M⁺).

N-(2-Bromophenyl)-N'-[4-chloro-2-hydroxy-3-(N''-tetrahydroisoxazylaminosulfonyl)phenyl]thiourea Following the general procedure for thiourea formation outlined in example 1, (N-tetrahydroisoxazinyl)-2-hydroxy-3-amino-6-chlorobenzenesulfonamide (620 mg, 2.12 mmol) and 2-bromophenylisothiocyanate (500 mg, 2.33 mmol) were coupled to form the desired thiourea (627 mg, 58%). EI-MS m/z 507 (M⁻).

N-(2,3-Dichlorophenyl)-N'-[4-chloro-2-hydroxy-3-(N"-tetrahydroisoxazmlaminosulfonyl)phenyl]thiourea Following the general procedure for thiourea formation outlined in example 1, (N-tetrahydroisoxazinyl)-2-hydroxy-3-amino-6-chlorobenzenesulfonamide (888 mg, 3.04 mmol) and 2,3-dichlorophenylisothiocyanate (682 mg, 3.34 mmol) were coupled to form the desired thiourea (958 mg, 64%). EI-MS m/z 495.67 (M−).

N-(2-Bromophenyl)-N'-[4-chloro-2-tert-butyldimethylsilyloxy-3-(N"-tetrahydroisoxazylaminosulfonyl)phenyl]thiourea Following the general procedure for protected phenyl thiourea formation outlined in example 1, N-(2-bromophenyl)-N'-[4-chloro-2-hydroxy-3-(N"-tetrahydroisoxazylaminosulfonyl)phenyl]thiourea (627 mg, 1.24 mmol), tert-butyldimethylsilyl chloride (934 mg, 6.2 mmol) and imidazole (169 mg, 2.48 mmol) were reacted to form the desired product (350 mg, 45%). EI-MS m/z 622 (M+).

N-(2,3-Dichlorophenyl)-N'-[4-chloro-2-tert-butyldimethylsilyloxy-3-(N"-tetrahydroisoxazylaminosulfonyl)phenyl]thiourea Following the general procedure for protected phenyl thiourea formation outlined in example 1, N-(2,3-dichlorophenyl)-N'-[4-chloro-2-hydroxy-3-(N"-tetrahydroisoxazylaminosulfonyl)phenyl]thiourea (898 mg, 1.81 mmol), tert-butyldimethylsilyl chloride (1.4 g, 9.05 mmol) and imidazole (246 mg, 3.62 mmol) were reacted to form the desired product (546 mg, 49%). EI-MS m/z 611.81 (M+).

N-(2-Bromophenyl)-N'-[4-chloro-2-tert-butyldimethylsilyloxy-3-(N"-tetrahydroisoxazylaminosulfonyl)phenyl]carbodiimide Following the general procedure for carbodiimide formation outlined in example 1, N-(2-bromophenyl)-N'-[4-chloro-2-tert-butyldimethylsilyloxy-3-(N"-tetrahydroisoxazylaminosulfonyl)phenyl]thiourea (385 mg, 0.74 mmol), methanesulfonyl chloride (0.12 mL, 1.48 mmol) and triethylamine (0.21 mL, 1.48 mmol) were reacted to form the desired product (385 mg, crude). $^1$H NMR (CDCl$_3$) δ 0.35 (s, 6H), 1.02 (s, 9H), 1.68 (m, 2H), 1.9 (m, 2H), 3.04 (t, 2H), 4.0 (t, 2H), 7.09 (d, 1H), 7.12 (d, 1H), 7.2 (d, 1H), 7.3 (t, 1H), 7.42 (d, 1H), 7.6 (d, 1H).

N-(2,3-Dichlorophenyl)-N'-[4-chloro-2-tert-butyldimethylsilyloxy-3-(N"-tetrahydroisoxazylaminosulfonyl)phenyl]carbodiimide Following the general procedure for carbodiimide formation outlined in example 1, N-(2,3-dichlorophenyl)-N'-[4-chloro-2-tert-butyldimethylsilyloxy-3-(N"-tetrahydroisoxazylaminosulfonyl)phenyl]thiourea (547 mg, 0.897 mmol), methanesulfonyl chloride (0.14 mL, 1.79 mmol) and triethylamine (0.25 mL, 1.79 mmol) were reacted to form the desired product (547 mg, crude). $^1$H NMR (CDCl$_3$) δ 0.36 (s, 6H), 1.03 (s, 9H), 1.68 (m, 2H), 1.9 (m, 2H), 3.53 (t, 2H), 4.0 (t, 2H), 7.11 (m, 2H), 7.14 (t, 1H), 7.2 (d, 1H), 7.3 (d, 1H), 7.39 (d, 1H).

N-(2-Bromophenyl)-N'-[4-chloro-2-tert-butyldimethylsilyloxy-3-(N"-tetrahydroisoxazylaminosulfonyl)phenyl]cyanoguanidine Following the general procedure for cyanoguanidine formation outlined in example 1, N-(2-bromophenyl)-N'-[4-chloro-2-tert-butyldimethylsilyloxy-3-(N"-tetrahydroisoxazylaminosulfonyl)phenyl]carbodiimide (385 mg, 0.79 mmol), cyanamide (133 mg, 3.16 mmol) and N,N-diisopropylethylamine (127 mg, 0.95 mmol) were reacted, followed by desilylation with Cesium fluoride (144 mg, 0.95 mmol) to form the desired product (100 mg, 26%). EI-MS m/z 515 (M+).

N-(2,3-Dichlorophenyl)-N'-[4-chloro-2-tert-butyldimethylsilyloxy-3-(N"-tetrahydroisoxazylaminosulfonyl)phenyl]cyanoguanidine Following the general procedure for cyanoguanidine formation outlined in example 1, N-(2,3-dichlorophenyl)-N'-[4-chloro-2-tert-butyldimethylsilyloxy-3-(N"-tetrahydroisoxazylaminosulfonyl)phenyl]carbodiimide (547 mg, 0.95 mmol), cyanamide (159 mg, 3.8 mmol) and N,N-diisopropylethylamine (150 mg, 1.14 mmol) were reacted, followed by desilylation with Cesium fluoride (174 mg, 1.14 mmol) to form the desired product (190 mg, 40%). LC-MS m/z 504.

Example 12

Preparation of N-[4-Chloro-2-hydroxy-3-[N",N"-dimethylaminosulfonylphenyl]-N'-(2-bromophenyl)propylguanidine N,N-Dimethyl-3-amino-6-chloro-2-hydroxybenzenesulfonamide To a solution of N,N-Dimethyl-6-chloro-2-hydroxy-3-nitrobenzenesulfonamide (550 mg, 1.96 mmol) in ethyl acetate, was added 10% Pd/C (550 mg). The mixture was flushed with argon, and then stirred under a hydrogen atmosphere at balloon pressure for 3 hours at room temperature. TLC showed the reaction was not complete. The mixture was filtered through celite and the celite was washed with methanol. The mixture was retreated under the same conditions as mentioned above. After 3 hours, the solvent was evaporated to give the desired product (480 mg, 98%). EI-MS (m/z) 250.82, 252.87 (M+).

N-[4-Chloro-2-hydroxy-3-[N",N"-dimethylaminosulfonyl]phenyl]-N'-(2-bromophenyl)thiourea A solution of N,N-dimethyl-3-amino-6-chloro-2-hydroxybenzene sulfonamide (480 mg, 3.58 mmol) and 2-bromophenylisothiocyanate (0.53 μL, 3.94 mmol) in 10 mL of ethanol was stirred at room temperature for overnight. Purification by column chromatography on silica gel, eluting with ethyl acetate/hexane (gradient elution) gave the desired product (368 mg, 22%). EI-MS (m/z) 463.67, 465.66, 467.65, 468.64 (M+).

N-[4-Chloro-2-tert-Butyldimethylsilyloxy-3-[N",N"-dimethylaminosulfonyl]phenyl]-N'-(2-bromophenyl)thiourea To a solution of N-[4-chloro-2-hydroxy-3-[N",N"-dimethylaminosulfonyl]phenyl]-N'-2-bromophenyl)thiourea (350 mg, 0.755 mmol) in THF (10 mL), tert-butyldimethylsilyl chloride (171 mg, 1.13 mmol) and iridazole (106 mg, 1.56 mmol) were added. The reaction mixture was stirred at room temperature for overnight. Then it was partitioned between ethyl acetate and water. The combined organic phase was dried and concentrated. Chromatography of the residue on silica gel gave desired product (150 mg, 46%) and recovered starting material (90 mg). EI-MS m/z 577.81, 579.66, 580.65, 581.46, 582.77 (M+).

N-[4-Chloro2-tert-butyldimethylsiloxy-3-N",N"-dimethylaminosulfonyl]phenyl]-N'-(2-bromophenyl)carbodiimide To a solution of N-[4-chloro-2-tert-butyldimethylsiloxy-3-[N",N"-dimethylaminosulfonyl]phenyl]-N'-(2-bromophenyl)thiourea (150 mg, 0.26 mmol) in dichloromethane (5 mL) at 0° C., methanesulfonyl chloride (40 μL, 0.52 mmol), 4-Dimethylaminopyridine (10 mg) and triethylamine (0.11 mL, 0.77 mmol) were added. The reaction mixture was stirred at 0° C. for 3 hours. Then it was partitioned between ethyl acetate and water. The combined organic phase was dried and concentrated to give the desired product (120 mg, 85%). IR: 2140 cm$^{-1}$.

N-[4-Chloro2-hydroxy-3-[N",N"-dimethylaminosulfonyl] phenyl]-N'-(2-bromophenyl)propylguanidine To a solution of N-[4-chloro-2-tert-butyldimethylsiloxy-3-[N",N"-dimethylaminosulfonyl]phenyl]-N'-(2-bromophenyl)carbodiimide (60 mg, 0.11 mmol) in tetrahydrofuran (2 mL) at room temperature, N,N-diisopropylethylamine (14 µL, 0.12 mmol) and n-propylamine (10 µL, 012 mmol) were added. The reaction mixture was stirred at room temperature for 15 minutes, then cooled to 0° C., and TBAF and methanol (1 mL) were added. After 30 minutes, the mixture was quenched with water, and extracted with ethylacetate. The organic layer was concentrated under reduced pressure. The residue was purified by Gilson HPLC to give the desired product (19 mg, 35%). EI-MS m/z 488.7, 490.68, 492.67 (M⁺).

Example 13

Preparation of N-[4-Chloro-2-hydroxy-3-(N",N"-dimethylaminosulfonyl)phenyl]-N'-(2-chlorophenyl) cyanoguanidine a) N-[4-Chloro-2-hydroxy-3-(N",N"-dimethylaminosulfonyl)phenyl]-N'-(2-chlorophenyl)thiourea Following the general procedure for thiourea formation outlined in example 12, N,N-dimethyl-3-aminochloro-2-hydroxybenzenesulfonamide (450 mg, 1.8 mmol) and 2-chlorophenylisothiocyanate (335.6 mg, 1.98 mmol) were coupled to form the desired thiourea (526 mg, 70%). EI-MS m/z 421.47 (M⁺).

b) N-(2-Chlorophenyl)-N[4-[chloro-2-tert-butyldimethylsilyoxy-3-(N",N"-dimethylaninosulfonyl) phenyl]thiourea Following the general procedure for protected phenyl thiourea formation outlined in example 12, N-[4-chloro-2-hydroxy-3-(N",N"-dimethylaminosulfonyl)phenyl]-N'-(2-chlorophenyl)thiourea (500 mg, 1.19 mmol), tert-butyldimethylsilyl chloride (897 mg, 5.95 mmol) and imidazole (162 mg, 2.38 mmol) were reacted to form the desired product (311 mg, 49%). EI-MS m/z 535.32 (M⁺).

c) N-(2-Chlorophenyl)-N'-[4-chloro-2-tert-butyldimethylsilyloxy-3-(N",N"-dimethylaminosulfonyl) phenyl]carbodiimide Following the general procedure for carbodiimide formation outlined in example 12, N-(2-chlorophenyl)-N'-[4-chloro-2-tert-butyldimethylsilyloxy-3-(N",N"-dimethylaminosulfonyl)phenyl]thiourea (311 mg, 0.58 mmol), methanesulfonyl chloride (0.09 mL, 1.16 mmol) and triethylamine (0.15 mL, 1.16 mmol) were reacted to form the desired product (300 mg, crude). ¹H NMR (CDCl₃) δ 0.37 (s, 6H), 1.03 (s, 9H), 2.87 (s, 6H), 7.05 (d, 1H), 7.12 (t, 1H), 7.22 (m, 2H), 7.34 (d, 1H), 7.42 (d, 1H).

d) N-(2-Chlorophenyl)-N'-[4-chloro-3-(N",N"-dimethylaminosulfonyl)phenyl]cyanoguanidine Following the general procedure for cyanoguanidine formation outlined in example 12, N-(2-chlorophenyl)-N'-[4-chloro-2-tert-butyldimethylsilyloxy-3-(N",N"-dimethylaminosulfonyl)phenyl]carbodiimide (300 mg, 0.6 mmol), cyanamide (100 mg, 2.4 mmol) and N,N-diisopropylethylamine (94 mg, 0.72 mmol) were reacted, followed by desilylation with Cesium fluoride (110 mg, 0.72 mmol) to form the desired product (129 mg, 50%). EI-MS m/z 428.0 (M⁺). ¹H NMR (DMSO-d₆) δ 2.86 (s, 6H), 7.2 (d, 1H), 7.32 (t, 1H), 7.36 (t, 1H), 7.43 (d, 1H), 7.51 (d, 1H), 7.57 (d, 1H), 8.98 (s, 1H), 9.18 (s, 1H), 10.51 (s, 1H).

Example 14

Preparation of N-[4-Chloro-2-hydroxy-3-(N",N"-dimethylaminosulfonyl)phenyl]-N'-(2-fluoro-3-chlorophenyl)cyanoguanidine a) 2-Fluoro-3-chlorophenylisothiocyanate Into a solution of 2-fluoro-3-chloroaniline (1.0 g, 6.87 mmol) in 30 mL of toluene at room temperature, thiophosgene (0.8 mL, 10.3 mmol) and triethylamine (1.12 mL, 8.24 mmol) were added. The mixture was stirred at room temperature for 16 hours. The mixture was parationed between ethyl acetate and water. The combined organic layer was then concentrated to give the desired product (950 mg, 74%). ¹H NMR (CDCl₃) δ 7.09 (m, 2H), 7.30 (m, 1H).

b) N-[4-Chloro-2-hydroxy-3-(N",N"-dimethylaminosulfonyl)phenyl]-N'-(2-fluoro-3-chlorophenyl)thiourea Following the general procedure for thiourea formation outlined in example 12, N,N-dimethyl-3-amino-6-chloro-2-hydroxybenzenesulfonamide (500 mg, 2 mmol) and 2-fluoro-3-chlorophenylisothiocyanate (374 mg, 2 mmol) were coupled to form the desired thiourea (583 mg, 67%). EI-MS m/z 438.2(M⁺).

c) N-(2-Fluoro-3-chlorophenyl)-N'-[4-chloro-2-tert-butyldimethylsilyloxy-3-(N",N"-dimethylaminosulfonyl) phenyl]-N'-(2-fluoro-3-chlorophenyl)thiourea Following the general procedure for protected phenyl thiourea formation outlined in example 12, N-4-chloro-2-hydroxy-3-(N",N"-dimethylaminosulfonyl)phenyl]-N'-(2-fluoro-3-chlorophenyl)thiourea (533 mg, 1.22 mmol), tert-butyldimethylsilyl chloride (913 mg, 6.1 mmol) and imidazole (166 mg, 2.44 mmol) were reacted to form the desired product (412 mg, 61%). EI-MS m/z 552.2 (M⁺).

d) N-(2-Fluoro-3-chlorophenyl)-N'-[4-chloro-2-tert-butyldimethylsilyloxy-3-(N",N"-dimethylaminosulfonyl) phenyl]-N'-(2-fluoro-3-chlorophenyl)carbodiimide Following the general procedure for carbodiimide formation outlined in example 12, N-(2-fluoro-3-chlorophenyl)-N'-[4-chloro-2hert-butyldimethylsilyloxy-3-(N",N"-dmiethylaminosulfonyl)phenyl]-N'-(2-fluoro3-chlorophenyl)thiourea (412 mg, 0.75 mmol), methanesulfonyl chloride (0.14 mL, 1.5 mmol) and triethylamine (0.24 mL, 1.5 mmol) were reacted to form the desired product (410 mg, crude). ¹H NMR (CDCl₃) δ 0.37 (s, 6H), 0.99 (s, 9H), 2.85 (s, 6H), 7.05 (m, 2H), 7.25 (m, 3H).

e) Preparation of N-[4-Chloro-2-hydroxy-3-(N",N"-dimethylaminosulfonyl)phenyl]-N'-(2-fluoro-3-chlorophenyl)cyanoguanidine Following the general procedure for cyanoguanidine formation outlined in example 12, N-[4-chloro-3-tert-butyldimethylsilyloxy-3-(N",N"-dimethylaminosulfonyl) phenyl]-N'-(2-fluoro3-chlorophenyl)carbodiimide (410 mg, 0.79 mmol), cyanamide (133 mg, 3.16 mmol) and N,N-diisopropylethylamine (122 mg, 0.95 mmol) were reacted, followed by desilylation with Cesium fluoride (144 mg, 0.95 mmol) to form the desired product (140 mg, 40%). EI-MS m/z 446.2 (M⁺). ¹H NMR (DMSO-d₆) δ 2.87 (s, 6H), 7.2 (d, 1H), 7.32 (t, 1H), 7.40 (m, 2H), 7.59 (d, 1H), 9.11 (s, 1H), 9.3 (s, 1H), 10.53 (s, 1H).

Example 15

Preparation of N-[4-Chloro-2-hydroxy-3-(N",N"-dimethylaminosulfonyl)phenyl]-N'-(2-trifluoromethylphenyl)cyanoguanidine a) 2-Trifluoromethylisothiocyanate Into a solution of 2-trifluoromethylaniline (1.0 g, 6.21 mmol) in 30 mL of toluene at room temperature, thiophosgene (0.72 mL, 9.31 mmol) and triethylamine (1.01 mL, 7.45 mmol) was added. The mixture was stirred at room temperature for 16 hours. The mixture was parationed between ethyl acetate and water. The combined organic layer was then concentrated to give the desired product (1.01 g, 80%). $^1$H NMR (CDCl$_3$) δ 7.30 (m, 2H), 7.54 (t, 1H), 7.64 (d, 1H).

b) N-[4-Chloro-2-hydroxy-3-(N",N"-dimethylaminosulfonyl)phenyl]-N'-(2-trifluoromethylphenyl)thiourea Following the general procedure for thiourea formation outlined in example 12, N,N-dimethyl-3-amino-6-chloro-2-hydroxybenzenesulfonamide (500 mg, 2 mmol) and 2-trifluoromethylphenylisothiocyanate (548 mg, 2 mmol) were coupled to form the desired thiourea (469 mg, 52%). EI-MS m/z 454.0 (M$^+$).

c) N-(2-Trifluoromethylphenyl)-N'-[4-chloro-2-tert-butyldimethylsilyloxy-3(N",N"-dimethylaminosulfonyl)phenyl]thiourea Following the general procedure for protected phenyl thiourea formation outlined in example 12, N-[4-chloro-2-hydroxy-3-(N",N"-dimethylaminosulfonyl)phenyl]-N'-(2-trifluoromethylphenyl)thiourea (416 mg, 1.0 mmol), tert-butyldimethylsilyl chloride (750 mg, 5.0 mmol) and imidazole (136 mg, 2.0 mmol) were reacted to form the desired product (250 mg, 45%). EI-MS m/z 568.0 (M$^+$).

d) N-(2-Trifluoromethylphenyl)-N'-[chloro-2-tert-Butyldimethylsilyloxy-3-(N",N"-dimethylaminosulfonyl)phenyl]carbodiimide Following the general procedure for carbodiimide formation outlined in example 12, N-(2-trifluoromethylphenyl)-N-[4-chloro-2-tert-butyldimethylsilyloxy-3-(N",N"-dimethylaninosulfonyl)phenyl]thiourea (250 mg, 0.44 mmol), methanesulfonyl chloride (0.1 mL, 0.88 mmol) and triethylamine (0.14 mL, 0.88 mmol) were reacted to form the desired product (250 mg, crude). $^1$H NMR (CDCl$_3$) δ 0.38 (s, 6H), 1.04 (s, 9H), 2.87 (s, 6H), 7.07 (d, 1H), 7.2 (d, 1H), 7.29 (m, 2H), 7.54 (t, 1H), 7.66 (d, 1H).

e) Preparation of N-[4-Chloro-2-hydroxy-3-(N",N"-dimethylaminosulfonyl)phenyl]-N'-(2-trifluoromethylphenyl)cyanoguanidine Following the general procedure for cyanoguanidine formation outlined in example 12, N-[4-chloro-2-tert-butyldimethylsilyloxy-3-(N",N"-dimethylaminosulfonyl)phenyl]-N'-(2-trifluoromethylphenyl)carbodiimide (250 mg, 0.47 mmol), cyanamide (79 mg, 1.88 mmol) and N,N-diisopropylethylamine (73 mg, 0.56 mmol) were reacted, followed by desilylation with Cesium fluoride (86 mg, 0.56 mmol) to form the desired product (80 mg, 37%). EI-MS m/z 462.0 (M$^+$). $^1$H NMR (DMSO-d$_6$) δ 2.86 (s, 6H), 7.14 (d, 1H), 7.53 (m, 2H), 7.59 (d, 1H), 7.75 (t, 1H), 7.77 (d, 1H), 8.91 (s, 1H), 9.28 (s, 1H), 10.53 (s, 1H).

Example 16

Preparation of N-[4-Chloro-2-hydroxy-3-(N",N"-dimethylaminosulfonyl)phenyl]-N'-(2-methylphenyl)cyanoguanidine a) N-[4 Chloro-2-hydroxy-3-(N",N"-dimethyl-aminosulfonyl)phenyl]-N'-(2-methylphenyl)thiourea Following the general procedure for thiourea formation outlined in example 12, N,N-dimethyl-3-amino-6chloro-2-hydroxybenzenesulfonamide (500 mg, 2 mmol) and 2-methylphenylisothiocyanate (298.4 mg, 2 mmol) were coupled to form the desired thiourea (557 mg, 70%). EI-MS m/z 400.0 (M$^{30}$).

b) N-(2-Methylphenyl)-N'-[4-chloro-2-tert-butyldimethylsilyloxy-3-(N",N"-dimethylaminosulfonyl)phenyl]thiourea Following the general procedure for protected phenyl thiourea formation outlined in example 12, N-[4-Chloro-2-hydroxy-3-[N",N"-dimethylaminosulfonyl]phenyl]-N'-(2-methylphenyl)thiourea (557 mg, 1.39 mmol), tert-butyldimethylsilyl chloride (1.04 mg, 6.95 mmol) and imidazole (189 mg, 2.78 mmol) were reacted to form the desired product (410 mg, 57%). EI-MS m/z 514.2 (M$^+$).

c) N-(2-Methylphenyl)-N'-[4-chloro-2-tert-butyldimethylsilyloxy-3-(N",N"-dimethylaminosulfonyl)phenyl]carbodiimide Following the general procedure for carbodiimide formation outlined in example 12, N-(2-methylphenyl)-N'-[4-chloro-2-tert-butyldimethylsilyloxy-3-(N",N"-dimethylaminosulfonyl)phenyl]thiourea (410 mg, 0.8 mmol), methanesulfonyl chloride (0.14 mL, 1.6 mmol) and triethylamine (0.23 mL, 1.6 mmol) were reacted to form the desired product (400 mg, crude). $^1$H NMR (CDCl$_3$) δ 0.39 (s, 6H), 1.05 (s, 9H), 1.72 (m, 4H), 2.37 (s, 3H), 2.87 (s, 6H), 7.04 (d, 1H), 7.18 (m, 4H), 7.29 (d, 1H).

d) Preparation of N-[4-Chloro2-hydroxy-3-(N",N"-dimethylaminosulfonyl)phenyl]-N'-(2-methylphenyl)cyanoguanidine Following the general procedure for cyanoguanidine formation outlined in example 12, N-[4-chloro-2-tert-butyldimethylsilyloxy-3-(N",N"-dimethylaminosulfonyl)phenyl]-N'-(2-methylphenyl)carbodiimide (400 mg, 0.83 mmol), cyanamide (139.4 mg, 3.32 mmol) and N,N-diisopropylethylamine (129 mg, 1.0 mmol) were reacted, followed by desilylation with Cesium fluoride (152 mg, 1.0 mmol) to form the desired product (110 mg, 32%). EI-MS m/z 408.2 (M$^+$). $^1$H NMR (DMSO-d$_6$) δ 2.22 (s, 3H), 2.86 (s, 6H), 7.20 (m, 5H), 7.60 (d, 1H), 8.63(s, 1H), 8.96 (s, 1H), 10.50 (s, 1H).

Example 17

Preparation of N-[4-Chloro-2-hydroxy-3-(N",N"-dimethylaminosulfonyl)phenyl]-N'-(2-fluorophenyl)cyanoguanidine a) 2-Fluorophenylisothiocyanate Into a solution of 2-fluoroaniline (1.0 g, 9.0 mmol) in 30 mL of toluene at room temperature, thiophosgene (1.06 mL, 13.5 mmol) and triethylamine (1.55 mL, 13.5 mmol) was added. The mixture was stirred at room temperature for 16 hours. The mixture was partitioned between ethyl acetate and water. The combined organic layer was then concentrated to give the desired product (1.05 g, 76%). $^1$H NMR (CDCl$_3$) δ 7.1–7.3 (m, 4H).

b) N-[4-Chloro-2-hydroxy-3-(N",N"-dimethyl-aminosulfonyl)phenyl]-N'-(2-fluorolphenyl)thiourea Following the general procedure for thiourea formation outlined in example 12, N,N-dimethyl-3-amino-6-chloro-2-hydroxybenzenesulfonamide (500 mg, 2 mmol) and 2-fluorophenylisothiocyanate (306 mg, 2 mmol) were coupled to form the desired thiourea (497 mg, 62%). EI-MS m/z 404.2 (M$^+$).

c) N-(2-Fluorophenyl)-N'-[4-chloro-2-tert-butyldimethylsilyloxy-3-(N",N"-dimethylaminosulfonyl)phenyl]thiourea Following the general procedure for protected phenyl thiourea formation outlined in example 12, N-[4-chloro-2-hydroxy-3-(N",N"-dimethylaminosulfonyl)phenyl]-N'-(2-fluorophenyl)thiourea (440 mg, 1.09 mmol), tert-butyldimethylsilyl chloride (817 mg, 5.45 mmol) and imidazole (148 mg, 2.18 mmol) were reacted to form the desired product (387 mg, 69%). EI-MS m/z 518.2 (M$^+$).

d) N-(2-Fluorophenyl)-N'-[4-chloro-2-tert-butyldimethylsilyloxy-3-(N",N"-dimethylaminosulfonyl)phenyl]carbodiimide Following the general procedure for carbodiimide formation outlined in example 12, N-(2-fluorophenyl)-N'-[4-chloro-2-tert-butyldimethylsilyloxy-3-(N",N"-dimethylaminosulfonyl)phenyl]thiourea (357 mg, 0.69 mmol), methanesulfonyl chloride (0.12 mL, 1.38 mmol) and triethylamine (0.2 mL, 1.38 mmol) were reacted to form the desired product (350 mg, crude). $^1$H NMR (CDCl$_3$) δ 0.38 (s, 6H), 1.05 (s, 9H), 1.72 (m, 4H), 2.87 (s, 6H), 7.06 (d, 1H), 7.19 (m, 3H), 7.28 (d, 1H), 7.31 (d, 1H).

e) Preparation of N-[4-Chloro-2-hydroxy-3-(N",N"-dimethylaminosulfonyl)phenyl]-N'-(2-fluorophenyl)cyanoguanidine Following the general procedure for cyanoguanidine formation outlined in example 12, N-[4-chloro-2-tert-butyldimethylsilyloxy-3-(N",N"-dimethylaminosulfonyl)phenyl]-N'-(2-fluorophenyl)carbodiimide (350 mg, 0.72 mmol), cyanamide (121 mg, 2.88 mmol) and N,N-diisopropylethylamine (111 mg, 0.86 mmol) were reacted, followed by desilylation with Cesium fluoride (132 mg, 0.86 mmol) to form the desired product (120 mg, 40%). EI-MS m/z 412.2 (M$^+$). $^1$H NMR (DMSO-d$_6$) δ 2.86 (s, 6H), 7.20 (m, 2H), 7.27 (m, 2H), 7.40 (t, 1H), 7.52 (d, 1H), 9.06 (s, 1H), 9.20 (s, 1H), 10.51 (s, 1H).

Example 18

Preparation of N-[4-Chloro-2-hydroxy-3-(N",N"-dimethylaminosulfonyl)phenyl]-N'-(2,3-difluorophenyl)cyanoguanidine a) 2,3-Difluorophenylisothiocyanate Into a solution of 2,3-difluoroaniline (1.0 g, 7.74 mmol) in 30 mL of toluene at room temperature, thiophosgene (0.91 mL, 11.6 mmol) and triethylamine (1.3 mL, 11.6 mmol) was added. The mixture was stirred at room temperature for 16 hours. The mixture was partitioned between ethyl acetate and water. The combined organic layer was then concentrated to give the desired product (910 mg, 68%). $^1$H NMR (CDCl$_3$) δ 6.98 (m, 2H), 7.11 (m, 1H).

b) N-[4-Chloro-2-hydroxy-3-(N",N"-dimethylaminosulfonyl)phenyl]-N'-(2,3-difluorophenyl)thiourea Following the general procedure for thiourea formation outlined in example 12, N,N-dimethyl-3-amino-6-chloro-2-hydroxybenzenesulfonamide (500 mg, 2 mmol) and 2,3-difluorophenylisothiocyanate (342 mg, 2 mmol) were coupled to form the desired thiourea (467 mg, 54%). EI-MS m/z 422.2 (M$^+$).

c) N-(2,3-Difluorophenyl)-N'-[4-chloro-2-tert-butyldimethylsilyloxy-3-(N",N"-dimethylaminosulfonyl)phenyl]thiourea Following the general procedure for protected phenyl thiourea formation outlined in example 12, N-[4-chloro-2-hydroxy-3-(N",N"-dimethylaminosulfonyl)phenyl]-N'-(2,3-difluorophenyl)thiourea (418 mg, 1.0 mmol), tert-butyldimethylsilyl chloride (745 mg, 5.0 mmol) and imidazole (136 mg, 2.0 mmol) were reacted to form the desired product (347 mg, 65%). EI-MS m/z 536.2 (M$^+$).

d) N-(2,3-Difluorophenyl)-N'-[4-chloro-2-tert-butyldimethylsilyloxy-3-(N",N"-dimethylaminosulfonyl)phenyl]carbodiimide Following the general procedure for carbodiimide formation outlined in example 12, N-(2,3-difluorophenyl)-N'-[4-chloro-2-tert-butyldimethylsilyloxy-3-(N",N"-dimethylaminosulfonyl)phenyl]thiourea (347 mg, 0.69 mmol), methanesulfonyl chloride (0.12 mL, 1.38 mmol) and triethylamine (0.2 mL, 1.04 mmol) were reacted to form the desired product (340 mg, crude). $^1$H NMR (CDCl$_3$) δ 0.39 (s, 6H), 1.03 (s, 9H), 2.86 (s, 6H), 6.95 (t, 1H), 7.03 (m, 2H), 7.08 (d, 1H), 7.31 (d, 1H).

e) Preparation of N-[4-Chloro-2-hydroxy-3-(N",N"-dimethylaminosulfonyl)phenyl]-N'-(2,3-difluorophenyl)cyanoguanidine Following the general procedure for cyanoguanidine formation outlined in example 12, N-[4-chloro-2-tert-butyldimethylsilyloxy-3-(N",N"-dimethylaminosulfonyl)phenyl]-N'-(2,3-difluorophenyl)carbodiimide (340 mg, 0.68 mmol), cyanamide (114 mg, 2.72 mmol) and N,N-diisopropylethylamine (106 mg, 0.82 mmol) were reacted, followed by desilylation with Cesium fluoride (124 mg, 0.82 mmol) to form the desired product (10 mg, 3.4%). EI-MS m/z 430.0 (M$^+$). $^1$H NMR (DMSO-d$_6$) δ 2.87 (s, 6H), 7.21 (m, 3H), 7.30 (m, 1H), 7.54 (d, 1H), 9.2 (s, 1H), 10.54 (s, 1H).

Example 19

Preparation of N-[4-Chloro-2-hydroxy-3-(N",N"-dimethylaminosulfonyl)phenyl]-N'-(2-methyl-3-fluorophenyl)cyanoguanidine a) 2-Methyl-3-fluorophenylisothiocyanate Into a solution of 2-methyl-3-fluoroaniline (1.0 g, 8.0 mmol) in 30 mL of toluene at room temperature, thiophosgene (0.94 mL, 12 mmol) and triethylamine (1.34 mL, 12 mmol) was added. The mixture was stirred at room temperature for 16 hours. The mixture was partitioned between ethyl acetate and water. The combined organic layer was then concentrated to give the desired product (1.1 g, 82%). EI-MS m/z 168.2 (M$^+$).

b) N-[4Chloro-2-hydroxy-3-(N",N"-dimethylaminosulfonyl)phenyl]-N'-2-methyl-3-fluorophenyl)thiourea Following the general procedure for thiourea formation outlined in example 12, N,N-dimethyl-3-amino-6-chloro-2-hydroxybenzenesulfonamide (560 mg, 2.23 mmol) and 2-methyl-3-fluorophenylisothiocyanate (372 mg, 2.23 mmol) were coupled to form the desired thiourea (570 mg, 61%). EI-MS m/z 418.2 (M$^+$).

c) N-(2-Methyl-3-fluorophenyl)-N'-[4-chloro-2-tert-butyldimethylsilyloxy-3-(N",N"-dimethylaminosulfonyl)phenyl]thiourea Following the general procedure for protected phenyl thiourea formation outlined in example 12, N-[4-chloro-2-hydroxy-3-(N",N"-dimethylaminosulfonyl)phenyl]-N'-(2-methyl-3-fluorophenyl)thiourea (530 mg, 1.27 mmol), tert-butyldimethylsilyl chloride (951 mg, 6.35 mmol) and imidazole (173 mg, 2.54 mmol) were reacted to form the desired product (331 mg, 49%). EI-MS m/z 532.2 (M$^+$).

d) N-(2-Methyl-3-fluorophenyl-N'-[4-chloro-2-tert-butyldimethylsilyloxy-3-(N",N"-dimethylaminosulfonyl)phenyl]carbodiimide Following the general procedure for carbodiimide formation outlined in example 12, N-(2-methyl-3-fluorophenyl)-N'-[4-chloro-2-tert-butyldimethylsilyloxy-3-(N",N"-dimethylaminosulfonyl)phenyl]thiourea (330 mg, 0.62 mmol), methanesulfonyl chloride (0.12 mL, 1.38 mmol) and triethylamine (0.2 mL, 1.04 mmol) were reacted to form the desired product (320 mg, crude). $^1$H NMR (CDCl$_3$) δ 0.38 (s, 6H), 1.05 (s, 9H), 2.28 (s, 3H), 2.85 (s, 6H), 6.89 (t, 1H), 6.93 (d, 1H), 7.05 (d, 1H), 7.13 (m, 1H), 7.19 (d, 1H).

f) Preparation of N-[4-Chloro-2-hydroxy-3-(N",N"-dimethylaminosulfonyl)phenyl]-N'-(2-methyl-3-fluorophenyl)cyanoguanidine Following the general procedure for cyanoguanidine formation outlined in example 12, N-[4-chloro-2-tertbutyldimethylsilyloxy-3-(N",N"-dimethylaminosulfonyl)phenyl]-N'-(2-methyl-3-fluorophenyl)carbodiimide (320 mg, 0.64 mmol), cyanamide (108 mg, 2.56 mmol) and N,N-diisopropylethylamine (99 mg, 0.77 mmol) were reacted, followed by desilylation with Cesium fluoride (117 mg, 0.77 mmol) to form the desired product (120 mg, 44%). EI-MS m/z 426.2 (M+). $^1$H NMR (DMSO-d$_6$) δ 2.12 (s, 3H), 2.86 (s, 6H), 7.09 (m, 3H), 7.22 (m, 1H), 7.56 (d, 1H), 8.82 (s, 1H), 9.10 (s, 1H), 10.51 (s, 1H).

Example 20

Preparation of N-[4-Chloro-2-hydroxy-3-(N",N"-dimethylaminosulfonyl)phenyl]-N'-(2-chloro-3-fluorophenyl)cyanoguanidine a) 2-Chloro-3-fluorobenzoic Acid A solution of 3-fluorobenzoic acid (8.0 g, 64.3 mmol) in 40 mL of THF was added dropwise to a solution of sec-butyllithium (90 mL, 128.6 mmol) and N,N,N',N'-tetramethylethylenediamine (20.0 mL, 147.9 mmol) in THF (100 mL) at −90° C. After addition, the reaction mixture was stirred at −90° C. for 30 minutes. Hexachloroethane (54 g, 257.2 mmol) in THF (100 mL) was added to reaction mixture dropwise. Then the reaction mixture was stirred at −78° C. to room temperature for 16 hours. The solvent was evaporated and the water was added to the residue. The reaction mixture was acidifed to PH=1 by added conc. hydrochloric acid. Then the reaction mixture was extracted with ether (3×). The combined organic phase was dried and conc. The crude product was washed with hexane for 3 times. Then it was filtered to get pure product (9.2 g, 93%). EI-MS m/z 172.89 (M−).

b) 2-Chloro-3-fluoroaniline

To a solution of 2-chloro-3-fluorobenzoic acid (4 g, 23 mmol) in CHCl$_3$ (50 mL), sulfonic acid (64 mL) was added and then sodium azide (2.62 g, 1.75 mmol) was added by portion. After addition, the reaction mixture was stirred at 50° C. for 16 hours. The solvent was evaporated and basicified with ammonium hydroxide at ice-bath. Then was extracted with ethyl acetate (3×). The combine organic phase was dried and conc. to give the desired product (2.61 g, 78%). LC-MS m/z 146.2 (M+).

c) 2-Chloro-3-fluorophenylisothiocyanate

Into a solution of 2-chloro-3-fluoroaniline (2.61 g, 17.94 mmol) in 50 mL of toluene at room temperature, thiophosgene (2.1 mL, 26.91 mmol) and triethylamine (3.02 mL, 26.91 mmol) was added. The mixture was stirred at room temperature for 16 hours. The mixture was partitioned between ethyl acetate and water. The combined organic layer was then concentrated to give the desired product (2.99 g, 89%). $^1$H NMR (CDCl$_3$) δ 7.10 (m, 1H), 7.22 (m, 1H).

d) N-[4Chloro-2-hydroxy-3-(N",N"-dimethylaminosulfonyl)phenyl]-N'-(2-chloro-3-fluorophenyl)thiourea Following the general procedure for thiourea formation outlined in example 12, N,N-dimethyl-3-amino-6-chloro-2-hydroxybenzenesulfonamide (500 mg, 2.0 mmol) and 2chloro-3-fluorophenylisothiocyanate (374 mg, 2.0 mmol) were coupled to form the desired thiourea (623 mg, 71%). LC-MS m/z 438.2 (M+).

e) N-(2-Chloro-3-fluorophenyl)-N'-[4-chloro-2-tert-butyldimethylsilyloxy-3-(N",N"-dimethylaminosulfonyl)phenyl]thiourea Following the general procedure for protected phenyl thiourea formation outlined in example 12, N-[4-chloro-2-hydroxy-3-(N",N"-dimethylaminosulfonyl)phenyl]-N'-(2-chloro-3-fluorophenyl)thiourea (575 mg, 1.32 mmol), tert-butyldimethylsilyl chloride (991 mg, 6.6 mmol) and imidazole (179 mg, 2.64 mmol) were reacted to form the desired product (367 mg, 50%). LC-MS m/z 552.2 (M+).

f) N-(2-Chloro-3-fluorophenyl-N'-[4-chloro-2-tert-butyldimethylsilyloxy-3-(N",N"-dimethylaminosulfonyl)phenyl]carbodiimide Following the general procedure for carbodiimide formation outlined in example 12, N-(2-chloro-3-fluorophenyl)-N'-[4-chloro-2-tert-butyldimethylsilyloxy-3-(N",N"-dimethylaminosulfonyl)phenyl]thiourea (367 mg, 0.67 mmol), methanesulfonyl chloride (0.12 mL, 1.38 mmol) and triethylamine (0.2 mL, 1.04 mmol) were reacted to form the desired product (360 mg, crude). $^1$H NMR (CDCl$_3$) δ 0.36 (s, 6H), 1.03 (s, 9H), 1.2.87 (s, 6H), 7.01 (m, 2H), 7.09 (d, 1H), 7.21 (m, 1H), 7.34 (d, 1H).

g) Preparation of N-[4-Chloro-2-hydroxy-3-(N",N"-dimethylaminosulfonyl)phenyl]-N'-(2-chloro-3-fluorophenyl)cyanoguanidine Following the general procedure for cyanoguanidine formation outlined in example 12, N-[4-chloro-2-tert-butyldimethylsilyloxy-3-(N",N"-dimethylaminosulfonyl)phenyl]-N'-(2-chloro-3-fluorophenyl)carbodiimide (360 mg, 0.7 mmol), cyanamide (118 mg, 2.8 mmol) and N,N-diisopropylethylamine (109 mg, 0.84 mmol) were reacted, followed by desilylation with Cesium fluoride (128 mg, 0.84 mmol) to form the desired product (120 mg, 39%). LC-MS m/z 446.2 (M+). $^1$H NMR (DMSO-d$_6$) δ 2.86 (s, 6H), 7.20 (d, 1H), 7.33 (t, 1H), 7.40 (m,2H), 7.58 (d, 1H), 9.11 (s, 1H), 9.31 (s, 1H), 10.52 (s, 1H).

Example 21

Preparation of N-[4-Chloro-2-hydroxy-3-(N",N"-dimethylaminosulfonyl)phenyl]-N'-(2-chloro4-fluorophenyl)cyanoguanidine a) 2-Chloro-4-fluorophenylisothiocyanate Into a solution of 2-chloro-4fluoroaniline (500 mg, 3.44 mmol) in a mixture of chloroform and water (10 mL/10 mL) at room temperature, thiophosgene (0.53 mL, 6.88 mmol) and sodium bicarbonate (1.09 g, 10.32 mmol) were added. The mixture was stirred at room temperature for 16 hours. The mixture was partitioned between chloroform and water. The combined organic layer was then concentrated to give the desired product (586 mg, 91%). $^1$H NMR (CDCl$_3$) δ 6.98 (m, 1H), 7.20 (m, 2H).

b) N-[4-Chloro-2-hydroxy-3-(N",N"-dimethylaminosulfonyl)phenyl]-N'-(2chloro-4-fluorophenyl)thiourea Following the general procedure for thiourea formation outlined in example 12, N,N-dimethyl-3-amino-6-chloro-2-hydroxybenzenesulfonamide (526 mg, 2.10 mmol) and 2-chloro-4-fluorophenylisothiocyanate (586 mg, 3.1 mmol) were coupled to form the desired thiourea (505 mg, 55%). EI-MS m/z 437.75 (M−).

c) N-(2-Chloro-4-fluorophenyl)-N'-[4-chloro-2-tert-butyldimethylsilyloxy-3-(N",N"-dimethylaminosulfonyl)phenyl]thiourea Following the general procedure for protected phenyl thiourea formation outlined in example 12, N-[4-chloro-2-hydroxy-3-(N",N"-dimethylaminosulfonyl)phenyl]-N'-(2-chlorofluorophenyl)thiourea (470 mg, 1.08 mmol), tert-butyldimethylsilyl chloride (810 mg, 5.4 mmol) and imidazole (147 mg, 2.16 mmol) were reacted to form the desired product (420 mg, 71%). EI-MS m/z 551.75 (M+).

d) N-(2-Chloro-4-fluorophenyl-N'-[4-chloro-2-tert-butyldimethylsilyloxy-3-(N",N"-dimethylaminosulfonyl)phenyl]carbodiimide Following the general procedure for carbodiimide formation outlined in example 12, N-(2-chloro4-fluorophenyl)-N'-

[4-chloro-2-tert-butyldimethylsilyloxy-3-(N",N"-dimethylaminosulfonyl)phenyl]thiourea (420 mg, 0.76 mmol), methanesulfonyl chloride (0.11 mL, 1.52 mmol) and triethylamine (0.22 mL, 1.52 mmol) were reacted to form the desired product (420 mg, crude). $^1$H NMR (CDCl$_3$) δ 0.36 (s, 6H), 1.02 (s, 9H), 2.89 (s, 6H), 6.99 (m, 1H), 7.08 (d, 1H), 7.19 (m, 2H), 7.33 (d, 1H).

e) Preparation of N-[4-Chloro-2-hydroxy-3-(N",N"-dimethylaminosulfonyl)phenyl]-N'-(2-chloro-4-fluorophenyl)cyanoguanidine Following the general procedure for cyanoguanidine formation outlined in example 12, N-[4-chloro-2-tert-butyldimethylsilyloxy-3-(N",N"-dimethylaminosulfonyl)phenyl]N'-(2-chloro4-fluorophenyl)carbodiimide (420 mg, 0.81 mmol), cyanamide (136 mg, 3.24 mmol) and N,N-diisopropylethylamine (126 mg, 1.62 mmol) were reacted, followed by desilylation with Cesium fluoride (148 mg, 1.62 mmol) to form the desired product (180 mg, 50%). EI-MS m/z 446.2 (M$^+$).

$^1$H NMR (CDCl$_3$) δ 2.86 (s, 6H), 7.16 (d, 1H), 7.24 (t, 1H), 7.46 (m, 1H), 7.55 (m, 2H), 8.94 (s, 1H), 9.15 (s, 1H), 10.50 (s, 1H).

Example 22

Preparation of N-(2-Chloro-4-fluorophenyl)-N'-[4-chloro-2hydroxy-3-(pipridone-4-ketone) aminosulfonylphenyl]cyanoguanidine a) N-(2-Chloro-4-fluorophenyl)-N'-[4-chloro-2-hydroxy-3-(piperidone-4-ketone)aminosulfonylphenyl]thiourea Following the general procedure for thiourea formation outlined in example 12, (N-piperidone-4-ketone)-2-hydroxy-3-amino-6-dichloro-benzenesulfonamide (732 mg, 2.4 mmol) and 2-chloro-4-fluorophenylisothiocyanate (see Example 46, 500 mg, 2.67 mmol) were coupled to form the desired thiourea (704 mg, 54%). EI-MS m/z 491.96 (M$^-$).

b) N-(2-Chloro-4-fluorophenyl)-N'-[4-chloro-2-tert-butyldimethylsilyloxy-3-(piperidone-4-ketone) aminosulfonylphenyl]thiourea Following the general procedure for protected phenyl thiourea formation outlined in example 12, N-(2-chlorofluorophenyl)-N'-[4-chloro-2-hydroxy-3-(piperidone-4-ketone)aminosulfonylphenyl]thiourea (704 mg, 1.44 mmol), tert-butyldimethylsilyl chloride (1.08 g, 7.2 mmol) and imidazole (196 mg, 2.88 mmol) were reacted to form the desired product (340 mg, 39%). LC-MS m/z 606.2 (M$^+$).

c) N-(2-Chloro-4-fluorophenyl)-N'-[chloro-2-tert-butyldimethylsilyloxy-3-(piperidone-4-ketone) aminosulfonylphenyl]carbodiimide Following the general procedure for carbodiimide formation outlined in example 12, N-(2-chloro-4-fluorophenyl)-N'-[4-chloro-2-tert-butyldimethylsilyloxy-3-(piperidone4-ketone)aminosulfonylphenyl]thiourea (340 mg, 0.56 mmol), methanesulfonyl chloride (0.08 mL, 1.12 mmol) and triethylamine (0.16 mL, 1.12 mmol) were reacted to form the desired product (330 mg, crude). LC-MS m/z 572.2 (M$^+$).

d) N-(2-Chloro-4-fluorophenyl)-N'-[4-chloro-2-hydroxy-3-(piperidone-4-ketone)aminosulfonylphenyl]cyanoguanidine Following the general procedure for cyanoguanidine formation outlined in example 12, N-(2-chloro4fluorophenyl)-N'-[4-chloro-2-tert-butyldimethylsilyloxy-3-(piperidone-4-ketone)aminosulfonylphenyl]carbodiimide (330 mg, 0.58 mmol), cyanamide (104 mg, 2.48 mmol) and N,N-diisopropylethylamine (96 mg, 0.74 mmol) were reacted, followed by desilylation with Cesium fluoride (113 mg, 0.74 mmol) to form the desired product (76 mg, 26%). LC-MS m/z 500.2. $^1$H NMR (DMSO-d$_6$) δ 2.44 (t, 4H), 3.64 (s, 4H), 7.19 (d, 1H), 7.25 (t, 1H), 7.46 (m, 1H), 7.58 (d, 2H), 8.93 (s, 1H), 9.20 (s, 1H), 10.53 (s, 1H).

Example 23

Preparation of N-(2,3-Dichlorophenyl)-N'-[4-chloro-2-hydroxy-3-(piperidone-4-ketone) aminosulfonylphenyl]cyanoguanidine a) N-(2,3-Dichlorophenyl)-N'-[4-chloro-2-hydroxy-3-(piperidone-4-ketone)aminosulfonylphenyl]thiourea Following the general procedure for thiourea formation outlined in example 12, (N-piperidone4-ketone)-2-hydroxy-3-amino-6-dichloro-benzenesulfonamide (1.0 g, 3.3 mmol) and 2,3-dichlorophenylisothiocyanate (669 mg, 3.3 mmol) were coupled to form the desired thiourea (500 mg, 30%). LC-MS m/z 508.2.

b) N-(2,3-Dichlorophenyl)-N'-[4-chloro-2-tert-butyldimethylsilyloxy-3-(piperidone-4-ketone) aminosulfonylphenyl]thiourea Following the general procedure for protected phenyl thiourea formation outlined in example 12, N-(2,3-dichlorophenyl)-N'-[4-chloro-2-hydroxy-3-(piperidone-4-ketone)aminosulfonylphenyl]thiourea (500 mg, 0.98 mmol), tert-butyldimethylsilyl chloride (765 mg, 4.9 mmol) and imidazole (140 mg, 1.98 mmol) were reacted to form the desired product (289 mg, 39%). LC-MS m/z 622.2 (M$^+$).

c) N-(2,3-Dichlorophenyl)-N'-[4-chloro-2-tert-butyldimethylsilyloxy-3-(piperidone-4-ketone) aminosulfonylphenyl]carbodiimide Following the general procedure for carbodiimide formation outlined in example 12, N-(2,3-dichlorophenyl)-N'-[4-chloro-2-tert-butyldimethylsilyloxy-3-(piperidone-4-ketone)aminosulfonylphenyl]thiourea (289 mg, 0.46 mmol), methanesulfonyl chloride (0.07 mL, 0.92 mmol) and triethylamine (0.13 mL, 0.92 mmol) were reacted to form the desired product (280 mg, crude). $^1$H NMR (CDCl$_3$) δ 0.36 (s, 6H), 1.03 (s, 9H), 2.54 (t, 4H), 3.63 (t, 4H), 7.09 (d, 1H), 7.1–7.27 (m, 2H), 7.32 (d, 1H), 7.38 (d, 1H).

d) N-(2,3-Dichlorophenyl)-N'-[4-chloro-2-hydroxy-3-(piperidone-4-ketone)aminosulfonylphenyl]cyanoguanidine Following the general procedure for cyanoguanidine formation outlined in example 12, N-(2,3-dichlorophenyl)-N'-[4-chloro-2-tert-butyldimethylsilyloxy-3-(piperidone-4-ketone)aminosulfonylphenyl]carbodiimide (280 mg, 0.48 mmol), cyanamide (80.6 mg, 1.92 mmol) and N,N-diisopropylethylamine (75 mg, 0.57 mmol) were reacted, followed by desilylation with Cesium fluoride (88 mg, 0.57 mmol) to form the desired product (40 mg, 16%). LC-MS m/z 500.2. $^1$H NMR (DMSO-d$_6$) δ 2.44 (t, 4H), 3.64 (s, 4H), 7.13 (m, 1H), 7.41 (m, 2H), 7.54 (m, 2H), 7.68 (d, 1H), 9.07 (s, 1H), 9.4 (s, 1H), 10.56 (s, 1H).

Example 24

Preparation of N-(2-Chloro-3-fluorophenyl)-N'-[4-chloro-2-hydroxy-3-(piperidone-4 ketone) aminosulfonylphenyl]cyanoguanidine a) N-(2-Chloro-3-fluorophenyl)-N'-[4-chloro-2-hydroxy-3-(piperidone-4-ketone)aminosulfonylphenyl]thiourea Following the general procedure for thiourea formation outlined in example 12,(N-piperidone-4-ketone)-2-hydroxy-3-amino-6-dichloro-benzenesulfonamide (908 mg, 3.3 mmol, not clean) and 2-chloro-3-fluorophenylisothiocyanate (See Example 45, 620 mg, 3.3 mmol) were coupled to form the desired thiourea (350 mg, 24%). LC-MS m/z 492.2.

b) N-(2-Chloro-3-fluorophenyl)-N'-[4-chloro-2-tert-butyldimethylsilyloxy-3-(piperidone-4-ketone) aminosulfonylphenyl]thiourea Following the general procedure for protected phenyl thiourea formation outlined in example 12, N-(2-chloro-3- fluorophenyl)-N'-[4-chloro-2-hydroxy-3-(piperidone-4-ketone)aminosulfonylphenyl]thiourea (350 mg, 0.71 mmol), tert-butyldimethylsilyl chloride (535 mg, 3.55 mmol) and imidazole (98 mg, 1.42 mmol) were reacted to form the desired product (280 mg, 65%). LC-MS m/z 606.2 (M$^+$).

c) N-(2-Chloro-3-fluorophenyl)-N'-[4-chloro-2-tert-butyldimethylsilyloxy-3-(piperidone-4-ketone)aminosulfonylphenyl]carbodiimide Following the general procedure for carbodiimide formation outlined in example 12, N-(2-chloro-3-fluorophenyl)-N'-[4-chloro-2-tert-butyldimethylsilyloxy-3-(piperidone-4-ketone)aminosulfonylphenyl]thiourea (280 mg, 0.46 mmol), methanesulfonyl chloride (0.07 mL, 0.92 mmol) and triethylamine (0.13 mL, 0.92 mmol) were reacted to form the desired product (280 mg, crude). $^1$H NMR (CDCl$_3$) δ 0.36 (s, 6H), 1.03 (s, 9H), 2.54 (t, 4H), 3.63 (t, 4H), 7.01 (d, 1H), 7.11 (d, 1H), 7.24 (m, 2H), 7.36 (d, 1H).

d) N-(2-Chloro-3-fluorophenyl)-N'-[4-chloro-2-hydroxy-3-(piperidone-4-ketone)aminosulfonylphenyl]cyanoguanidine Following the general procedure for cyanoguanidine formation outlined in example 12, N-(2-chloro-3-fluorophenyl)-N'-[4-chloro-2-tert-butyldimethylsilyloxy-3-(piperidone-4-ketone)aminosulfonylphenyl]carbodiimide (280 mg, 0.49 mmol), cyanamide (82.3 mg, 1.96 mmol) and N,N-diisopropylethylamine (75 mg, 0.57 mmol) were reacted, followed by desilylation with Cesium fluoride (88 mg, 0.57 mmol) to form the desired product (42 mg, 16%). LC-MS m/z 500.2. $^1$H NMR (DMSO-d$_6$) δ 2.44 (t, 4H), 3.64 (s, 4H), 7.2 (m, 1H), 7.22 (t, 1H), 7.34 (m, 3H), 7.58 (d, 1H), 9.1 (s, 1H), 9.3 (s, 1H), 10.57 (s, 1H).

Example 25

Preparation of N-(2-Bromo-3-fluorophenyl)-N'-[4-chloro-2-hydroxy-3-(piperidone-4-ketone) aminosulfonylphenyl]cyanoguanidine a) N-(2-Broom-3-fluorophenyl)-N'-[4-chloro-2-hydroxy-3-(piperidone-4-ketone)aminosulfonylphenyl]thiourea Following the general procedure for thiourea formation outlined in example 12,(N-piperidone-4-ketone)-2-hydroxy-3-amino-6-dichloro-benzenesulfonamide (1.5 g, 4.92 mmol, not clean) and 2-bromo-3-fluorophenyllisothiocyaniate (See Example 16, 1.0 g, 4.92 mmol) were coupled to form the desired thiourea (550 mg, 24%). EL-MS m/z 535.96 (M$^+$).

b) N-(2-Bromo-3-fluorophenyl)-N'-[4-chloro-2-tert-butyldimethylsilyloxy-3-(piperidone-4-ketone)aminosulfonylphenyl]thiourea Following the general procedure for protected phenyl thiourea formation outlined in example 12, N-(2-bromo-3-fluorophenyl)-N'-[4-chloro-2-hydroxy-3-(piperidone-4-ketone)aminosulfonylphenyl]thiourea (550 mg, 1.03 mmol), tert-butyldimethylsilyl chloride (773 mg, 5.15 mmol) and imidazole (142 mg, 2.06 mmol) were reacted to form the desired product (256 mg, 38%). LC-MS m/z 649.96 (M$^-$).

c) N-(2-Bromo-3-fluorophenyl)-N'-[4-chloro-2-tert-butyldimethylsilyloxy-3-(piperidone4-ketone)aminosulfonylphenyl]carbodiimide Following the general procedure for carbodiimide formation outlined in example 12, N-(2-bromo-3-fluorophenyl)-N'-[4-chloro-2-tert-butyldimethylsilyloxy-3-(piperidone-4-ketone)aminosulfonylphenyl]thiourea (256 mg, 0.4 mmol), methanesulfonyl chloride (0.07 mL, 0.92 mmol) and triethylamine (0.13 mL, 0.92 mmol) were reacted to form the desired product (256 mg, crude).). $^1$H NMR (CDCl$_3$) δ 0.36 (s, 6H), 1.03 (s, 9H), 2.54 (t, 4H), 3.63 (t, 4H), 6.96 (t, 1H), 7.0 (d, 1H), 7.10 (d, 1H), 7.24 (m, 1H), 7.39 (d, 1H).

d) N-(2-Bromo-3-fluorophenyl)-N'-[4-chloro-2-hydroxy-3-(piperidone-4-ketone)aminosulfonylphenyl]cyanoguanidine Following the general procedure for cyanoguanidine formation outlined in example 12, N-(2-bromo-3-fluorophenyl)-N'-[4-chloro-2-tert-butyldimethylsiyloxy-3-(piperidone-4-ketone)aminosulfonylphenyl]carbodiimide (256 mg, 0.42 mmol), cyanamide (82.3 mg, 1.96 mmol) and N,N-disopropylethylamine (75 mg, 0.57 mmol) were reacted, followed by desilylation with Cesium fluoride (88 mg, 0.57 mmol) to form the desired product (48 mg, 21%). LC-MS m/z 544.2. $^1$H NMR (DMSO-d$_6$) δ 2.44 (t, 4H), 3.64 (s, 4H), 7.10 (m, 1H), 7.28 (m, 2H), 7.42 (m, 1H), 7.59 (m, 1H), 9.02 (s, 1H), 9.53 (s, 1H), 10.5 (s, 1H).

Example 26

Preparation of N-(2-Bromophenyl)-N'-4-chloro-2-hydroxy-3-(homopiperazineaminosulfonylphenyl) phenyl]cyanoguanidine a) N-(3,4Dichlorophenyl)-2,2-dimethyl-propionamide 3,4-dichloroaniline (150 g) in TBME (1 L) was cooled to 10–15° C. 30% aq NaOH (141 g, 1.14 equiv) was added, and the solution stirred vigorously via overhead mechanical stirrer. Trimethylacetyl chloride ("PivCl", 126 mL) was added at such a rate as to keep the internal temperature below 30° C. During this addition, the solution mixture becomes thick with white solid product. When the addition was complete (10–15 min), the mixture was heated to 30–35° C. for 1 hr, and then allowed to cool. The reaction mixture was held at −5° C. (overnight), and then filtered, rinsing first with 90:10 water/MeOH (600 mL) and then water (900 mL). Drying under vacuum yielded 195 g (86%) product, as off-white crystals. LCMS m/z 246(M−H)$^+$.

b) 2-tert-Butyl-6-chloro-benzooxazole-7-sulfonyl Chloride

The solution of N3,4dichloro-phenyl)-2,2dimethyl-propionamide (10 g, 41 mmol) in dry THF (100 mL) was cooled to −72° C. under argon. n-Butyl lithium (1.6M in hexane, 64 mL, 102 mmol) was added dropwise. The solution warmed to ca. −50° C. over 45 minutes, and then was kept in the −25—−10° C. range for 2 hrs. The solution was then recooled to −78° C., and sulfur dioxide was bubbled through the solution for 30 min. The solution was then allowed to warm to room temperature for 2 h, and a Ar stream was bubbled through the solution, with a gas outlet provided so that any excess sulfur dioxide could escape during the warming. The THF solution was cooled in an ice bath, and sulfuryl chloride (3.58 mL, 44.9 mmol) was added dropwise. After a few minutes, the solution was warmed to room temperature for overnight. The mixture was concentrated, diluted with ethyl acetate and washed with water. Decolorizing carbon was added and the mixture was filtered. The resulting solution was dried (sodium sulfate), filtered and concentrated to afford the title compound (12.4 g, 98%). $^1$H NMR (CDCl$_3$) • 7.92 (d, 1H, J=8.5 Hz), 7.57 (d, 1H, J=8.4 Hz), 1.57 (s, 9H).

c) Homopiperazine-carboxylic Acid tert-Butyl Ester

To a solution of homopiperazine (5.0 g, 49.92 mmol) in dichloromethane (100 mL), Di-tert-butyl dicarbonate (3.63 g, 16.64 mmol) and triethylamine (6.96 mL, 49.92 mmol) were added at room temperature. Then the reaction mixture was stirred at room temperature for 16 hours. The solid was filtered and the organic phase was washed with water (3×). The organic phase was dried (sodium sulfate), filtered and concentrated to afford the title compound (6.5 g, 66%). EI-MS m/z 197.79(M$^-$).

General Procedure for the Synthesis of
Sulfonylamides d) 2-tert-Butyl-6-chloro-7-(homopiperazine-1-sulfonyl)-benzooxazole To a solution of 2-tert-butyl-6-chloro-benzooxazole-7-sulfonyl chloride (5.54, 18 mmol) and triethylamine (2.51 mL, 18 mmol) in THF (100 mL) at 0° C. was added homopiperazine-carboxylic acid tert-butyl ester (3.0 g, 15 mmol). The reaction was warmed to room temperature and allowed to stir overnight. The solution was concentrated and then diluted with water and extacted with ethyl acetate (3 times). The combined organic layers were dried with $MgSO_4$, filtered, and concentrated. Flash chromatography (80% ethyl acetate/20% Ethanol) on silica gel gave the title compound (4.0 g, 61%). LC-MS m/z 473.2.

General Procedure for the Hydrolysis of the
Benzooxazole to the Desired Aniline e) 6-Amino-3-chloro-2-(homopiperazine-1-sulfonyl)-phenol To a solution of 2-tert-Butyl-6-chloro-7-(homopiperazine-1-sulfonyl)-benzooxazole (2.0 g, 4.24 mmol) in 1,4-dioxane (56 mL) was treated with water (3.5 mL) and conc. $H_2SO_4$ (3.5 mL). The mixture was heated to 100° C. for 16 h. The reaction was cooled to room temperature, and then basified to pH=14 with 25% aq NaOH. washed. The mixture was extracted with ethyl acetate (3 times), dried with $MgSO_4$, filtered, and concentrated to afford the title compound (1.04 g, 80%). EI-MS m/z 306.2($M^+$).

General Procedure for the Protected Amine Group f) 6-Amino-3-chloro-2-[(4-N-9-fluorenylmethylformate)homopiperazine-1-sulfonyl)]-phenol To a solution of 6-Amino-3-chloro-2-(homopiperazine-1-sulfonyl)-phenol (1.0 g, 3.27 mmol) in 1,4-dioxane (30 mL), 10% of sodium carbonate (7.5 mL) was added. Then the reaction mixture was cooled down to 0° C., 9-fluorenylmethyl chloroformate (800 mg, 3.27 mmol) was added. After addition, the reaction mixture was stirred at 0° C. for 1 hour. The solvent was evaporated. The residue was partitioned between ethyl acetate and 10% of sodium carbonate. The combined organic phase was dried with $MgSO_4$, filtered, and concentrated to afford the tide compound (2.0 g, crude). EI-MS m/z 528.2($M^+$).

g) N-(2-Bromophenyl)-N'-[4-chloro-2-hydroxy-3-[(4N-9-fluorenylmethylformate)homopiperazine aminosulfonylphenyl]thiourea Following the general procedure for thiourea formation outlined in example 12, 6-Amino3-chloro-2-[(4N-9-fluorenylmethylformate)homopiperazine-1-sulfonyl)]-phenol (2.0 g, 3.79 mmol, not clean) and 2-bromophenylisothiocyanate (811 mg, 3.79 mmol) were coupled to form the desired thiourea (2.0 g, 71%). EI-MS m/z 740.61 ($M^-$).

h) N-(2-Bromophenyl)-N'-[4-chloro-2-tert-butyldimethylsilyloxy-3-[(4-N-9-fluorenylmethylformate)homopiperazine Aminosulfonylphenyl]thiourea Following the general procedure for protected phenyl thiourea formation outlined in example 12, N-(2-bromophenyl)-N'-[4-chloro-2-hydroxy-3-[(4-N-9-fluorenylmethylformate)homopiperazine aminosulfonylphenyl]thiourea (1.0 g, 1.35 mmol), tert-butyldimethylsilyl chloride (1.02 g, 6.75 mmol) and imidazole (184 mg, 2.7 mmol) were reacted to form the desired product (836 mg, 73%). EI-MS m/z 854.97 ($M^-$).

i) N-(2-Bromophenyl)-N'-[4-chloro-2-tert-butyldimethylsilyloxy-3-[(4-N-9-fluorenylmethylformate) homopiperazine Aminosulfonylphenyl]carbodiimide Following the general procedure for carbodiimide formation outlined in example 12, N-(2-bromophenyl)-N'-[4-chloro-2-tert-butyldimethylsilyloxy-3-[(4-N-9-fluorenylmethylformate)homopiperazine aminosulfonylphenyl]thiourea (836 mg, 0.98 mmol), methanesulfonyl chloride (0.15 mL, 1.96 mmol) and triethylamine (0.27 mL, 1.96 mmol) were reacted to form the desired product (772 mg, crude). $^1$H NMR ($CDCl_3$) δ 0.40 (s, 6H), 1.06 (s, 9H), 1.58 (t, 1H), 1.68 (m, 1H), 1.92 (t, 4H), 3.03 (q, 1H), 3.10 (t, 1H), 3.36 (m, 3H), 3.44 (m, 2H), 4.23 (t, 1H), 4.64 (d, 2H), 7.07 (d, 1H), 7.33 (m, 8H), 7.60 (m, 3H), 7.73 (m, 2H).

j) N-(2-Bromophenyl)-N'-[4-chloro-2-hydroxy-3-(homopiperazine Aminosulfonyl)phenyl]cyanoguanidine Following the general procedure for cyanoguanidine formation outlined in example 12, N2-bromophenyl)-N'-[4-chloro-2-tert-butyldimethylsilyloxy-3-[(4-N-9-fluorenylmethylformate)homopiperazine aminosulfonylphenyl]carbodiimide (256 mg, 0.42 mmol), cyanamide (82.3 mg, 1.96 mmol) and N,N-diisopropylethylamine (75 mg, 0.57 mmol) were reacted, followed by desilylation with Cesium fluoride (88 mg, 0.57 mmol) and deprotected amino with 20% piperidine (8 mL) in THF (40 mL) at room temperature for 30 minutes to form the desired product. The desired product (250 mg) was purified by Gilson HPLC to give pure product (50 mg, 20%). LC-MS m/z 527.2. $^1$H NMR (DMSO-$d_6$) δ 1.68 (m, 2H), 3.06 (m, 2H), 3.2 (m, 2H), 3.34 (m, 2H), 3.71 (m, 2H), 6.25 (m, 1H), 7.19 (m, 1H), 7.4 (m, 3H), 7.71 (m, 1H), 8.76 (s, 1H).

Example 27

Preparation of N-(2-Bromophenyl)-N'-[4-chloro-2-hydroxy -3-(N-methylhomopiperazine-aminosulfonylphenyl)phenyl]cyanoguanidine To a solution of N-(2-bromophenyl)-N'-[4-chloro-2-hydroxy-3-(homopiperazine-aminosulfonylphenyl)phenyl] cyanoguanidine (287 mg, 0.54 mmol) in diglyme (10 mL), paraformalde (35 mg, 1.08 mmol) and titanium isoproxide (0.17 mL, 0.54 mmol) were added at room temperature. The reaction mixture was stirred at 60° C. for 1 hour and stirred at room temperature for 30 minutes. Then sodium borohydride (22 mg, 0.65 mmol) was added and heated to 60° C. for 4 hours. The reaction mixture was partitioned between ethyl acetate and water. The combined organic phase was dried with $MgSO_4$, filtered, and concentrated to afford the The desired product. Then was purified by Gilson HPLC to give pure product (10 mg, 3%). LC-MS m/z 541.2. $^1$H NMR (DMSO-$d_6$) δ 1.7 (m, 2H), 2.65 (s, 3), 3.09 (m, 3H), 3.27 (m, 3H), 3.7 (m, 2H), 6.33 (d, 1H), 7.21 (t, 1H), 7.45 (m, 2H), 7.58 (d, 1H), 7.7 (d, 1H), 8.61 (s, 1H), 10.34 (s, 1H).

Example 28

Preparation of N-(2-Bromophenyl)-N'-[4-chloro-2-hydroxy-3-(piperazine-aminosulfonylphenyl)phenyl] cyanoguanidine a) 4(2-tert-Butyl-6-chloro-benzooxazole-7-sulfonyl)-piperazine-1-carboxylic Acid tert-Butyl Ester Following the general procedure for the synthesis of sulfonylamides outlined in example 51, 2-tert-butyl-6-chlorbenzooxazole-7-sulfonyl chloride (5.0 g, 16.2 mmol), triethylamine (2.4 mL, 17.2 mmol), and piperazine-carboxylic acid tert-butyl ester (3.62 g, 19.4 mmol) were reacted in THF (50 mL) to afford the title compound (5.44 g, 67%). LCMS m/z 402(M–H)+ (desired -Boc).

b) 6-Amino3chloro-2-(piperazine-1-sulfonyl)-phenol

Following the general procedure for the hydrolysis of the benzooxazole to the desired aniline outlined in example 51, 4(2-tert-butyl-6-chloro-benzooxazole-7-sulfonyl)-piperazine-1-carboxylic acid tert-butyl ester (2.0 g, 4.3 mmol), water (3.65 mL), and $H_2SO_4$ (3.65 mL) in 1,4-dioxane (60 mL) were reacted to afford the title compound (1.22 g, 96%). LCMS m/z 292(M–H)+.

c) 6-Amino-3-chloro-2-[(4-N-9-fluorenylmethylformate) piperazine-1-sulfonyl)]-phenol Following the general procedure for protection of amino outlined in example 51, 6Amino-3-chloro-2-(piperazine-1-sulfonyl)-phenol (660 mg, 2.26 mmol), 10% of sodium carbonate (6.0 mL) and 9-fluorenylmethyl chloroformate (584.7 mg, 2.26 mmol) in 1,4-dioxane (6.78 mL) were reacted to afford the title compound (1.22 g, crude). LC-MS m/z 514(M+).

d) N-(2-Bromophenyl)-N'-[4-chloro-2-hydroxy-3-[(4-N-9-fluorenylmethylformate)piperazine Aminosulfonylphenyl] thiourea Following the general procedure for thiourea formation outlined in example 12, 6-Amino-3-chloro-2-[(4-N-9-fluorenylmethylformate)piperazine-1-sulfonyl)]-phenol (1.22 g, 2.4 mmol, not clean) and 2-bromophenylisothiocyanate (508 mg, 2.4 mmol) were coupled to form the desired thiourea (490 mg, 28%). EL-MS m/z 727.07 (M−).

e) N-(2-Bromophenyl)-N'-[4-chloro-2-tert-butyldimethylsilyloxy-3-[(4-N-9-fluorenylmethylformate) piperazine Aminosulfonylphenyl]thiourea Following the general procedure for protected phenyl thiourea formation outlined in example 12, N-(2-bromophenyl)-N'-[4-chloro-2-hydroxy-3-[(4-N-9-fluorenylmethylformate)piperazine aminosulfonylphenyl] thiourea (490 mg, 0.67 mmol), tert-butyldimethylsilyl chloride (505 mg, 3.35 mmol) and imidazole (93 mg, 1.34 mmol) were reacted to form the desired product (407 mg, 73%). EI-MS m/z 841.08 (M+).

f) N-(2-Bromophenyl)-N'-[4-chloro-2-tert-butyldimethylsilyloxy-3-[(4-N-9-fluorenylmethylformate) piperazine Aminosulfonylphenyl]carbodiimide Following the general procedure for carbodiimide formation outlined in example 12, N-(2-bromophenyl)-N'-4-chloro-2-tert-butyldimethylsilyloxy-3-[(4-N-9-fluorenylmethylformate)piperazine aminosulfonylphenyl] thiourea (640 mg, 0.76 mmol), methanesulfonyl chloride (0.13 mL, 1.52 mmol) and triethylamine (0.25 mL, 1.52 mmol) were reacted. to form the desired product (640 mg, crude). $^1$H NMR (CDCl$_3$) δ 0.4 (s, 6H), 1.1 (s, 9H), 3.2 (m, 4H), 3.48 (m, 4H), 4.22 (t, 1H), 4.51 (d, 2H), 7.07–7.44 (m, 9H), 7.54 (d, 2H), 7.6 (d, 1H), 7.74 (d, 2H).

g) N-(2-Bromophenyl)-N'-[4-chloro-2-hydroxy-3-(piperazine Aminosulfonyl)phenyl]cyanoguanidine Following the general procedure for cyanoguanidine formation outlined in example 12, N-(2-bromophenyl)-N'-[4-chloro-2-tert-butyldimethylsilyloxy-3-[(4-N-9-fluorenylmethylformate)piperazine aminosulfonylphenyl] carbodiimide (640 mg, 0.79 mmol), cyanamide (133 mg, 3.16 mmol) and N,N-diisopropylethylamine (122 mg, 0.95 mmol) were reacted, followed by desilylation with Cesium fluoride (144 mg, 0.95 mmol) and deprotected amino with 20% piperidine (8 mL) in THF (40 mL) at room temperature for 30 minutes to form the desired product(purified by Gilson HPLC, 346 mg, 76%). LC-MS m/z 513.2. $^1$H NMR (DMSO-d$_6$) δ 3.02 (t, 4H), 3.43 (t, 4H), 6.08 (d, 1H), 7.2 (m, 1H), 7.38 (m, 3H), 7.67 (d, 1H), 8.84 (s, 1H).

Example 29

Preparation of N-(2-Chloro-3-fluorophenyl)-N'-[4-chloro-2-hydroxy -3-(piperazine-aminosulfonylpheny)phenyl]cyanoguanidine a) N-(2-Chloro-3-fluorophenyl)-N'-[4-chloro-2-hydroxy-3-[4-N-9-fluorenylmethylformate)piperazine Aminosulfonylphenyl]thiourea Following the general procedure for thiourea formation outlined in example 12, 6Amino-3-chloro-2-[(4-N-9-fluorenylmethylformate)piperazine-1-sulfonyl)]-phenol (1.0 g, 1.94 mmol, not clean) and 2-chloro-3-fluorophenylisothiocyanate (See Example 45, 400 mg, 1.94 mmol) were coupled to form the desired thiourea (713 mg, 48%). EL-MS m/z 700.70 (M−).

b) N-(2-Chloro-3-fluorophenyl)-N'-[4-chloro-2-tert-butyldimethylsilyloxy-3-[(4-N-9-fluorenylmethylformate) piperazine Aminosulfonylphenyl]thiourea Following the general procedure for protected phenyl thiourea formation outlined in example 12, N-(2-chloro-3-fluorophenyl)-N'-[4-chloro-2-hydroxy-3-[(4-N-9-fluorenylmethylformate)piperazine aminosulfonylphenyl] thiourea (713 mg, 1.02 mmol), tert-butyldimethylsilyl chloride (765 mg, 5.1 mmol) and imidazole (139 mg, 2.04 mmol) were reacted to form the desired product (455 mg, 55%). EI-MS m/z 814.68 (M−).

c) N-(2-Chloro-3-fluorophenyl)-N'-[4-chloro-2-tert-butyldimethylsilyloxy-3-[(4-N-9-fluorenylmethylformate) piperazine Aminosulfonylphenyl]carbodiimide Following the general procedure for carbodiimide formation outlined in example 12, N-(2-chloro-3-fluorophenyl)-N'-[4-chloro-2-tert-butyldimethylsilyloxy-3-[(4-N-9-fluorenylmethylformate)piperazine aminosulfonylphenyl] thiourea (455 mg, 0.56 mmol), methanesulfonyl chloride (0.1 mL, 1.12 mmol) and triethylamine (0.18 mL, 1.12 mmol) were reacted to form the desired product (537 mg, crude). $^1$H NMR (CDCl$_3$) δ 0.39 (s, 6H), 1.04 (s, 9H), 3.19 (m, 4H), 3.49 (m, 4H), 4.23 (t, 1H), 4.5 (d, 1H), 6.96 (t, 1H), 7.01–7.41 (m, 9H), 7.55 (d, 1H), 7.74 (d, 1H).

d) N-(2-Chloro-3-fluorophenyl)-N'-[4-chloro-2-hydroxy-3-(piperazine Aminosulfonyl)phenyl]cyanoguanidine Following the general procedure for cyanoguanidine formation outlined in example 12, N-(2-chloro-3-fluorophenyl)-N'-[4-chloro-2-tert-butydimethylsilyloxy-3-[(4-N-9-fluorenylmethylformate)piperazine aminosulfonylphenyl]carbodiimide (537 mg, 0.69 mmol), cyanamide (116 mg, 2.76 mmol) and N,N-diisopropylethylamine (107 mg, 0.83 mmol) were reacted, followed by desilylation with Cesium fluoride (126 mg, 0.83 mmol) and deprotected amino with 20% piperidine (6 mL) in THF (30 mL) at room temperature for 30 minutes to form the desired product(purified by Gilson HPLC, 45 mg, 14%). LC-MS m/z 487.0. $^1$H NMR (DMSO-d$_6$) δ 3.02 (t, 4H), 3.43 (t, 4H), 6.2 (d, 1H), 7.2–7.39 (m, 4H), 9.03 (s, 1H).

Example 30

Preparation of N-(2-Bromophenyl)-N'-[4-chloro-2-hydroxy-3-(4-amino-piperidine Aminosulfonyl)phenyl)phenyl]cyanoguanidine a) [1-(2tert-Butyl-6-chloro-berizooxazole-7-sulfonyl)-piperidin-4-yl]-carbamic Acid tert-Butyl Ester Following the general procedure for the synthesis of sulfonylamides outlined in example 51, 2-tert-butyl-6-chloro-benzooxazole-7-sulfonyl chloride (5.05 g, 16.4 mmol), triethylamine (4.57 mL, 32.8 mmol), and 4-N-Boc-aminopiperidine (3.288 g, 16.4 mmol) were reacted in THF (125 mL) to afford the title compound (4.18 g, 54%). $^1$H NMR (DMSO-d$_6$) • 7.98 (d, 1H, J=8.48 Hz), 7.63 (d, 1H, J=8.47 Hz), 3.73 (d, 2H), 3.35 (bs, 2H), 2.92 (m, 2H), 1.75 (d, 2H), 1.35 (s, 10H).

b) 6-Amino-2-(4-amino-piperidine-1-sulfonyl)-3-chloro-phenol

Following the general procedure for the hydrolysis of the benzooxazole to the desired aniline outlined in example 51, [1-(2-tert-butyl-6-chloro-benzooxazole-7-sulfonyl)-piperidin4-yl]-carbamic acid tert-butyl ester (4.18 g, 8.86 mmol), water (5.5 mL), and H$_2$SO$_4$ (5.5 mL) in 1,4-dioxane (55mL) were reacted to afford the title compound (2.03 g, 75%). LCMS m/z 306(M–H)$^+$.

c) 6-Amino-3-chloro-2-[(4-N-9-fluorenylmethylformate) piperidin-1-sulfonyl)]-phenol Following the general procedure for protection of amino outlined in example 51, 6Amino-3-chloro-2-(piperidin-1-sulfonyl)-phenol (1.05 g, 3.43 mmol), 10% of sodium carbonate (9.1 mL) and 9-fluorenylmethyl chloroformate (887.4 mg, 3.43 mmol) in 1,4-dioxane (10.3 mL) were reacted to afford the title compound (1.3 g, crude). LC-MS m/z 528.04(M$^+$).

d) N-(2-Bromophenyl)-N'-[4-chloro-2-hydroxy-3-[(4-N-9-fluorenylmethylformate)piperidine Aminosulfonylphenyl] thiourea Following the general procedure for thiourea formation outlined in example 12, 6Amino-3-chloro-2-[(4N-9-fluorenylmethylformate)piperidine-1-sulfonyl)]-phenol (1.3 g, 2.42 mmol, not clean) and 2-bromophenylisothiocyanate (520 mg, 2.42 mmol) were coupled to form the desired thiourea (700 mg, 39%). EL-MS m/z 739.07 (M$^-$).

e) N-(2-Bromophenyl)-N'-[4-chloro-2-tert-butyldimethylsilyloxy-3-[(4-N-9-fluorenylmethylformate) piperidine Aminosulfonylphenyl]thiourea Following the general procedure for protected phenyl thiourea formation outlined in example 12, N-(2-bromophenyl)-N'-[4-chloro-2-hydroxy-3-[(4-N-9-fluorenylmethylformate)piperazine aminosulfonylphenyl] thiourea (700 mg, 0.95 mmol), tert-butyldimethylsilyl chloride (713 mg, 4.75 mmol) and imidazole (131 mg, 1.9 mmol) were reacted to form the desired product (400 mg, 50%). EI-MS m/z 854.52 (M$^-$).

f) N-(2-Bromophenyl)-N'-[4-chloro-2-tert-butyldimethylsilyloxy-3-[(4-N-9-fluorenylmethylformate) piperidine Aminosulfonylphenyl]carbodiimide Following the general procedure for carbodiimide formation outlined in example 12, N-(2-bromophenyl)-N'-[4-chloro-2-tert-butyldimethylsilyloxy-3-[(4-N-9-fluorenylmethylformate)piperidine aminosulfonylphenyl] thiourea (374 mg, 0.57 mmol), methanesulfonyl chloride (0.1 mL, 1.12 mmol) and triethylamine (0.18 mL, 1.12 mmol) were reacted to form the desired product (374 mg, crude). $^1$H NMR (CDCl$_3$) δ 0.38 (s, 6H), 1.03 (s, 9H), 1.49 (m, 2H), 1.93 (m, 2H), 2.89 (t, 2H), 3.72 (m, 2H), 4.2 (t, 1H), 4.4 (d, 2H), 4.73 (d, 1H), 7.06–7.34 (m, 8H), 7.41 (t, 2H), 7.61 (t, 2H), 7.24 (m, 1H), 7.76 (d, 2H).

g) N-(2-Bromophenyl)-N'-[4-chloro-2-hydroxy-3-(piperidine Aminosulfonyl)phenyl]cyanoguanidine Following the general procedure for cyanoguanidine formation outlined in example 12, N-(2-bromophenyl)-N'-[4-chloro-2-tert-butyldimethylsilyloxy-3-[(4-N-9-fluorenylmethylformate)piperidine aminosulfonylphenyl] carbodiimide (400 mg, 0.65 mmol), cyanamide (108 mg, 2.6 mmol) and N,N-diisopropylethylamine (99 mg, 0.78 mmol) were reacted, followed by desilylation with Cesium fluoride (123 mg, 0.78 mmol) and deprotected amino with 20% piperidine (4 mL) in THF (20 mL) at room temperature for 30 minutes to form the desired product(purified by Gilson HPLC, 105 mg, 41%). LC-MS m/z 527.2. $^1$H NMR (DMSO-d$_6$) δ 1.43 (m, 2H), 1.83 (m, 2H), 2.9 (t, 2H), 2.95 (m, 2H), 3.66 (d, 2H), 6.09 (d, 1H), 7.14 (t, 1H), 7.34 (m, 3H), 7.64 (d, 1H).

Example 31

Preparation of N-(2-Bromophenyl)-N'-{4-chloro-2-hydroxy -3-[(R)-3-amino-pyrrolidine] aminosulfonylphenyl)phenyl}cyanoguanidine a) [(R)-1-(2-tert-Butyl-6-chloro-benzooxazole-7-sulfonyl)-pyrrolidin-3-yl]-carbamic Acid tert-Butyl Ester Following the general procedure for the synthesis of sulfonylamides outlined in example 51, 2-tert-butyl-6-chloro-benzooxazole-7-sulfonyl chloride (3.0 g, 9.74 mmol), triethylamine (1.63 mL, 11.7 mmol), and (R)-pyrrolidin-3-yl-carbamic acid tert-butyl ester (2.18 g, 11.7 mmol) were reacted in THF (30 mL) to afford the title compound (3.0 g, 67%). $^1$H NMR (CDCl$_3$) • 7.77 (d, 1H, J=8.5 Hz), 7.48 (d, 1H, J=8.5 Hz), 4.67 (bm, 1H), 4.22 (bm, 1H), 3.66 (bm, 2H), 3.52 (bm, 1H), 3.41 (bm, 1H), 2.19 (bm, 1H), 1.90 (bm, 1H), 1.48 (s, 9H).

b) 6-Amino-2-((R)-3-amino-pyrrolidine-1-sulfonyl)-3-chloro-phenol

Following the general procedure for the hydrolysis of the benzooxazole to the desired aniline outlined in example 51, [(R)-1-(2-tert-butyl-6-chloro-benzooxazole-7-sulfonyl)-pyrrolidin-3-yl]-carbamic acid tert-butyl ester (2.0 g, 4.31 mmol), water (3.6 mL), and H$_2$SO$_4$ (3.6 mL) in 1,4-dioxane (60 mL) were reacted to afford the title compound (1.2 g, 94%). LCMS m/z 292(M–H)$^+$.

c) 6-Amino-3-chloro-2-[(R)-3-N-9-fluorenylmethylformate)pyrrolidine -1-sulfonyl)]-phenol Following the general procedure for protection of amino outlined in example 51, 6Amino-2-((R)-3-amino-pyrrolidine-1-sulfonyl)-3-chloro-phenol (907 mg, 3.1 mmol), 10% of sodium carbonate (7.5 mL) and 9-fluorenylmethyl chloroformate(802 mg, 3.1 mmol) in 1,4-dioxane (20 mL) were reacted to afford the title compound (1.7 g, crude). LC-MS m/z 514.2 (M$^+$).

d) N-(2-Bromophenyl)-N'-{chloro-2-hydroxy-3-[(R)-3-N-9-fluorenylmethylformate)pyrrolidine]aminosulfonyl-phenyl}thiourea Following the general procedure for thiourea formation outlined in example 12, 6-Amino-3-chloro-2-[(R)-3-N-9-fluorenylmethylformate)pyrrolidine-1-sulfonyl)]-phenol (800 mg, 1.56 mmol, not clean) and 2-bromophenylisothiocyanate (333 mg, 1.56 mmol) were coupled to form the desired thiourea (405 mg, 36%). EL-MS m/z 727.01 (M$^+$).

e) N-(2-Bromophenyl)-N'-{4-chloro-2-tert-butyldimethylsilyloxy-3-[(R)-3-N-9-fluorenylmethyl-formate)pyrrolidine]aminosulfonylphenyl}thiourea Following the general procedure for protected phenyl thiourea formation outlined in example 12, N-(2-bromophenyl)-N'-{4-chloro-2-hydroxy-3-[(R)-3-N-9-fluorenylmethylformate)pyrrolidine]aminosulfonyl-phenyl}thiourea (405 mg, 0.56 mmol), tert-butyldimethylsilyl chloride (420 mg, 2.8 mmol) and imidazole (76 mg, 1.12 mmol) were reacted to form the desired product (293 mg, 63%). EI-MS m/z 841.2 (M$^+$).

f) N-(2-Bromophenyl)-N'-N{4-chloro-2-tert-butyldimethylsilyloxy-3-[(R)-3-N-9-fluorenylmethylformate)pyrrolidine]aminosulfonylphenyl}carbodiimide Following the general procedure for carbodiimide formation outlined in example 12, N-(2-bromophenyl)-N'-{chloro-2-tert-butyldimethylsilyloxy-3-[(R)-3-N-9-fluorenylmethylformate)pyrrolidine]aminosulfonylphenyl}thiourea (293 mg, 0.35 mmol), methanesulfonyl chloride (0.05 mL, 0.7 mmol) and triethylamine (0.1 mL, 0.7 mmol) were reacted to form the desired product (293 mg, crude). $^1$H NMR (CDCl$_3$) δ 0.39 (s, 6H), 1.05 (s, 9H), 1.90 (m, 1H), 2.18 (m, 1H), 3.14 (m, 1H), 3.39 (m, 3H), 3.48 (m, 1H), 4.2 (t, 1H), 4.4 (d, 2H), 5.06 (d, 1H), 7.16–7.43 (m, 10H), 7.59 (d, 1H), 7.7 (d, 1H).

g) N-(2-Bromophenyl)-N'-{4-chloro-2-hydroxy-3-[(R)-3-aminopyrrolidine]aminosulfonylphenyl}cyanoguanidine Following the general procedure for cyanoguanidine formation outlined in example 12, N-(2-bromophenyl)-N'-{4-chloro-2-tert-butyldimethylsilyloxy-3-[(R)-3-N-9-fluorenylmethylformate) pyrrolidine]aminosulfonylphenyl}carbodiimide (293 mg, 0.36 mmol), cyanamide (61 mg, 1.44 mmol) and N,N-diisopropylethylamine (56 mg, 0.43 mmol) were reacted, followed by desilylation with Cesium fluoride (66 mg, 0.43 mmol) and deprotected amino with 20% piperidine (4 mL) in THF (20 mL) at room temperature for 30 minutes to form the desired product (purified by Gilson HPLC, 53 mg, 25%). LC-MS m/z 513.2. $^1$H NMR (DMSO-d$_6$) δ 1.6 (m, 2H), 2.0 (m, 1H), 2.2 (m, 1H), 2.95 (t, 1H), 3.35 (m, 1H), 3.50 (m, 2H), 3.72 (m, 1H), 6.9 (d, 1H), 7.2 (t, 1H), 7.42 (m, 2H), 7.7 (t, 2H), 8.32 (s, 1H).

METHOD OF TREATMENT

The compounds of Formula (I), or a pharmaceutically acceptable salt thereof can be used in the manufacture of a medicine for the prophylactic or therapeutic treatment of any disease state in a human, or other mammal, which is exacerbated or caused by excessive or unregulated IL-8 cytokine production by such mammal's cell, such as but not limited to monocytes and/or macrophages, or other chemokines which bind to the IL 8 α or β receptor, also referred to as the type I or type II receptor.

Accordingly, the present invention provides a method of treating a chemokie mediated disease, wherein the chemokine is one which binds to an IL-8 α or β receptor and which method comprises administering an effective amount of a compound of Formula (I) or a pharmaceutically acceptable salt thereof. In particular, the chemokines are IL-8, GROα, GROβ, GROγ, NAP-2 or ENA-78.

The compounds of Formula (I) are administered in an amount sufficient to inhibit cytokine function, in particular IL8, GROα, GROβ, GROγ, NAP-2 or ENA-78, such that they are biologically regulated down to normal levels of physiological function, or in some case to subnormal levels, so as to ameliorate the disease state. Abnormal levels of IL-8, GROα, GROβ, GROγ, NAP-2 or ENA-78 for instance in the context of the present invention, constitute: (i) levels of free IL-8 greater than or equal to 1 picogram per mL; (ii) any cell associated EL-8, GROα, GROβ, GROγ, NAP-2 or ENA-78 above normal physiological levels; or (iii) the presence of IL-8, GROα, GROβ, GROγ, NAP-2 or ENA-78 above basal levels in cells or tissues in which IL-8, GROα, GROβ, GROγ, NAP-2 or ENA-78 respectively, is produced.

The compounds of Formula (I), in generally have been shown to have a longer $t_{1/2}$ and improved oral bioavailabilty over the compounds disclosed in WO 96/25157 and WO 97/29743 whose disclosures are incorporated herein by reference.

There are many disease states in which excessive or unregulated IL-8 production is implicated in exacerbating and/or causing the disease. Chemokine mediated diseases include psoriasis, atopic dermatitis, osteo arthritis, rheumatoid arthritis, asthma, chronic obstructive pulmonary disease, adult respiratory distress syndrome, inflammatory bowel disease, Crohn's disease, ulcerative colitis, stroke, septic shock, multiple sclerosis, endotoxic shock, gram negative sepsis, toxic shock syndrome, cardiac and renal reperfusion injury, glomerulonephritis, thrombosis, graft vs. host reaction, Alzheimer's disease, allograft rejections, malaria, restenosis, angiogenesis, atherosclerosis, osteoporosis, gingivitis and undesired hematopoietic stem cells release and diseases caused by respiratory viruses, herpesviruses, and hepatitis viruses, meningitis, cystic fibrosis, pre-term labor, cough, pruzitus, multi-organ dysfunction, trauma, strains, sprains, contusions, psoriatic arthritis, herpes, encephalitis, CNS vasculitis, traumatic brain injury, CNS tumors, subarachnoid hemorrhage, post surgical trauma, interstitial pneumonitis, hypersensitivity, crystal induced arthritis, acute and chronic pancreatitis, acute alcoholic hepatitis, necrotizing enterocolitis, chronic sinusitis, uveitis, polymyositis, vasculitis, acne, gastric and duodenal ulcers, celiac disease, esophagitis, glossitis, airflow obstruction, airway hyperresponsiveness, bronchiolitis obliterans organizing pneumonia, bronchiectasis, bronchiolitis, bronchiolitis obliterans, chronic bronchitis, cor pulmonae, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertropy, sarcoidosis, small airway disease, ventilation-perfusion mismatching, wheeze, colds and lupus.

These diseases are primarily characterized by massive neutrophil infiltration, T-cell infiltration, or neovascular growth, and are associated with increased IL-8, GROα, GROβ, GROγ, NAP-2 or ENA-78 production which is responsible for the chemotaxis of neutrophils into the inflammatory site or the directional growth of endothelial cells. In contrast to other inflammatory cytokines (IL-1, TNF, and IL-6), I8, GROα, GROβ, GROγ, NAP-2 or ENA-78 have the unique property of promoting neutrophil chemotaxis, enzyme release including but not limited to elastase release as well as superoxide production and activation. The cc-chemokines but particularly, GROα, GROβ, GROγ, NAP-2 or ENA-78, working through the IL-8 type I or II receptor can promote the neovascularization of tumors by promoting the directional growth of endothelial cells. Therefore, the inhibition of IL-8 induced chemotaxis or activation would lead to a direct reduction in the neutrophil infiltration.

Recent evidence also implicates the role of chemokines in the treatment of HIV infections, Littleman et al., *Nature* 381, pp. 661 (1996) and Koup et al., *Nature* 381, pp. 667 (1996).

Present evidence also indicates the use of IL-8 inhibitors in the treatment of atherosclerosis. The first reference, Boisvert et al., *J. Clin. Invest*, 1998, 101:353–363 shows, through bone marrow transplantation, that the absence of IL-8 receptors on stem cells (and, therefore, on monocytes/macrophages) leads to a reduction in the development of atherosclerotic plaques in LDL receptor deficient mice. Additional supporting references are: Apostolopoulos, et al., *Arterioscler. Thromb. Vasc. Biol.* 1996, 16:1007–1012; Liu, et al., *Arterioscler. Thromb. Vasc. Biol*, 1997, 17:317–323; Rus, et al., *Atherosclerosis*. 1996, 127:263–271.; Wang et al., *J. Biol. Chem.* 1996, 271:8837–8842; Yue, et al., *Eur. J. Pharmacol*. 1993, 240:81–84; Koch, et al., *Am. J. Pathol.*, 1993, 142:1423–1431.; Lee, et al., *Immunol. Lett.*, 1996, 53, 109–113.; and Terkeltaub et al., *Arterioscler. Thromb.*, 1994, 14:47–53.

The present invention also provides for a means of treating, in an acute setting, as well as preventing, in those individuals deemed susceptible to, CNS injuries by the chemokine receptor antagonist compounds of Formula (I).

CNS injuries as defined herein include both open or penetrating head trauma, such as by surgery, or a closed head trauma injury, such as by an injury to the head region. Also included within this definition is ischemic stroke, particularly to the brain area.

Ischemic stroke may be defined as a focal neurologic disorder that results from insufficient blood supply to a particular brain area, usually as a consequence of an embolus, thrombi, or local atheromatous closure of the blood vessel. The role of inflammatory cytokines in this area has been emerging and the present invention provides a mean for the potential treatment of these injuries. Relatively little treatment, for an acute injury such as these has been available.

TNF-α is a cytokine with proinflammatory actions, including endothelial leukocyte adhesion molecule expression. Leukocytes infiltrate into ischemic brain lesions and hence compounds, which inhibit or decrease levels of TNF would be useful for treatment of ischemic brain injury. See Liu et al., *Stroke*, Vol. 25., No. 7, pp. 1481–88 (1994) whose disclosure is incorporated herein by reference.

Models of closed head injuries and treatment with mixed 5-LO/CO agents is discussed in Shohami et al., *J. of Vaisc & Clinical Physiology and Pharmacology*, Vol. 3, No. 2, pp. 99–107 (1992) whose disclosure is incorporated herein by reference. Treatment, which reduced edema formation, was found to improve functional outcome in those animals treated.

The compounds of Formula (I) are administered in an amount sufficient to inhibit IL8, binding to the IL-8 alpha or beta receptors, from binding to these receptors, such as evidenced by a reduction in neutrophil chemotaxis and activation. The discovery that the compounds of Formula (I) are inhibitors of IL-8 binding is based upon the effects of the compounds of Formulas (I) in the in vitro receptor binding assays which are described herein. The compounds of Formula (I) have been shown to be inhibitors of type II IL-8 receptors.

As used herein, the term "IL-8 mediated disease or disease state" refers to any and all disease states in which IL-8, GROα, GROβ, GROγ, NAP-2 or ENA-78 plays a role, either by production of IL-8, GROα, GROβ, GROγ, NAP-2 or ENA-78 themselves, or by IL,8, GROα, GROβ, GROγ, NAP-2 or ENA-78 causing another monokine to be released, such as but not limited to IL-1, IL-6 or TNF. A disease state in which, for instance, IL-1 is a major component, and whose production or action, is exacerbated or secreted in response to IL-8, would therefore be considered a disease state mediated by IL-8.

As used herein, the term "chemokine mediated disease or disease state" refers to any and all disease states in which a chemokine which binds to an IL-8 α or β receptor plays a role, such as but not limited to IL-8, GRO-α, GRO-β, GROγ, NAP-2 or ENA-78. This would include a disease state in which, IL-8 plays a role, either by production of IL-8 itself, or by IL-8 causing another monokine to be released, such as but not limited to IL-1, IL-6 or TNF. A disease state in which, for instance, IL-1 is a major component, and whose production or action, is exacerbated or secreted in response to IL-8, would therefore be considered a disease stated mediated by IL-8.

As used herein, the term "cytokine" refers to any secreted polypeptide that affects the functions of cells and is a molecule, which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL1), Interleukin-6 (IL6), Interleukin-8 (IL-8), Tumor Necrosis Factor-alpha (TNF-α) and Tumor Necrosis Factor beta (TNF-β).

As used herein, the term "chemokine" refers to any secreted polypeptide that affects the functions of cells and is a molecule which modulates interactions between cells in the immune, inflammatory or hematopoietic response, similar to the term "cytokine" above. A chemokine is primarily secreted through cell transmembranes and causes chemotaxis and activation of specific white blood cells and leukocytes, neutrophils, monocytes, macrophages, T-cells, B-cells, endothelial cells and smooth muscle cells. Examples of chemokines include, but are not limited to IL-8, GRO-α, GRO-β, GRO-γ, NAP-2, ENA-78, IP-10, MIP-1α, MIP-β, PF4, and MCP 1, 2, and 3.

The present compounds are also useful in normalizing leukocyte counts as well as normalizing levels of circulating chemokines.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the Formulation. It may however comprise as much as 10% w/w but preferably will comprise less than 5% w/w, more preferably from 0.1% to 1% w/w of the Formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I) the daily oral dosage regimen will preferably be from about 0.01 to about 80 mg/kg of total body weight. The daily parenteral dosage regimen about 0.001 to about 80 mg/kg of total body weight. The daily topical dosage regimen will preferably be from 0.1 mg to 150 mg, administered one to four, preferably two or three times daily. The daily inhalation dosage regimen will preferably be from about 0.01 mg/kg to about I mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The invention will now be described by reference to the following biological examples which are merely illustrative and are not to be construed as a limitation of the scope of the present invention.

BIOLOGICAL EXAMPLES

The IL-8, and GRO-α chemokine inhibitory effects of compounds of the present invention are determined by the following in vitro assay:

Receptor Binding Assays $[^{125}I]$ IL-8 (human recombinant) is obtained from Amersham Corp., Arlington Heights, Ill., with specific activity 2000 Ci/mmol. GRO-α is obtained from NEN-New England Nuclear. All other chemicals are of analytical grade. High levels of recombinant human IL-8 type α and β receptors were individually expressed in Chinese hamster ovary cells as described previously (Holmes, et al., *Science*, 1991, 253, 1278). The Chinese hamster ovary membranes were homogenized according to a previously described protocol (Haour, et al., *J. Biol. Chem.*, 249 pp 2195–2205 (1974)). Except that the homogenization buffer is changed to 10 mM Tris-HCL, 1 mM $MgSO_4$, 0.5 mM EDTA (ethylene-diaminetetra-acetic acid), 1 mM PMSF (α-toluenesulphonyl fluoride), 0.5 mg/L Leupeptin, pH 7.5. Membrane protein concentration is determined using Pierce Co. micro-assay kit using bovine serum albumin as a standard. All assays are performed in a 96-well micro plate format. Each reaction mixture contains $^{125}$I IL-8 (0.25 nM) or $^{125}$I GRO-α and 0.5 μg/mL of IL-8Rα or 1.0 μg/mL of IL-8Rβ membranes in 20 mM Bis-Trispropane and 0.4 mM Tris HCl buffers, pH 8.0, containing 1.2 mM $MgSO_4$, 0.1 mM EDTA, 25 mM Na and 0.03% CHAPS. In addition, drug or compound of interest is added which has been pre-dissolved in DMSO so as to reach a final concentration of between 0.01 nM and 100 uM. The assay is initiated by addition of $^{125}$I-IL8. After 1 hour at room temperature the plate is harvested using a Tomtec 96-well harvester onto a glass fiber filtermat blocked with 1% polyethylenimine/0.5% BSA and washed 3 times with 25 mM NaCl, 10 mM TrisHCl, 1 mM $MgSO_4$, 0.5 mM EDTA, 0.03% CHAPS, pH 7.4. The filter is then dried and counted on the Betaplate liquid scintillation counter. The recombinant IL-8 Rα, or Type I, receptor is also referred to herein as the non-permissive receptor and the recombinant IL-8 Rβ, or Type II, receptor is referred to as the permissive receptor.

Representative compounds of Formula (I), Examples 1 to 106 have exhibited positive inhibitory activity in this assay at $IC_{50}$ levels <30 uM.

Chemotaxis Assay

The in vitro inhibitory properties of these compounds are determined in the neutrophil chemotaxis assay as described in Current Protocols in Immunology, vol. I, Suppl 1, Unit 6.12.3., whose disclosure is incorporated herein by reference in its entirety. Neutrophils where isolated from human blood as described in Current Protocols in Immunology Vol. I, Suppl 1 Unit 7.23.1, whose disclosure is incorporated herein by reference in its entirety. The chemoattractants IL8, GRO-α, GRO-β, GRO-γ and NAP-2 are placed in the bottom chamber of a 48 multiwell chamber (Neuro Probe, Cabin John, Md.) at a concentration between 0.1 and 100 nM. The two chambers are separated by a 5 uM polycarbonate filter. When compounds of this invention are tested, they are mixed with the cells (0.001–1000 nM) just prior to the addition of the cells to the upper chamber. Incubation is allowed to proceed for between about 45 and 90 min at about 37° C. in a humidified incubator with 5% $CO_2$. At the end of the incubation period, the polycarbonate membrane is removed and the topside washed, the membrane then stained using the Diff Quick staining protocol (Baxter Products, McGaw Park, Ill., USA). Cells which have chemotaxed to the chemokine are visually counted using a microscope. Generally, four fields are counted for each sample, these numbers are averaged to give the average number of cells which had migrated. Each sample is tested in triplicate and each compound repeated at least four times. To certain cells (positive control cells) no compound is added, these cells represent the maximum chemotactic response of the cells. In the case where a negative control (unstimulated) is desired, no chemokine is added to the bottom chamber. The difference between the positive control and the negative control represents the chemotactic activity of the cells.

Elastase Release Assay

The compounds of this invention are tested for their ability to prevent Elastase release from human neutrophils.

Neutrophils are isolated from human blood as described in Current Protocols in Immunology Vol. I, Suppl 1 Unit 7.23.1. PMNs $0.88 \times 10^6$ cells suspended in Ringer's Solution (NaCl 118, KCl 4.56, $NaHCO_3$ 25, $KH_2PO_4$ 1.03, Glucose 11.1, HEPES 5 mM, pH 7.4) are placed in each well of a 96 well plate in a volume of 50 ul. To this plate is added the test compound (0.001–1000 nM) in a volume of 50 ul, Cytochalasin B in a volume of 50 ul (20 ug/ml) and Ringers buffer in a volume of 50 ul. These cells are allowed to warm (37° C., 5% CO2, 95% RH) for 5 min before IL-8, GROα, GROβ, GROγ or NAP-2 at a final concentration of 0.01–1000 nM was added. The reaction is allowed to proceed for 45 min before the 96 well plate is centrifuged (800×g 5 min.) and 100 ul of the supernatant removed. This supernatant is added to a second 96 well plate followed by an artificial elastase substrate (MeOSuc-Ala-Ala-Pro-Val-AMC, Nova Biochem, La Jolla, Calif.) to a final concentration of 6 ug/ml dissolved in phosphate buffered saline. Immediately, the plate is placed in a fluorescent 96 well plate reader (Cytofluor 2350, Millipore, Bedford, Mass.) and data collected at 3 min intervals according to the method of Nakajima et al *J. Biol. Chem.* 254 4027 (1979). The amount of Elastase released from the PMNs is calculated by measuring the rate of MeOSuc-Ala-Ala-Pro-Val-AMC degradation.

TNF-α in Traumatic Brain Injury Assay

The present assay provides for examination of the expression of tumor necrosis factor mRNA in specific brain regions, which follow experimentally, induced lateral fluid-percussion traumatic brain injury (TBI) in rats. Adult Sprague-Dawley rats (n=42) were anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury, n=18). Animals are sacrificed by decapitation at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) are prepared. Total RNA are isolated and Northern blot hybridization is performed and quantitated relative to an TNF-α positive control RNA (macrophage=100%). A marked increase of 1NF-α mRNA expression is observed in LH (104±17% of positive control, p <0.05 compared with sham), LC (105±21%, p<0.05) and LA (69±8%, p<0.01) in the traumatized hemisphere 1 hr. following injury. An increased TNF-α mRNA expression is also observed in LH (46±8%, p<0.05), LC (30±3%, p<0.01) and LA (32±3%, p<0.01) at 6 hr which resolves by 24 hr following injury. In the contralateral hemisphere, expression of TNF-α mRNA is increased in RH (46±2%, p<0.01), RC (4±3%) and RA (22±8%) at 1 hr and in RH (28±11%), RC (7±5%) and RA (26±6%, p<0.05) at 6 hr but not at 24 hr following injury. In sham (surgery without injury) or naive animals, no consistent changes in expression of TNF-α mRNA are observed in any of the 6 brain areas in either hemisphere at any times. These results indicate that following parasagittal fluid-percussion brain injury, the temporal expression of TNF-α mRNA is altered in specific brain regions, including those of the non-traumatized hemisphere. Since TNF-α is able to induce nerve growth factor (NGF) and stimulate the release of other cytokines from activated astrocytes, this post-traumatic alteration in gene expression of TNF-α plays an important role in both the acute and regenerative response to CNS trauma.

CNS Injury Model for IL-1β mRNA

This assay characterizes the regional expression of interleukin-1β (IL-1β) mRNA in specific brain regions following experimental lateral fluid-percussion traumatic brain injury (TBI) in rats. Adult Sprague-Dawley rats (n=42) are anesthetized with sodium pentobarbital (60 mg/kg, i.p.) and subjected to lateral fluid-percussion brain injury of moderate severity (2.4 atm.)centered over the left temporaparietal cortex (n=18), or "sham" treatment (anesthesia and surgery without injury). Animals are sacrificed at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) are prepared. Total RNA is isolated and Northern blot hybridization was performed and the quantity of brain tissue IL-1β mRNA is presented as percent relative radioactivity of IL-1β positive macrophage RNA which was loaded on the same gel. At 1 hr following brain injury, a marked and significant increase in expression of IL-1β mRNA is observed in LC (20.0±0.7% of positive control, n=6, p<0.05 compared with sham animal), LH (24.5±0.9%, p<0.05) and LA(21.5±3.1%, p<0.05) in the injured hemisphere, which remained elevated up to 6 hr. post injury in the LC (4.0±0.4%, n=6, p<0.05) and LH (5.0±1.3%, p<0.05). In sham or naive animals, no expression of IL-1β mRNA is observed in any of the respective brain areas. These results indicate that following TBI, the temporal expression of IL-1β mRNA is regionally stimulated in specific brain regions. These regional changes in cytokines, such as IL-1β play a role in the post-traumatic.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of the formula:

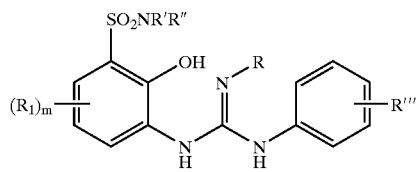

(I)

wherein:
R is selected from the group consisting of cyano, $OR_{11}$, $C(O)NR_{15}R_{16}$, $R_{18}$, $C(O)OR_{11}$, $C(O)R_{11}$, and $S(O)_2R_{17}$;

R'R" is independently selected from the group consisting of hydrogen, $NR_6R_7$, OH, $OR_a$, $C_{1-5}$alkyl, aryl, aryl$C_{1-4}$alkyl, aryl C2-4alkenyl; cycloalkyl, cycloalkyl $C_{1-5}$ alkyl, heteroaryl, heteroaryl$C_{1-4}$alkyl, heteroaryl$C_{2-4}$ alkenyl, heterocyclic, heterocyclic $C_{1-4}$alkyl, and a heterocyclic $C_{2-4}$alkenyl moiety, all of which moieties may be optionally substituted one to three times independently by a substituent selected from the group consisting of halogen, nitro, halosubstituted $C_{1-4}$alkyl, $C_{12-4}$alkyl, amino, mono- or di-$C_{1-4}$ alkyl substituted amine, $OR_a$, $C(O)R_a$, $NR_aC(O)OR_a$, $OC(O)NR_6R_7$, hydroxy, $NR_9C(O)R_a$, $S(O)_mR_a$, $C(O)NR_6R_7$, $C(O)OH$, $C(O)OR_a$, $S(O)_tNR_6R_7$, and $NHS(O)_tR_a$; or the two $R_b$ substituents join to form a 3–10 membered ring, optionally substituted and containing, in addition to optionally substituted $C_{1-4}$ alkyl, independently, 1 to 3 $NR_a$, O, S, SO, or $SO_2$ moieties, which moieties can be optionally unsaturated;

R''' is selected from the group consisting of Y hydrogen, halogen, nitro, cyano, halosubstituted $C_{1-10}$ alkyl, $C_{1-10}$ alkyl, $C_{2-10}$ alkenyl, $C_{1-10}$ alkoxy, halosubstituted $C_{1-10}$ alkoxy, azide, $(CR_8R_8)_qS(O)_rR_a$, $(CR_8R_8)_qOR_a$, hydroxy, hydroxy substituted $C_{1-4}$alkyl, aryl, aryl $C_{1-4}$ alkyl, aryloxy, aryl$C_{1-4}$ alkyloxy, aryl $C_{2-10}$ alkenyl, heteroaryl, heteroarylalkyl, heteroaryl $C_{1-4}$ alkyloxy, heteroaryl $C_{2-10}$ alkenyl, heterocyclic, heterocyclic $C_{1-4}$alkyl, heterocyclic$C_{2-10}$ alkenyl, $(CR_8R_8)_qNR_4R_5$, $C_{2-10}$ alkenyl $C(O)NR_4R_5$, $(CR_8R_8)_qC(O)NR_4R_5$, $(CR_8R_8)_qC(O)NR_4R_{10}$, $S(O)_3R_8$, $(CR_8R_8)_qC(O)R_{11}$, $C_{2-10}$ alkenyl$C(O)R_{11}$, $(CR_8R_8)_qC(O)OR_{11}$, $C_{2-10}$alkenyl$C(O)OR_{11}$, $(CR_8R_8)_qOC(O)R_{11}$, $(CR_8R_8)_qNR_4C(O)R_{11}$, $(CR_8R_8)_qNHS(O)_tR_{13}$, $(CR_8R_8)_qS(O)_tNR_4R_5$, $(CR_8R_8)_qC(NR_4)NR_4R_5$, and $(CR_8R_8)_qNR_4C(NR_5)R_{11}$; or two Y moieties together form O—$(CH_2)_s$—O or a 5 to 6 membered saturated or unsaturated ring, such that the alkyl, aryl, arylalcyl, heteroaryl, heteroaryl alkyl, heterocyclic, and heterocyclicalkyl groups may be optionally substituted;

$R_1$ is independently selected from the group consisting of hydrogen, halogen, nitro, cyano, $C_{1-10}$ alkyl, halosubstituted $C_{1-10}$ alkyl, $C_{2-10}$ alkenyl, $C_{1-10}$ alkoxy, halosubstituted $C_{1-10}$alkoxy, azide, $S(O)_tR_4$, $(CR_8R_8)_q S(O)_tR_4$, hydroxy, hydroxy substituted $C_{1-4}$alkyl, aryl, aryl $C_{1-4}$ alkyl, aryl $C_{2-10}$ alkenyl, aryloxy, aryl $C_{1-4}$ alkyloxy, heteroaryl, heteroarylalkyl, heteroaryl $C_{2-10}$ alkenyl, heteroaryl $C_{1-4}$ alkyloxy, heterocyclic, heterocyclic $C_{1-4}$alkyl, heterocyclic$C_{1-4}$alkyloxy, heterocyclic$C_{2-10}$ alkenyl, $(CR_8R_8)_qNR_4R_5$, $(CR_8R_8)_qC(O)NR_4R_5$, $C_{2-10}$ alkenyl $C(O)NR_4R_5$, $(CR_8R_8)_qC(O)NR_4R_{10}$, $S(O)_3R_8$, $(CR_8R_8)_qC(O)R_{11}$, $C_{2-10}$ alkenyl $C(O)R_{11}$, $C_{2-10}$ alkenyl $C(O)OR_{11}$, $(CR_8R_8)_qC(O)OR_{11}$, $(CR_8R_8)_qOC(O)R_{11}$, $(CR_8R_8)_qNR_4C(O)R_{11}$, $(CR_8R_8)_qC(NR_4)NR_4R_5$, $(CR_8R_8)_qNR_4C(NR_5)R_{11}$, $(CR_8R_8)_qNHS(O)_tR_{13}$, and $(CR_8R_8)_qS(O)_tNR_4R_5$; or two $R_1$ moieties together form O—$(CH_2)_s$O or a 5 to 6 membered saturated or unsaturated ring, wherein the alkyl, aryl, arylalkyl, heteroaryl, and heterocyclic moieties may be optionally substituted.

2. The compound according to claim 1 wherein $R_1$ is substituted in the 4-position by an electron withdrawing moiety.

3. The compound according to claim 2 wherein $R_1$ is halogen, cyano or nitro.

4. The compound according to claim 3 wherein $R_1$ is halogen.

5. The compound according to claim 4 wherein $R_1$ is independently fluorine, chlorine, or bromine.

6. The compound according to claim 1 wherein Y is mono-substituted in the 2'-position or 3'-position, or is disubstituted in the 2'- or 3'-position of a monocyclic ring.

7. The compound according to claim 6 wherein Y is halogen.

8. The compound according to claim 4 wherein Y is independently fluorine, chlorine, or bromine.

9. The compound according to claim 1 wherein $R_b$ is hydrogen, $C_{1-4}$ alkyl, $C_{1-4}$ alkyl substituted with C(O)OH, or C(O)OR$_a$.

10. The compound according to claim 1 wherein Y is halogen, n is 1 or 2, $R_1$ is halogen, m is 1 or 2, and $R_b$ is independently hydrogen, $C_{1-4}$ alkyl, $C_{1-4}$ alkyl substituted with C(O)OH, or C(O)OR$_a$.

11. The compound according to claim 1 which is selected from the group consisting of:

N-(2-bromophenyl)-N'-[4-chloro-2-hydroxy-3-(N",N"dimethylaminosulfonyl)phenyl]cyanoguanidine;

N-[4-chloro-2-hydroxy-3-(N",N"-dimethylaminosulfonyl)phenyl]-N'-(2,3-dichlorophenyl)cyanoguanidine;

N-(2-bromophenyl)-N'-[-chloro-2-hydroxy-3-[S-(+)-(2-methoxymethyl)pyrrolidin-1-yl]aminosulfonylphenyl]cyanoguanidine;

N-(2,3-dichlorophenyl)-N'-[4-chloro-2-hydroxy-3-[S-(+)-(2-methoxymethyl)pyrrolidin-1-yl]aminosulfonylphenyl]cyanoguanidine;

N-phenyl-N'-[4-chloro-2-hydroxy-3-[S-(+)-(2-methoxymethyl)pyrrolidin-1-yl]aminosulfonylphenyl]cyanoguanidine;

N-(2-bromophenyl)-N'-[4-chloro-2-hydroxy-3-[R-(2-methoxymethyl)pyrrolidin-1-yl]aminosulfonylphenyl]cyanoguanidine;

N-(2,3-dichlorophenyl)-N'-[4-chloro-2-hydroxy-3-[R-(2-methoxymethyl)pyrrolidin-1-yl]aminosulfonylphenyl]cyanoguanidine;

N-(2-bromophenyl)-N'-[4-chloro-2-hydroxy-3-(N"-isoxazolidinylaminosulfonylphenyl]cyanoguanidine;

N-(2,3-dichlorophenyl)-N'-[4-chloro-2-hydroxy-3-(N"-isoxazolidinylaninosulfonylphenyl]cyanoguanidine;

N-(2-bromophenyl)-N'-[4-chloro-2-hydroxy-3-(N"-tetrahydroisoxazylaminosulfonyl)phenyl]cyanoguanidine;

N-(2,3-dichlorophenyl)-N'-[4-chloro-2-hydroxy-3-(N"-tetrahydroisoxazylaminosulfonyl)phenyl]cyanoguanidine;

N-(2,3-dichlorophenyl)-N'-[4-chloro-2-hydroxy-3-(4-thiomorpholinylaminosulfonyl)phenyl]cyanoguanidine;

N-[4-chloro-2-hydroxy-3-[N",N"-dimethylaminosulfonyl]phenyl]-N'-(2-bromophenyl)propylguanidine;

N-(2-bromophenyl)-N'-[4-chloro-2-hydroxy-3-(4oxidothiomorpholino)amino sulfonylphenyl]cyanoguanidine;

N-(2,3-chlorophenyl)-N'-[4-chloro-2-hydroxy-3-(4oxidothiomorpholino)amino sulfonylphenyl]cyanoguanidine;

N-(2-bromophenyl)-N'-[4-chloro-2-hydroxy-3-(N"-methylpiperazino)amino sulfonylphenyl]cyanoguanidine;

N-(2,3-dichlorophenyl)-N'-[4-chloro-2-hydroxy-3-(N"-methylpiperazino)amino sulfonylphenyl]cyanoguanidine;

N-(2-bromophenyl)-N'-N[4-chloro-2-hydroxy-3-(N"-ethylmorpholino)amino sulfonylphenyl]cyanoguanidine;

N-(2,3-dichlorophenyl)-N'-[4-chloro-2-hydroxy-3-(N"-ethylmorpholino)amino sulfonylphenyl]cyanoguanidine;

N-(2-bromophenyl)-N'-{4-chloro-2-hydroxy-3-[N"-ethyl-2-(2-ethylpyrrolidino)]amino sulfonylpheny}cyanoguanidine;

N-(2,3-dichlorophenyl)-N'-{4-chloro-2-hydroxy-3-[N"-ethyl-2-(2-ethylpyrrolidino)]amino sulfonylpheny}cyanoguanidine;

N-(2-bromophenyl)-N'-{4-chloro-2-hydroxy-3-[S-(+)-(2-carboxy)pyrrolidin-1-yl]amino sulfonylpheny}cyanoguanidine;

N-(2,3-dichlorophenyl)-N'-{4-chloro-2-hydroxy-3-[S-(+)-(2-carboxy)pyrrolidin-1-yl]amino sulfonylpheny}cyanoguanidine;

N-(2-bromo-3-fluorophenyl)-N'-[4-chloro2-hydroxy-3-[S-(+)-(2-methoxymethyl)pyrrolidin-1-yl]sulfonylphenyl]cyanoguanidine;

N-(2-phenoxyphenyl)-N'-[4-chloro-2-hydroxy-3-[S-(+)-(2-methoxymethyl)pyrrolidin-1-yl]sulfonylphenyl]cyanoguanidine; and N-(2-benzoxyphenyl)-N'-[4-chloro-2-hydroxy-3-[S-(+)-(2-methoxymethyl)pyrrolidin-1-yl]sulfonylphenyl]cyanoguanidine;

or a pharmaceutically acceptable salt thereof.

12. A pharmaceutical composition comprising a compound according to claim 1 and a pharmaceutically acceptable carrier or diluent.

13. A method of treating a chemokine mediated disease, wherein the chemokine binds to an IL-8 a or b receptor in a mammal, which method comprises administering to said mammal an effective amount of a compound of the formula according to claim 1.

14. The method according to claim 13 wherein the mammal is afflicted with a chemokine mediated disease selected from the group consisting of psoriasis, atopic dermatitis, osteo arthritis, rheumatoid arthritis, asthma, chronic obstructive pulmonary disease, adult respiratory distress syndrome, inflammatory bowel disease, Crohn's disease, ulcerative colitis, stroke, septic shock, multiple sclerosis, endotoxic shock, gram negative sepsis, toxic shock syndrome, cardiac and renal reperfusion injury, glomerulonephritis, thrombosis, graft vs. host reaction, alzheimers disease, allograft rejections, malaria, restenosis, angiogenesis, atherosclerosis, osteoporosis, gingivitis and undesired hematopoietic stem cells release and diseases caused by respiratory viruses, herpesviruses, and hepatitis viruses, meningitis, cystic fibrosis, pre-term labor, cough, pruritus, multi-organ dysfucntions, trauma, strains, sprains, contusions, psoriatic arthritis, herpes, encephalitis, CNS vasculitis, traumatic brain injury, CNS tumors, subarachnoid hemorrhage, post surgical trauma, interstitial pneumonitis, hypersensitivity, crystal induced arthritis, acute and chronic pancreatitis, acute alcoholic hepatitis, necrotizing enterocolitis, chronic sinusitis, uveitis, polymyositis, vasculitis, acne, gastric and duodenal ulcers, celiac disease, esophagitis, glossitis, airflow obstruction, airway hyperresponsiveness, bronchiolitis obliterans organizing pneumonia, bronchiectasis, bronchiolitis, bronchiolitis obliterans, chronic bronchitis, cor pulmonae, dyspnea, emphysema, hypercapnea, hyperinflation, hypoxemia, hyperoxia-induced inflammations, hypoxia, surgerical lung volume reduction, pulmonary fibrosis, pulmonary hypertension, right ventricular hypertropy, sarcoidosis, small airway disease, ventilation-perfusion mismatching, wheeze, colds and lupus.

* * * * *